US008222246B2

(12) United States Patent
Buettelmann et al.

(10) Patent No.: US 8,222,246 B2
(45) Date of Patent: Jul. 17, 2012

(54) SUBSTITUTED ISOXAZOLES

(75) Inventors: Bernd Buettelmann, Schopfheim (DE);
Stephen Deems Gabriel, Morristown, NJ (US); Steven Paul Hanlon, Bottmingen (CH); Roland Jakob-Roetne, Inzlingen (DE); Matthew C. Lucas, Verona, NJ (US); Paul Spurr, Riehen (CH); Andrew Thomas, Binningen (CH); Pius Waldmeier, Wegenstetten (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 296 days.

(21) Appl. No.: 12/748,524

(22) Filed: Mar. 29, 2010

(65) Prior Publication Data

US 2010/0256127 A1 Oct. 7, 2010

(30) Foreign Application Priority Data

Apr. 2, 2009 (EP) ..................................... 09157200

(51) Int. Cl.
C07D 413/02 (2006.01)
A61K 31/44 (2006.01)
(52) U.S. Cl. ..................... 514/227.2; 514/340; 544/58.2; 546/272.1
(58) Field of Classification Search .......................... None
See application file for complete search history.

(56) References Cited

U.S. PATENT DOCUMENTS

| 4,639,266 A | 1/1987 | Heubach et al. |
|---|---|---|
| 2003/0055085 A1 | 3/2003 | Wagenen et al. |
| 2004/0006226 A1 | 1/2004 | Ladduwahetty et al. |

FOREIGN PATENT DOCUMENTS

| DE | 3525205 | 3/1986 |
|---|---|---|
| GB | 2336589 | 10/1999 |
| JP | 2007230909 | 9/2007 |
| WO | 00/77008 | 12/2000 |
| WO | 0129015 | 4/2001 |
| WO | 0134603 | 5/2001 |
| WO | 0250062 | 6/2002 |
| WO | 02081474 | 10/2002 |
| WO | 03004027 | 1/2003 |
| WO | 03015771 | 2/2003 |
| WO | 03044017 | 5/2003 |
| WO | 03/048132 | 6/2003 |
| WO | 2004046349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007/039389 | 4/2007 |
| WO | 2007039389 | 4/2007 |
| WO | 2007052843 | 5/2007 |
| WO | 2007076260 | 7/2007 |
| WO | 2007092751 | 8/2007 |
| WO | 2008025539 | 3/2008 |
| WO | 2008025540 | 3/2008 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909, 2007.
Roy et al., Synthesis, 2003 pp. 1347-1356.
White, et al., Journal of Organic Chemistry (1981), vol. 46(11) pp. 2273-2280.
Shi Shun et al , J. Org. Chem. vol. 68 (2003) pp. 6810-6813.
Lam et al., Bioarganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1980, vol. 49, pp. 522-523.
Hormi, Organic Syntheses, vol. 8, p. 247 (1993) & vol. 66, (1988), p. 173.
Andosova et al , Pharmaceutical Chemistry Journal (English Tianslation), vol. 12, No. 8, 1978, pp. 1019-1022.
Doyle, et al., Journal of the Chem. Society; 1903, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).

(Continued)

Primary Examiner — Zinna Northington Davis
(74) Attorney, Agent, or Firm — George W. Johnston; Patricia S. Rocha-Tramaloni; Kimberly J. Prior

(57) ABSTRACT

The present invention is concerned with novel hydroxy-methyl isoxazole derivatives of formula I

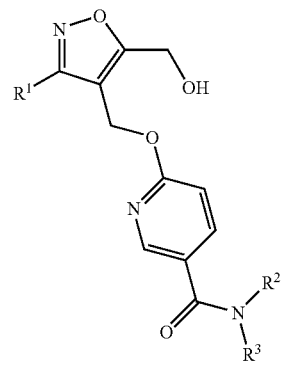

wherein $R^1$, $R^2$ and $R^3$ are as described herein, as well as pharmaceutically acceptable salts and esters thereof. The active compounds of the present invention have affinity and selectivity for GABA A α5 receptor. Further the present invention is concerned with the manufacture of the active compounds of formula I, pharmaceutical compositions containing them and their use as pharmaceuticals.

21 Claims, No Drawings

OTHER PUBLICATIONS

Seydel et al., J. Med Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol, 60 p. 3907-3909.
Otani et al., Neuroscience Letters, 2005, vol. 381 pp. 108-113.
Papadimitriou et al., Neuropsychobiology, 2001, vol. 43(3) pp. 141-144.
McCauley et al., American J. Med. Genetics, 2004, 131B, pp. 51-59.
Delong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.

SUBSTITUTED ISOXAZOLES

PRIORITY TO RELATED APPLICATION(S)

This application claims the benefit of European Patent Application No. 09157200.8, filed Apr. 2, 2009, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of $\alpha$, $\beta$ and $\gamma$ subunits.

Presently a total number of 21 subunits of the GABA A receptor have been cloned and sequenced. Three types of subunits ($\alpha$, $\beta$ and $\gamma$) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the $\alpha$ and $\gamma$ subunits. Among the recombinant GABA A receptors, $\alpha1\beta2\gamma2$ mimics many effects of the classical type-I BzR subtypes, whereas $\alpha2\beta2\gamma2$, $\alpha3\beta2\gamma2$ and $\alpha5\beta2\gamma2$ ion channels are termed type-II BzR.

It has been shown by McNamara and Skelton in Psychobiology, 1993, 21:101-108 that the benzodiazepine receptor inverse agonist $\beta$-CCM enhance spatial learning in the Morris watermaze. However, $\beta$-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A $\alpha5$ receptor partial or full inverse agonist which is relatively free of activity at GABA A $\alpha1$ and/or $\alpha2$ and/or $\alpha3$ receptor binding sites can be used to provide a medicament which is useful for enhancing cognition with reduced or without proconvulsant activity. It is also possible to use GABA A $\alpha5$ inverse agonists which are not free of activity at GABA A $\alpha1$ and/or $\alpha2$ and/or $\alpha3$ receptor binding sites but which are functionally selective for $\alpha5$ containing subunits. However, inverse agonists which are selective for GABA A $\alpha5$ subunits and are relatively free of activity at GABA A $\alpha1$, $\alpha2$ and $\alpha3$ receptor binding sites are preferred.

Literature has been published to establish the link between GABA A $\alpha5$ subunits and the treatment of various diseases of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

The present invention provides hydroxy-methyl isoxazoles having affinity and selectivity for GABA A $\alpha5$ receptor, their manufacture, pharmaceutical compositions containing them and their use as pharmaceuticals.

In particular, the present invention provides hydroxy-methyl isoxazoles of formula I

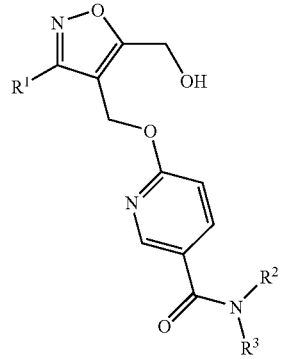

wherein $R^1$ is lower-alkyl, aryl or heteroaryl, wherein lower-alkyl is optionally substituted with 1-4 substituents independently selected from the group consisting of halogen, cyano, hydroxy and lower-alkoxy, and wherein aryl and heteroaryl are optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—$NH_2$, lower-alkyl-CO—N(H, lower-alkyl), lower-alkyl-CO—N(lower-alkyl)$_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, $CONH_2$, CON(H,lower-alkyl), CON(lower-alkyl)$_2$, cycloalkyl, heterocyclyl, aryl, heteroaryl, $NH_2$, N(H, lower-alkyl), N(lower-alkyl)$_2$, hydroxy, lower-alkoxy, phenyloxy, $SO_2$-lower-alkyl, $SO_2$—$NH_2$, $SO_2$—N(H,lower-alkyl) and $SO_2$—N(lower-alkyl)$_2$;

$R^2$ is hydrogen or lower-alkyl;

$R^3$ is lower-alkyl, lower-alkyl substituted by halogen, lower-alkyl substituted by hydroxy, cycloalkyl, cycloalkyl substituted by hydroxy, heterocyclyl, heterocyclyl substituted by lower-alkyl, heteroaryl, heteroaryl substituted by lower-alkyl, $(CH_2)_n$—O-lower-alkyl or $NR^4R^5$;

or wherein $R^2$ and $R^3$, together with the nitrogen atom to which they are attached, form a heterocyclyl;

n is 1 or 2;

$R^4$ and $R^5$ are each independently selected from hydrogen and lower-alkyl;

and pharmaceutically acceptable salts and esters thereof.

The present invention provides compounds of formula I and their pharmaceutically acceptable salts and esters and pharmaceutical compositions containing them. The invention also provides methods for the manufacture of such compounds and compositions. The invention further provides methods for the treatment or prevention of diseases related to the GABA A $\alpha5$ receptor. In particular, the compounds of present invention are inverse agonists of GABA A $\alpha5$.

The compounds of present invention and their pharmaceutically acceptable salts and esters can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

DETAILED DESCRIPTION OF THE INVENTION

Unless otherwise indicated, the following definitions are set forth to illustrate and define the meaning and scope of the various terms used to describe the invention herein.

The following definitions of the general terms apply irrespective of whether the terms in question appear alone or in combination.

The "nomenclature used in this application is based on AutoNom™ 2000, a Beilstein Institute computerized system for the generation of IUPAC systematic nomenclature. Chemical structures shown herein were prepared using ISIS™/Draw version 2.5. Any open valency appearing on a carbon, oxygen, sulfur or nitrogen atom in the structures herein indicates the presence of a hydrogen atom.

The term "substituted", unless specifically defined otherwise, means that the specified group or moiety can bear 1, 2, 3, 4, 5 or 6 substituents. Where any group carries multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. 1, 2, 3, 4 or 5 substituents are preferred, unless specifically defined otherwise. Particularly preferred are 1, 2, 3 or 4 substituents.

The term "halogen" refers to fluorine, chlorine, bromine and iodine, in particular fluorine and chlorine.

The term "lower-alkyl" denotes a saturated straight- or branched-chain group containing from 1 to 7 carbon atoms, for example, methyl, ethyl, propyl, isopropyl, n-butyl, isobutyl, sec-butyl or tert-butyl, as well as those groups specifically illustrated by the examples herein below. In particular lower-alkyl groups are methyl, isopropyl, n-butyl and tert-butyl, especially isopropyl.

The term "lower-alkoxy" denotes a group —O—R wherein R is lower-alkyl as defined above.

The term "lower-alkoxy-lower-alkyl" denotes an alkyl group as defined above in which at least one hydrogen atom has been replaced with a "lower-alkoxy" group as defined above, in partiuclar 2-methoxy-ethyl.

The term "cycloalkyl" refers to a monovalent saturated cyclic hydrocarbon radical of 3 to 7 ring carbon atoms, in particular 3 to 6 carbon atoms, such as cyclopropyl, cyclobutyl, cyclopentyl or cyclohexyl, as well as those groups specifically illustrated by the examples herein below. In particular cycloalkyls are cyclopropyl, cyclobutyl and cyclopentyl, especially cyclopropyl and cyclopentyl.

The term "heterocyclyl" refers to a monovalent 3 to 7 membered saturated or partly unsaturated monocyclic ring containing one, two or three ring heteroatoms selected from N, O and S. One or two ring heteroatoms are preferred. In particular, heterocyclyl are 4 to 6 membered heterocyclyl comprising one or two ring heteroatoms selected from N, O and S. S is optionally substituted by two oxo groups. Examples for heterocyclyl moieties are pyrrolidinyl, tetrahydro-furanyl, tetrahydro-pyranyl, tetrahydro-thienyl, tetrahydro-pyridinyl, tetrahydro-pyryl, azetidinyl, thiazolidinyl, oxazolidinyl, piperidinyl, morpholinyl, thiomorpholinyl, 1,1-dioxo-thiomorpholin-4-yl, piperazinyl, azepanyl, diazepanyl, oxazepanyl or dihydro-oxazolyl, as well as those groups specifically illustrated by the examples herein below. Specific heterocyclyls include pyrrolidin-1-yl, tetrahydro-furan-3-yl, tetrahydro-pyran-4-yl, morpholin-4-yl, azetidin-1-yl, thiomorpholin-4-yl, 1,1-dioxo-thiomorpholin-4-yl and oxetan-3-yl.

The term "aryl" refers to a monovalent aromatic carbocyclic ring system, comprising 6 to 14, in particular 6 to 10, carbon atoms and having at least one aromatic ring or multiple condensed rings in which at least one ring is aromatic. Examples for aryl are phenyl, naphthyl, biphenyl or indanyl, as well as those groups specifically illustrated by the examples herein below. Preferred aryl is phenyl. Aryl can also be substituted e.g. as defined below and in the claims.

The term "heteroaryl" refers to an aromatic 5 to 6 membered monocyclic ring or 9 to 10 membered bicyclic ring containing 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl or isoquinolinyl, as well as those groups specifically illustrated by the examples herein below. More particularly heteroaryl groups are pyridine-2-yl and pyrazol-4-yl. Heteroaryl can also be substituted e.g. as defined below and in the claims.

The term "lower-alkyl substituted by cycloalkyl" denotes a lower-alkyl group as defined above wherein at least one of the hydrogen atoms of the alkyl group is replaced by a cycloalkyl group. Examples of lower-alkyl substituted by cycloalkyl include but are not limited to cyclopropylmethyl, cyclopropylethyl, cyclobutylpropyl and cyclopentylbutyl. A particular lower-alkyl substituted by cycloalkyl is cyclopropylmethyl.

The term "lower-alkyl substituted by halogen" refers to lower-alkyl groups which are mono- or multiply substituted with halogen. Examples of lower-alkyl substituted by halogen groups are e.g. $CFH_2$, $CF_2H$, $CF_3$, $CF_3CH_2$, $CF_3(CH_2)_2$, $(CF_3)_2CH$ or $CF_2H—CF_2$, as well as those groups specifically illustrated by the examples herein below. Particular lower-alkyl substituted by halogen include 2,2,2-trifluoro-ethyl, 2,2,3,3,3-pentafluoro-propyl and 2,2,2-trifluoro-1-methyl-ethyl.

The term "lower-alkyl substituted by hydroxy" denotes a lower-alkyl group as defined above wherein at least one of the hydrogen atoms of the alkyl group is replaced by a hydroxy group. Examples of lower-alkyl substituted by hydroxy include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one or two hydroxy group. Particular lower-alkyl substituted by hydroxy groups include hydroxy-methyl, 2-hydroxy-ethyl, 2-hydroxy-1,1-dimethyl-ethyl and 1-hydroxymethyl-propyl, especially hydroxy-methyl and 1-hydroxymethyl-propyl.

The term "cycloalkyl substituted by hydroxy" denotes a cycloalkyl group as defined above wherein at least one of the hydrogen atoms of the cycloalkyl group is replaced by a hydroxy group. Examples of cycloalkyl substituted by hydroxy include but are not limited to cyclopropyl, cyclobutyl or cyclopentyl substituted by one or more hydroxy groups, in particular with one hydroxy group. A particular cycloalkyl substituted by hydroxy is 2-hydroxy-cyclopentyl.

The term "heterocyclyl substituted by lower-alkyl" denotes a heterocyclyl group as defined above wherein at least one of the hydrogen atoms of the heterocyclyl moiety is replaced by a lower-alkyl group. Examples of heterocyclyl substituted by lower-alkyl include but are not limited to 2-methyl-pyrrolidin-1-yl, 2-ethyl-tetrahydro-furan-3-yl and 3-methyl-oxetan-3-yl. A particular heterocyclyl substituted by lower-alkyl is 3-methyl-oxetan-3-yl.

The term "heteroaryl substituted by lower-alkyl" denotes a heteroaryl group as defined above wherein at least one of the hydrogen atoms of the heteroaryl moiety is replaced by a lower-alkyl group. Examples of heteroaryl substituted by lower-alkyl include but are not limited to 2-methyl-pyridin-1-yl, 2-ethyl-imidazol-3-yl and 1-methyl-1H-pyrazol-4-yl. A particular heterocyclyl substituted by lower-alkyl is 1-methyl-1H-pyrazol-4-yl.

The term "heteroaryl substituted by halogen" denotes a heteroaryl group as defined above wherein at least one of the hydrogen atoms of the heteroaryl moiety is replaced by a halogen group. A particular heterocyclyl substituted by halogen is 5-fluoro-pyridin-2-yl.

"Pharmaceutically acceptable," such as pharmaceutically acceptable carrier, excipient, etc., means pharmacologically acceptable and substantially non-toxic to the subject to which the particular compound is administered.

Compounds of formula I can form pharmaceutically acceptable acid addition salts. Examples of such pharmaceutically acceptable salts are salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I which comprise an acidic group, such as e.g. a COOH group, can further form salts with bases. Examples of such salts are alkaline, earth-alkaline and ammonium salts such as e.g. Na—, K—, Ca—and trimethylammoniumsalt. The term "pharmaceutically acceptable salts" also refers to such salts.

The term "pharmaceutically acceptable esters" embraces derivatives of the compounds of formula I, in which a carboxy group has been converted to an ester. Lower-alkyl, lower-alkyl substituted by hydroxy, lower-alkyl substituted by lower-alkoxy, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aryl-lower-alkyl esters are examples of suitable esters. The methyl, ethyl, propyl, butyl and benzyl esters are preferred esters. The term "pharmaceutically acceptable esters" furthermore embraces compounds of formula I in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Pharmaceutically acceptable," such as pharmaceutically acceptable carrier, excipient, etc., means pharmacologically acceptable and substantially non-toxic to the subject to which the particular compound is administered.

In detail, the present invention provides compounds of formula I

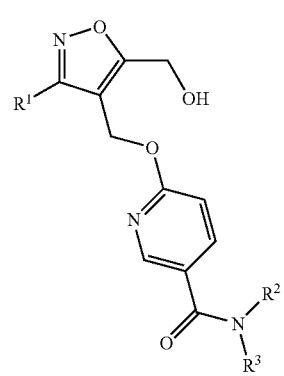

wherein
$R^1$ is lower-alkyl, aryl or heteroaryl,
wherein lower-alkyl is optionally substituted with 1-4 substituents independently selected from the group consisting of halogen, cyano, hydroxy and lower-alkoxy,
and wherein aryl and heteroaryl are optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—NH$_2$, lower-alkyl-CO—N(H, lower-alkyl), lower-alkyl-CO—N(lower-alkyl)$_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, CONH$_2$, CON(H,lower-alkyl), CON(lower-alkyl)$_2$, cycloalkyl, heterocyclyl, aryl, heteroaryl, NH$_2$, N(H, lower-alkyl), N(lower-alkyl)$_2$, hydroxy, lower-alkoxy, phenyloxy, SO$_2$-lower-alkyl, SO$_2$—NH$_2$, SO$_2$—N(H,lower-alkyl) and SO$_2$—N(lower-alkyl)$_2$;
$R^2$ is hydrogen or lower-alkyl;
$R^3$ is lower-alkyl, lower-alkyl substituted by halogen, lower-alkyl substituted by hydroxy, cycloalkyl, cycloalkyl substituted by hydroxy, heterocyclyl, heterocyclyl substituted by lower-alkyl, heteroaryl, heteroaryl substituted by lower-alkyl, (CH$_2$)$_n$—O-lower-alkyl or NR$^4$R$^5$;
or wherein $R^2$ and $R^3$, together with the nitrogen atom to which they are attached, form a heterocyclyl;
n is 1 or 2;
$R^4$ and $R^5$ are each independently selected from hydrogen and lower-alkyl;
and pharmaceutically acceptable salts and esters thereof.

Compounds of formula I are individually preferred and pharmaceutically acceptable salts thereof are individually preferred and pharmaceutically acceptable esters thereof are individually preferred, with the compounds of formula I being particularly preferred.

The compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemate, by asymmetric synthesis or asymmetric chromatography (chromatography with a chiral adsorbens or eluant). The invention embraces all of these forms.

Further, it is to be understood that every embodiment relating to a specific residue $R^1$ to $R^5$ as disclosed herein can be combined with any other embodiment relating to another residue $R^1$ to $R^5$ as disclosed herein.

In certain embodiments, $R^1$ is lower-alkyl, aryl or heteroaryl optionally substituted with one or two halogen. In partiuclar compounds of the present invention are those wherein $R^1$ is n-butyl, phenyl, 4-chloro-phenyl, 4-fluoro-phenyl, 3,4-difluoro-phenyl and pyridine-2-yl, for example those compounds wherein $R^1$ is 4-chloro-phenyl, 4-fluoro-phenyl, pyridine-2-yl and 5-fluoro-pyridin-2-yl.

In certain embodiments, $R^2$ is hydrogen or lower-alkyl, in particular hydrogen or methyl, especially those compounds wherein $R^2$ is hydrogen.

In certain embodiments, $R^3$ is lower-alkyl, lower-alkyl substituted by halogen, lower-alkyl substituted by hydroxy, cycloalkyl, cycloalkyl substituted by hydroxy, heterocyclyl, heterocyclyl substituted by lower-alkyl, heteroaryl, heteroaryl substituted by lower-alkyl, $(CH_2)_n$—O-lower-alkyl or $NR^4R^5$, wherein n is 1 or 2 and wherein $R^4$ and $R^5$ are independently selected from hydrogen and lower-alkyl. In particular compounds of the present invention are those wherein $R^3$ is methyl, isopropyl, tert-butyl, cyclopropylmethyl, 2,2,2-trifluoro-ethyl, 2,2,3,3,3-pentafluoro-propyl, 2,2,2-trifluoro-1-methyl-ethyl, 2-hydroxy-ethyl, 2-hydroxy-1,1-dimethyl-ethyl, 1-hydroxymethyl-propyl, 2-methoxy-ethyl, cyclopropyl, cyclobutyl, 2-hydroxy-cyclopentyl, pyrrolidin-1-yl, tetrahydro-furan-3-yl, tetrahydro-pyran-4-yl, morpholin-4-yl, 3-methyl-oxetan-3-yl, 1-methyl-1H-pyrazol-4-yl or dimethyl-amine, especially those compounds wherein $R^3$ is isopropyl, 1-hydroxymethyl-propyl, cyclopropyl, 2-hydroxy-cyclopentyl or 1-methyl-1H-pyrazol-4-yl.

In certain embodiments, $R^2$ and $R^3$, together with the nitrogen atom to which they are attached, form a heterocyclyl. In particular compounds of the present invention are those wherein $R^2$ and $R^3$, together with the nitrogen atom to which they are attached, form azetidin-1-yl, 1,1-dioxo-thiomorpholin-4-yl or morpholin-4-yl.

In certain embodiments, $R^4$ and $R^5$ are lower-alkyl. In particular compounds of the present invention are those wherein $R^4$ and $R^5$ are methyl.

In particular, compounds are the compounds of formula I described in the examples as individual compounds as well as pharmaceutically acceptable salts and pharmaceutically acceptable esters thereof. Furthermore, the substituents as found in the specific examples described below, individually constitute separate preferred embodiments of the present invention.

Particular compounds of formula I of present invention are those selected from the group consisting of:
6-(5-Hydroxymethyl-3-phenyl-isoxazol-4-ylmethoxy)-N-isopropyl-nicotinamide,
N-(2-Hydroxy-ethyl)-6-(5-hydroxymethyl-3-phenyl-isoxazol-4-ylmethoxy)-nicotinamide,
(1,1-Dioxo-1,6-thiomorpholin-4-yl)-{6-[3-(4-fluoro-phenyl)-5-hydroxymethyl-isoxazol-4-ylmethoxy]-pyridin-3-yl}-methanone,
6-[3-(4-Fluoro-phenyl)-5-hydroxymethyl-isoxazol-4-yl-methoxy]-N-isopropyl-nicotinamide,
6-[3-(4-Fluoro-phenyl)-5-hydroxymethyl-isoxazol-4-yl-methoxy]-N-(tetrahydro-pyran-4-yl)-nicotinamide,
N-Cyclopropylmethyl-6-[3-(4-fluoro-phenyl)-5-hydroxymethyl-isoxazol-4-ylmethoxy]-nicotinamide,
6-[3-(4-Fluoro-phenyl)-5-hydroxymethyl-isoxazol-4-yl-methoxy]-N-(2,2,2-trifluoro-ethyl)-nicotinamide,
N-Cyclopropyl-6-[3-(4-fluoro-phenyl)-5-hydroxymethyl-isoxazol-4-ylmethoxy]-nicotinamide,
6-[3-(4-Fluoro-phenyl)-5-hydroxymethyl-isoxazol-4-yl-methoxy]-N-(2-methoxy-ethyl)-nicotinamide,
6-[3-(4-Fluoro-phenyl)-5-hydroxymethyl-isoxazol-4-yl-methoxy]-N-((1R,2R)-2-hydroxy-cyclopentyl)-nicotinamide,
6-[3-(4-Fluoro-phenyl)-5-hydroxymethyl-isoxazol-4-yl-methoxy]-N-((1S,2S)-2-hydroxy-cyclopentyl)-nicotinamide,
6-[3-(4-Fluoro-phenyl)-5-hydroxymethyl-isoxazol-4-yl-methoxy]-N-(2,2,2-trifluoro-1-methyl-ethyl)-nicotinamide,
6-[3-(4-Fluoro-phenyl)-5-hydroxymethyl-isoxazol-4-yl-methoxy]-N-(2-hydroxy-1,1-dimethyl-ethyl)-nicotinamide,
6-[3-(4-Fluoro-phenyl)-5-hydroxymethyl-isoxazol-4-yl-methoxy]-N-(2,2,3,3,3-pentafluoro-propyl)-nicotinamide,
6-[3-(4-Fluoro-phenyl)-5-hydroxymethyl-isoxazol-4-yl-methoxy]-N-((R)-1-hydroxymethyl-propyl)-nicotinamide,
6-[3-(4-Fluoro-phenyl)-5-hydroxymethyl-isoxazol-4-yl-methoxy]-N-((S)-1-hydroxymethyl-propyl)-nicotinamide,
6-[3-(4-Fluoro-phenyl)-5-hydroxymethyl-isoxazol-4-yl-methoxy]-N-(1-methyl-1H-pyrazol-4-yl)-nicotinamide,
6-[3-(4-Fluoro-phenyl)-5-hydroxymethyl-isoxazol-4-yl-methoxy]-N-(3-methyl-oxetan-3-yl)-nicotinamide,
{6-[3-(4-Chloro-phenyl)-5-hydroxymethyl-isoxazol-4-yl-methoxy]-pyridin-3-yl}-(1,1-dioxo-1,6-thiomorpholin-4-yl)-methanone,
6-[3-(4-Chloro-phenyl)-5-hydroxymethyl-isoxazol-4-yl-methoxy]-N-isopropyl-nicotinamide,
6-[3-(4-Chloro-phenyl)-5-hydroxymethyl-isoxazol-4-yl-methoxy]-N-cyclopropyl-nicotinamide,
6-[3-(4-Chloro-phenyl)-5-hydroxymethyl-isoxazol-4-yl-methoxy]-N-(2,2,2-trifluoro-ethyl)-nicotinamide,
6-[3-(4-Chloro-phenyl)-5-hydroxymethyl-isoxazol-4-yl-methoxy]-N,N-dimethyl-nicotinamide,
6-[3-(4-Chloro-phenyl)-5-hydroxymethyl-isoxazol-4-yl-methoxy]-N-(2-hydroxy-1,1-dimethyl-ethyl)-nicotinamide,
6-[3-(4-Chloro-phenyl)-5-hydroxymethyl-isoxazol-4-yl-methoxy]-N-(1-methyl-1H-pyrazol-4-yl)-nicotinamide,
6-[3-(4-Chloro-phenyl)-5-hydroxymethyl-isoxazol-4-yl-methoxy]-N-((S)-2,2,2-trifluoro-1-methyl-ethyl)-nicotinamide,
6-[3-(4-Chloro-phenyl)-5-hydroxymethyl-isoxazol-4-yl-methoxy]-N-((1R,2R)-2-hydroxy-cyclopentyl)-nicotinamide,
6-[3-(4-Chloro-phenyl)-5-hydroxymethyl-isoxazol-4-yl-methoxy]-N-((1S,2S)-2-hydroxy-cyclopentyl)-nicotinamide,
6-[3-(3,4-Difluoro-phenyl)-5-hydroxymethyl-isoxazol-4-yl-methoxy]-N-isopropyl-nicotinamide,
6-[3-(3,4-Difluoro-phenyl)-5-hydroxymethyl-isoxazol-4-yl-methoxy]-N-(tetrahydro-pyran-4-yl)-nicotinamide,
N-Cyclopropylmethyl-6-[3-(3,4-difluoro-phenyl)-5-hydroxymethyl-isoxazol-4-ylmethoxy]-nicotinamide,
6-[3-(3,4-Difluoro-phenyl)-5-hydroxymethyl-isoxazol-4-yl-methoxy]-N-(2,2,2-trifluoro-ethyl)-nicotinamide,
6-[3-(3,4-Difluoro-phenyl)-5-hydroxymethyl-isoxazol-4-yl-methoxy]-N-(2,2,2-trifluoro-1-methyl-ethyl)-nicotinamide,
N-Cyclopropyl-6-[3-(3,4-difluoro-phenyl)-5-hydroxymethyl-isoxazol-4-ylmethoxy]-nicotinamide, 6-[3-(3,4-Difluoro-phenyl)-5-hydroxymethyl-isoxazol-4-yl-methoxy]-N-(2-hydroxy-1,1-dimethyl-ethyl)-nicotinamide,
6-[3-(3,4-Difluoro-phenyl)-5-hydroxymethyl-isoxazol-4-yl-methoxy]-N-(2,2,3,3,3-pentafluoro-propyl)-nicotinamide,
6-[3-(3,4-Difluoro-phenyl)-5-hydroxymethyl-isoxazol-4-yl-methoxy]-N-(2-methoxy-ethyl)-nicotinamide,
6-[3-(3,4-Difluoro-phenyl)-5-hydroxymethyl-isoxazol-4-yl-methoxy]-N-((R)-1-hydroxymethyl-propyl)-nicotinamide,
6-[3-(3,4-Difluoro-phenyl)-5-hydroxymethyl-isoxazol-4-yl-methoxy]-N-((S)-1-hydroxymethyl-propyl)-nicotinamide,
6-[3-(3,4-Difluoro-phenyl)-5-hydroxymethyl-isoxazol-4-yl-methoxy]-N-(1-methyl-1H-pyrazol-4-yl)-nicotinamide,
N-tert-Butyl-6-[3-(3,4-difluoro-phenyl)-5-hydroxymethyl-isoxazol-4-ylmethoxy]-nicotinamide,
6-[3-(3,4-Difluoro-phenyl)-5-hydroxymethyl-isoxazol-4-yl-methoxy]-N-morpholin-4-yl-nicotinamide,
6-[3-(3,4-Difluoro-phenyl)-5-hydroxymethyl-isoxazol-4-yl-methoxy]-N-pyrrolidin-1-yl-nicotinamide,
(1,1-Dioxo-1,6-thiomorpholin-4-yl)-[6-(5-hydroxymethyl-3-pyridin-2-yl-isoxazol-4-ylmethoxy)-pyridin-3-yl]-methanone,
6-(5-Hydroxymethyl-3-pyridin-2-yl-isoxazol-4-yl-methoxy)-N-isopropyl-nicotinamide,
6-(5-Hydroxymethyl-3-pyridin-2-yl-isoxazol-4-yl-methoxy)-N-(tetrahydro-furan-3-yl)-nicotinamide,
6-(5-Hydroxymethyl-3-pyridin-2-yl-isoxazol-4-yl-methoxy)-nicotinic acid N',N'-dimethyl-hydrazide,
6-(5-Hydroxymethyl-3-pyridin-2-yl-isoxazol-4-yl-methoxy)-N-(tetrahydro-pyran-4-yl)-nicotinamide,
6-(5-Hydroxymethyl-3-pyridin-2-yl-isoxazol-4-yl-methoxy)-N-morpholin-4-yl-nicotinamide,
6-(3-Butyl-5-hydroxymethyl-isoxazol-4-ylmethoxy)-N-isopropyl-nicotinamide,
6-(3-Butyl-5-hydroxymethyl-isoxazol-4-ylmethoxy)-N-(3-methyl-oxetan-3-yl)-nicotinamide,
6-(3-Butyl-5-hydroxymethyl-isoxazol-4-ylmethoxy)-N-(2,2,2-trifluoro-ethyl)-nicotinamide,
6-(3-Butyl-5-hydroxymethyl-isoxazol-4-ylmethoxy)-N-cyclobutyl-nicotinamide,
Azetidin-1-yl-[6-(3-butyl-5-hydroxymethyl-isoxazol-4-yl-methoxy)-pyridin-3-yl]-methanone,
[6-(5-Hydroxymethyl-3-pyridin-2-yl-isoxazol-4-yl-methoxy)-pyridin-3-yl]-morpholin-4-yl-methanone,
[6-(3-Butyl-5-hydroxymethyl-isoxazol-4-ylmethoxy)-pyridin-3-yl]-(1,1-dioxo-thiomorpholin-4-yl)-methanone, and
(1,1-Dioxo-1,6-thiomorpholin-4-yl)-{6-[3-(5-fluoro-pyridin-2-yl)-5-hydroxymethyl-isoxazol-4-ylmethoxy]-pyridin-3-yl}-methanone,
and pharmaceutically acceptable salts and esters thereof.

Other compounds of formula I of present invention are those selected from the group consisting of:
6-(5-Hydroxymethyl-3-phenyl-isoxazol-4-ylmethoxy)-N-isopropyl-nicotinamide,
N-(2-Hydroxy-ethyl)-6-(5-hydroxymethyl-3-phenyl-isoxazol-4-ylmethoxy)-nicotinamide,
(1,1-Dioxo-1,6-thiomorpholin-4-yl)-{6-[3-(4-fluoro-phenyl)-5-hydroxymethyl-isoxazol-4-ylmethoxy]-pyridin-3-yl}-methanone,
6-[3-(4-Fluoro-phenyl)-5-hydroxymethyl-isoxazol-4-yl-methoxy]-N-isopropyl-nicotinamide,
6-[3-(4-Fluoro-phenyl)-5-hydroxymethyl-isoxazol-4-yl-methoxy]-N-(tetrahydro-pyran-4-yl)-nicotinamide,
N-Cyclopropylmethyl-6-[3-(4-fluoro-phenyl)-5-hydroxymethyl-isoxazol-4-ylmethoxy]-nicotinamide,
6-[3-(4-Fluoro-phenyl)-5-hydroxymethyl-isoxazol-4-yl-methoxy]-N-(2,2,2-trifluoro-ethyl)-nicotinamide,
N-Cyclopropyl-6-[3-(4-fluoro-phenyl)-5-hydroxymethyl-isoxazol-4-ylmethoxy]-nicotinamide,
6-[3-(4-Fluoro-phenyl)-5-hydroxymethyl-isoxazol-4-yl-methoxy]-N-(2-methoxy-ethyl)-nicotinamide,
6-[3-(4-Fluoro-phenyl)-5-hydroxymethyl-isoxazol-4-yl-methoxy]-N-((1R,2R)-2-hydroxy-cyclopentyl)-nicotinamide,
6-[3-(4-Fluoro-phenyl)-5-hydroxymethyl-isoxazol-4-yl-methoxy]-N-((1S,2S)-2-hydroxy-cyclopentyl)-nicotinamide,
6-[3-(4-Fluoro-phenyl)-5-hydroxymethyl-isoxazol-4-yl-methoxy]-N-(2,2,2-trifluoro-1-methyl-ethyl)-nicotinamide,
6-[3-(4-Fluoro-phenyl)-5-hydroxymethyl-isoxazol-4-yl-methoxy]-N-(2-hydroxy-1,1-dimethyl-ethyl)-nicotinamide,
6-[3-(4-Fluoro-phenyl)-5-hydroxymethyl-isoxazol-4-yl-methoxy]-N-(2,2,3,3,3-pentafluoro-propyl)-nicotinamide,
6-[3-(4-Fluoro-phenyl)-5-hydroxymethyl-isoxazol-4-yl-methoxy]-N-((R)-1-hydroxymethyl-propyl)-nicotinamide,
6-[3-(4-Fluoro-phenyl)-5-hydroxymethyl-isoxazol-4-yl-methoxy]-N-((S)-1-hydroxymethyl-propyl)-nicotinamide,
6-[3-(4-Fluoro-phenyl)-5-hydroxymethyl-isoxazol-4-yl-methoxy]-N-(1-methyl-1H-pyrazol-4-yl)-nicotinamide,
6-[3-(4-Fluoro-phenyl)-5-hydroxymethyl-isoxazol-4-yl-methoxy]-N-(3-methyl-oxetan-3-yl)-nicotinamide,
{6-[3-(4-Chloro-phenyl)-5-hydroxymethyl-isoxazol-4-yl-methoxy]-pyridin-3-yl}-(1,1-dioxo-1,6-thiomorpholin-4-yl)-methanone,
6-[3-(4-Chloro-phenyl)-5-hydroxymethyl-isoxazol-4-yl-methoxy]-N-isopropyl-nicotinamide,
6-[3-(4-Chloro-phenyl)-5-hydroxymethyl-isoxazol-4-yl-methoxy]-N-cyclopropyl-nicotinamide,
6-[3-(4-Chloro-phenyl)-5-hydroxymethyl-isoxazol-4-yl-methoxy]-N-(2,2,2-trifluoro-ethyl)-nicotinamide,
6-[3-(4-Chloro-phenyl)-5-hydroxymethyl-isoxazol-4-yl-methoxy]-N,N-dimethyl-nicotinamide,
6-[3-(4-Chloro-phenyl)-5-hydroxymethyl-isoxazol-4-yl-methoxy]-N-(2-hydroxy-1,1-dimethyl-ethyl)-nicotinamide,
6-[3-(4-Chloro-phenyl)-5-hydroxymethyl-isoxazol-4-yl-methoxy]-N-(1-methyl-1H-pyrazol-4-yl)-nicotinamide,
6-[3-(4-Chloro-phenyl)-5-hydroxymethyl-isoxazol-4-yl-methoxy]-N-((S)-2,2,2-trifluoro-1-methyl-ethyl)-nicotinamide,
6-[3-(4-Chloro-phenyl)-5-hydroxymethyl-isoxazol-4-yl-methoxy]-N-((1R,2R)-2-hydroxy-cyclopentyl)-nicotinamide,
6-[3-(4-Chloro-phenyl)-5-hydroxymethyl-isoxazol-4-yl-methoxy]-N-((1S,2S)-2-hydroxy-cyclopentyl)-nicotinamide,
6-[3-(3,4-Difluoro-phenyl)-5-hydroxymethyl-isoxazol-4-yl-methoxy]-N-isopropyl-nicotinamide,
6-[3-(3,4-Difluoro-phenyl)-5-hydroxymethyl-isoxazol-4-yl-methoxy]-N-(tetrahydro-pyran-4-yl)-nicotinamide,
N-Cyclopropylmethyl-6-[3-(3,4-difluoro-phenyl)-5-hydroxymethyl-isoxazol-4-ylmethoxy]-nicotinamide,
6-[3-(3,4-Difluoro-phenyl)-5-hydroxymethyl-isoxazol-4-yl-methoxy]-N-(2,2,2-trifluoro-ethyl)-nicotinamide, 6-[3-(3,4-Difluoro-phenyl)-5-hydroxymethyl-isoxazol-4-yl-methoxy]-N-(2,2,2-trifluoro-1-methyl-ethyl)-nicotinamide,
N-Cyclopropyl-6-[3-(3,4-difluoro-phenyl)-5-hydroxymethyl-isoxazol-4-ylmethoxy]-nicotinamide,
6-[3-(3,4-Difluoro-phenyl)-5-hydroxymethyl-isoxazol-4-yl-methoxy]-N-(2-hydroxy-1,1-dimethyl-ethyl)-nicotinamide,
6-[3-(3,4-Difluoro-phenyl)-5-hydroxymethyl-isoxazol-4-yl-methoxy]-N-(2,2,3,3,3-pentafluoro-propyl)-nicotinamide,
6-[3-(3,4-Difluoro-phenyl)-5-hydroxymethyl-isoxazol-4-yl-methoxy]-N-(2-methoxy-ethyl)-nicotinamide,
6-[3-(3,4-Difluoro-phenyl)-5-hydroxymethyl-isoxazol-4-yl-methoxy]-N-((R)-1-hydroxymethyl-propyl)-nicotinamide,
6-[3-(3,4-Difluoro-phenyl)-5-hydroxymethyl-isoxazol-4-yl-methoxy]-N-((S)-1-hydroxymethyl-propyl)-nicotinamide,
6-[3-(3,4-Difluoro-phenyl)-5-hydroxymethyl-isoxazol-4-yl-methoxy]-N-(1-methyl-1H-pyrazol-4-yl)-nicotinamide,
N-tert-Butyl-6-[3-(3,4-difluoro-phenyl)-5-hydroxymethyl-isoxazol-4-ylmethoxy]-nicotinamide,
6-[3-(3,4-Difluoro-phenyl)-5-hydroxymethyl-isoxazol-4-yl-methoxy]-N-morpholin-4-yl-nicotinamide,
6-[3-(3,4-Difluoro-phenyl)-5-hydroxymethyl-isoxazol-4-yl-methoxy]-N-pyrrolidin-1-yl-nicotinamide,
(1,1-Dioxo-1,6-thiomorpholin-4-yl)-[6-(5-hydroxymethyl-3-pyridin-2-yl-isoxazol-4-ylmethoxy)-pyridin-3-yl]-methanone,
6-(5-Hydroxymethyl-3-pyridin-2-yl-isoxazol-4-yl-methoxy)-N-isopropyl-nicotinamide,
6-(5-Hydroxymethyl-3-pyridin-2-yl-isoxazol-4-yl-methoxy)-N-(tetrahydro-furan-3-yl)-nicotinamide,
6-(5-Hydroxymethyl-3-pyridin-2-yl-isoxazol-4-yl-methoxy)-nicotinic acid N',N'-dimethyl-hydrazide,
6-(5-Hydroxymethyl-3-pyridin-2-yl-isoxazol-4-yl-methoxy)-N-(tetrahydro-pyran-4-yl)-nicotinamide,
6-(5-Hydroxymethyl-3-pyridin-2-yl-isoxazol-4-yl-methoxy)-N-morpholin-4-yl-nicotinamide,
6-(3-Butyl-5-hydroxymethyl-isoxazol-4-ylmethoxy)-N-isopropyl-nicotinamide,
6-(3-Butyl-5-hydroxymethyl-isoxazol-4-ylmethoxy)-N-(3-methyl-oxetan-3-yl)-nicotinamide,
6-(3-Butyl-5-hydroxymethyl-isoxazol-4-ylmethoxy)-N-(2,2,2-trifluoro-ethyl)-nicotinamide,
6-(3-Butyl-5-hydroxymethyl-isoxazol-4-ylmethoxy)-N-cyclobutyl-nicotinamide, and
Azetidin-1-yl-[6-(3-butyl-5-hydroxymethyl-isoxazol-4-yl-methoxy)-pyridin-3-yl]-methanone,
and pharmaceutically acceptable salts and esters thereof.

Still other compounds of formula I of present invention are those selected from the group consisting of:
6-[3-(4-Chloro-phenyl)-5-hydroxymethyl-isoxazol-4-yl-methoxy]-N-isopropyl-nicotinamide,
6-[3-(4-Fluoro-phenyl)-5-hydroxymethyl-isoxazol-4-yl-methoxy]-N-((S)-1-hydroxymethyl-propyl)-nicotinamide,
6-[3-(4-Chloro-phenyl)-5-hydroxymethyl-isoxazol-4-yl-methoxy]-N-((1R,2R)-2-hydroxy-cyclopentyl)-nicotinamide,
6-[3-(4-Chloro-phenyl)-5-hydroxymethyl-isoxazol-4-yl-methoxy]-N-((1S,2S)-2-hydroxy-cyclopentyl)-nicotinamide,
6-[3-(4-Chloro-phenyl)-5-hydroxymethyl-isoxazol-4-yl-methoxy]-N-(1-methyl-1H-pyrazol-4-yl)-nicotinamide,
6-(5-Hydroxymethyl-3-pyridin-2-yl-isoxazol-4-yl-methoxy)-N-isopropyl-nicotinamide,
6-[3-(4-Fluoro-phenyl)-5-hydroxymethyl-isoxazol-4-yl-methoxy]-N-(1-methyl-1H-pyrazol-4-yl)-nicotinamide, and
6-[3-(4-Chloro-phenyl)-5-hydroxymethyl-isoxazol-4-yl-methoxy]-N-cyclopropyl-nicotinamide,
and pharmaceutically acceptable salts and esters thereof.

The invention further relates to a process for the manufacture of compounds of formula I as defined above, which process comprises:
a) reacting a compound of formula II with $NHR^2R^3$:

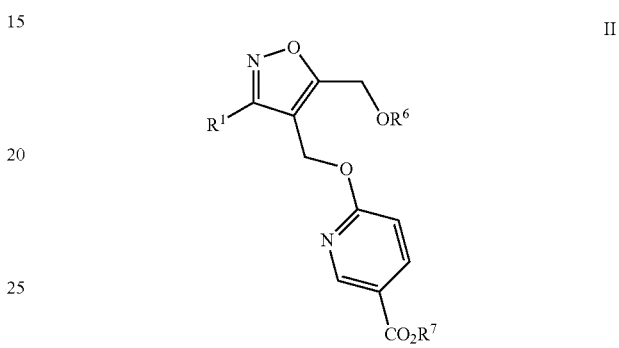

or
b) enzymatic biotransformation of a compound of formula III:

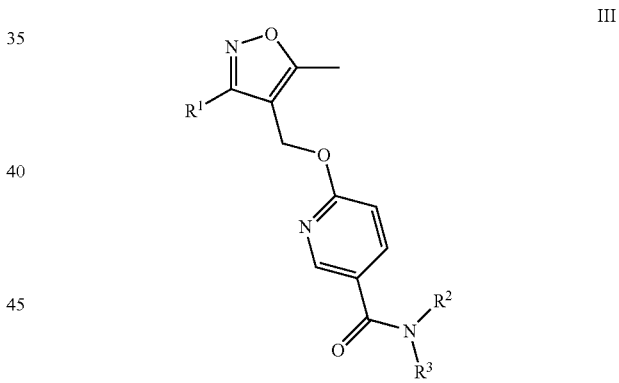

wherein $R^1$, $R^2$ and $R^3$ are as defined above, $R^6$ is hydrogen or tert-butyldimethylsilyl and $R^7$ is hydrogen or lower-alkyl.

The reaction of a compound of formula II, wherein $R^6$ is hydrogen and $R^7$ is lower-alkyl, with $NHR^2R^3$ to give a compound of formula I can be carried out under conditions as described in the examples or under conditions well known to the person skilled in the art. For example, the reaction can be performed in the presence of trimethylaluminium in a suitable solvent like dioxane at elevated temperatures e.g. at 85-95° C. Alternatively, the reaction can be performed in the presence of 1,5,7-triazabicyclo[4.4.0]dec-5-ene in a suitable solvent like toluene at elevated temperatures e.g. at 50° C.

The reaction of a compound of formula II, wherein $R^6$ and $R^7$ are hydrogen, with $NHR^2R^3$ to give a compound of formula I can be carried out under conditions as described in the examples or under conditions well known to the person skilled in the art. For example, the reaction can be performed in the presence of Hünigs Base (N,N-diisopropylethylamine)

and O-(benzotriazol-1-yl)-N,N,N',N'-tetramethyluronium tetrafluoroborate in a suitable solvent like dimethylformamid at room temperature. Alternatively, the reaction can be performed in the presence of 1,1'-carbonyldiimidazole in a suitable solvent like dimethylformamid at elevated temperatures e.g. at 80° C. Furthermore, the reaction can be performed in the presence of 1-ethyl-3-(3-dimethylaminopropyl) carbodiimide hydrochloride, N1-hydroxybenzotriazole and Hünigs Base (N,N-diisopropylethylamine) in a suitable solvent like dichloromethane at room temperature.

The reaction of a compound of formula II, wherein $R^6$ is tert-butyldimethylsilyl and $R^7$ is lower-alkyl, with $NHR^2R^3$ to a compound of formula I can be carried out under conditions as described in the examples or under conditions well known to the person skilled in the art. For example, the reaction can be performed in the presence of trimethylaluminium in a suitable solvent like dioxane at elevated temperatures e.g. at 85-95° C. followed by a reaction with tetra-n-butylammonium fluoride in a suitable solvent like tetrahydrofurane at room temperature.

The enzymatic biotransformation of a compound of formula III to a compound of formula I can be carried out under conditions as described in the examples or under conditions well known to the person skilled in the art. For example, the reaction can be performed in the presence of Cytochrome P450 3A4 and nicotinamide adenine dinucleotide phosphate in a suitable buffer at room temperature.

The present invention also relates to compounds of formula I as defined above, when prepared by a process as described above.

The present compounds of formula I and their pharmaceutically acceptable salts can be prepared by a process comprising the steps of:

a) reacting a compound of formula 1

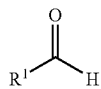

1 with hydroxylamine hydrochloride in a suitable solvent, such as ethanol and water in the presence of a base, such as aqueous sodium hydroxide to give a compound of formula 2:

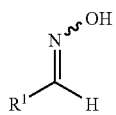

2 b) reacting the compound of formula 2 with a chlorinating agent such as N-chlorosuccinimide in a suitable solvent, such as DMF to give a compound of formula 3:

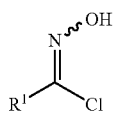

3 c) and then either reacting the compound of formula 3 with a compound of formula 4:

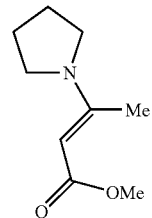

4 in the presence of a suitable base, such as triethylamine, in a suitable solvent, such as chloroform, to give a compound of formula 6:

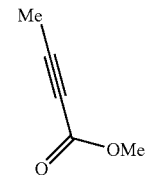

6 d) or alternatively reacting the compound of formula 3 with a compound of formula 5:

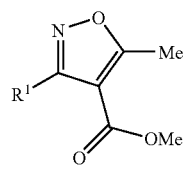

5 in the presence of a suitable base, such as triethylamine, in a suitable solvent, such as diethylether, to give a compound of formula 6;

e) and then reacting the compound of formula 6 with benzaldehyde in the presence of a base such as sodium ethoxide in suitable solvent such as ethanol under reflux to give a compound of formula 7:

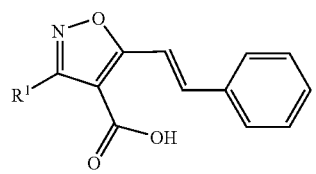

7 f) followed by reacting a compound of formula 7 with a reducing agent, such as lithiumaluminiumhydride or ethylchloroformate in the presence of sodiumborohydride and a suitable base such as triethylamine in a suitable solvent such as THF or water to give a compound of formula 8:

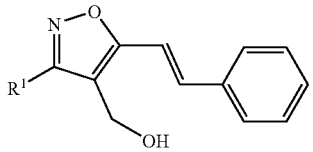

8 g) followed by reacting a compound of formula 8 with a compound such as 9:

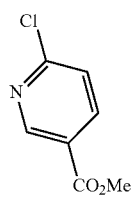

9 in the presence of a suitable base, such as sodium hydride, in a suitable solvent, such as THF to give a compound of formula 10:

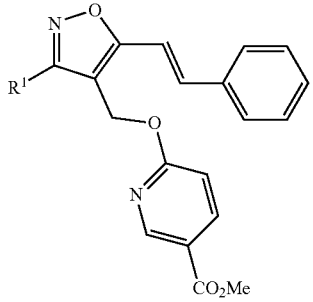

10 h) followed by reacting a compound of formula 10 with an oxidizing agent such as Osmium(VIII)-oxide and sodium metaperiodate in the presence of benzyltriethylammonium chloride in the presence of a suitable solvent such as tert-butanol, dioxane and water to give a compound of formula 11:

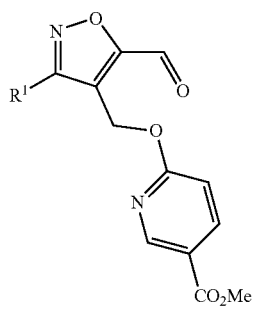

11 i) followed by reacting a compound of formula 11 with a reducing agent, such as sodiumborohydride in a suitable solvent such as methanol to give a compound of formula II-A:

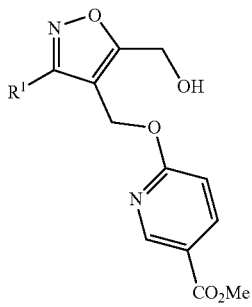

II-A j) Alternatively, a compound of formula 10 can be reacted with AD Mix-α with methanesulfonamide in a suitable solvent such as tert-butanol and water to give a compound of formula 12:

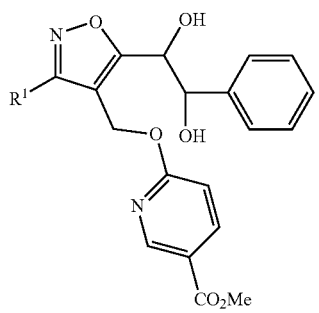

12 k) followed by reacting a compound of formula 12 with lead tetraacetate in a suitable solvent such as benzene and then reacted with a reducing agent such as sodiumborohydride in a suitable solvent such as methanol to give a compound of formula II-A.

l) Alternatively, a compound of formula 8 can be reacted with a compound of formula 13:

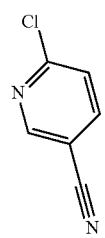

13 in the presence of a suitable base, such as sodium hydride, in a suitable solvent such as DMF to give a compound of formula 14:

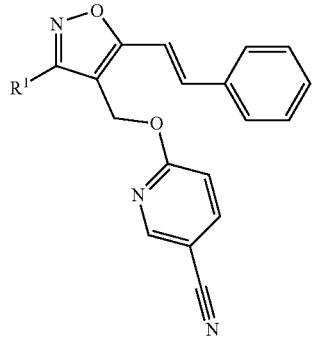

14 m) followed by reacting a compound of formula 14 with an oxidizing agent such as Osmium(VIII)-oxide and sodium metaperiodate in the presence of benzyltriethylammonium chloride in the presence of a suitable solvent such as tert-butanol, dioxane and water to give a compound of formula 15:

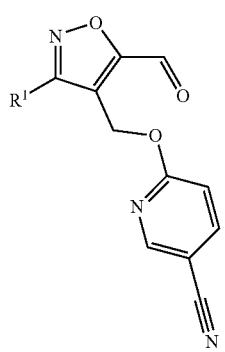

15 n) followed by reacting a compound of formula 15 with a reducing agent, such as sodiumborohydride in a suitable solvent such as methanol to give a compound of formula 16:

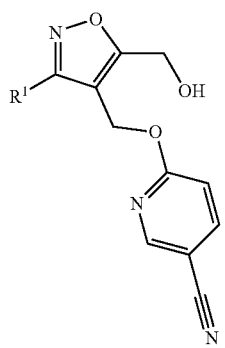

16 o) followed by reacting a compound of formula 16 with a base such as sodium ethoxide in suitable solvent such as ethanol under reflux to give a compound of formula II-B:

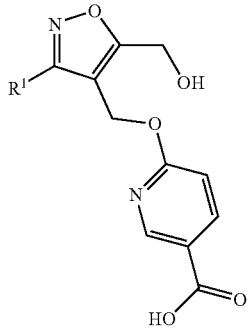

II-B p) Alternatively, a compound of formula 17:

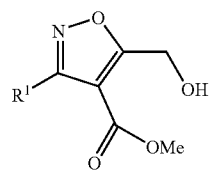

17 can be reacted with a suitable protecting group, such as tert-butyldimethylchlorosilane in the presence of a suitable base such as imidazole in a suitable solvent such as DMF to give a compound of formula 18:

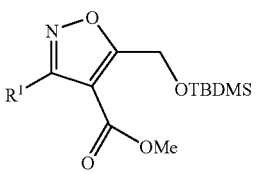

18 q) followed by reacting a compound of formula 18 in the presence of a reducing agent such as lithiumborohydride in a suitable solvent such as THF give a compound of formula 19:

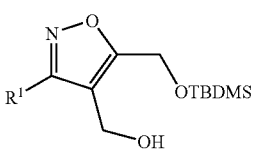

19 r) followed by reacting a compound of formula 19 with a compound such as 9 in the presence of a suitable base, such as sodium hydride, in a suitable solvent, such as THF to give a compound of formula II-C:

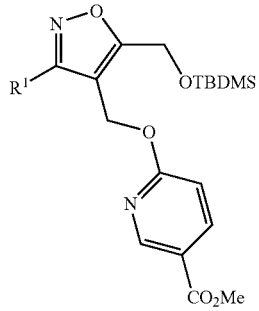

II-C

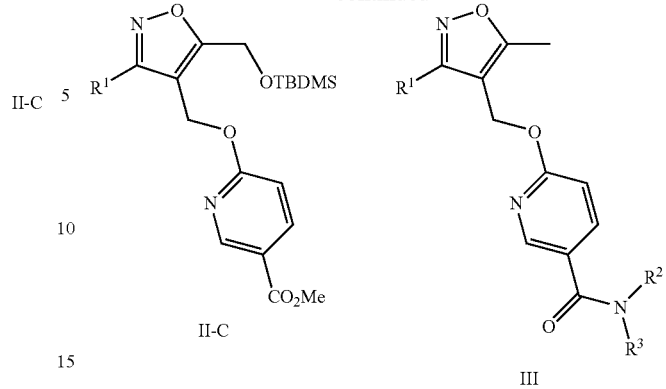

II-C

In accordance with Scheme 1, compounds of formula I can be prepared following standard methods.

Scheme 1

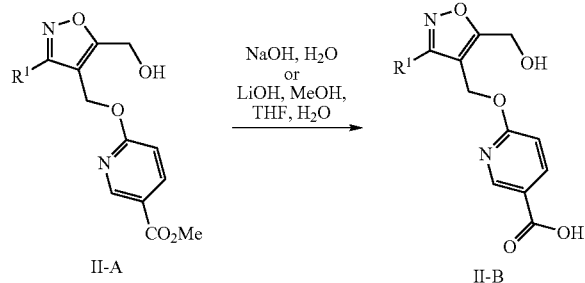

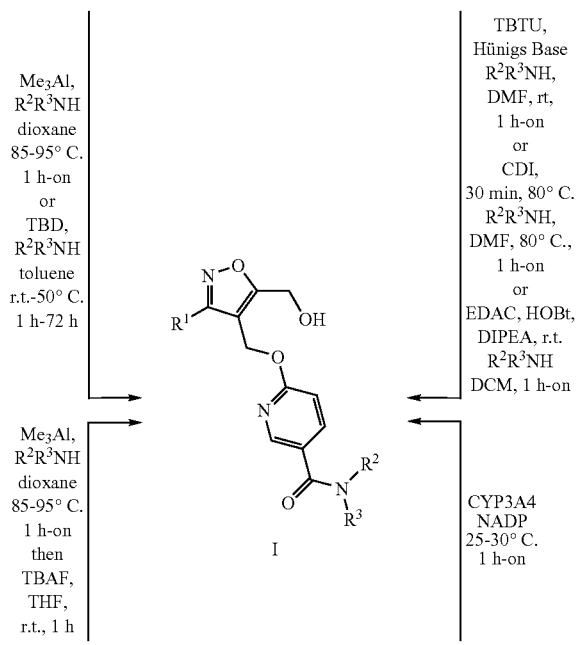

CDI=1,1'-carbonyldiimidazole
CYP3A4=Cytochrome P450 3A4
DCM=dichloromethane
DMAP=N,N-dimethylamino-4-pyridine
DIPEA=N,N-diisopropylethylamine (Hünigs Base)
DMF=dimethylformamid
DMSO=dimethylsulfoxide
EDAC=1-ethyl-3-(3-dimethylaminopropyl) carbodiimide hydrochloride
EtOH=ethanol
HOBt=N1-hydroxybenzotriazole
$Me_3Al$=trimethylaluminium
NADP=nicotinamide adenine dinucleotide phosphate
on=overnight
rt=room temperature
TBAF=tetra-n-butylammonium fluoride
TBD=1,5,7-triazabicyclo[4.4.0]dec-5-ene
TBTU=O-(benzotriazol-1-yl)-N,N,N',N'-tetramethyluronium tetrafluoroborate
TBDMS=tert-butyldimethylsilyl The corresponding salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula I into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula I as well as all intermediate products can be prepared according to analogous methods or according to the methods set forth above. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

As described above, the novel compounds of the present invention and their pharmaceutically acceptable salts and esters possess valuable pharmacological properties and are ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another embodiment, the invention relates to a method for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also relates to the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

In one embodiment the invention provides a treatment or prevention of cognitive disorders, Alzheimer's disease, schizophrenia, positive, negative and/or cognitive symptoms associated with schizophrenia, Down syndrome, and neurofibromatosis type I.

In one embodiment the invention provides a treatment or prevention of Alzheimer's disease.

In one embodiment the invention provides a treatment or prevention of Down syndrome.

In one embodiment the invention provides a treatment or prevention of neurofibromatosis type I.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition $\alpha1\beta3\gamma2$, $\alpha2\beta3\gamma2$, $\alpha3\beta3\gamma2$ and $\alpha5\beta3\gamma2$.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for $\alpha1$, $\alpha2$, $\alpha3$ subunits and 0.5 nM for $\alpha5$ subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values were calculated using Excel-Fit (Microsoft) and are the means of two determinations.

The compounds of the accompanying examples were tested in the above described assay, and the preferred compounds were found to possess a $K_i$ value for displacement of [$^3$H]flumazenil from $\alpha5$ subunits of the rat GABA A receptor of 100 nM or less. Most preferred are compounds with a $K_i$ (nM)<35. In a preferred embodiment the compounds of the invention are binding selective for the $\alpha5$ subunit relative to the $\alpha1$, $\alpha2$ and $\alpha3$ subunit.

Representative test results, obtained by the above described assay measuring binding affinity to HEK293 cells expressing human (h) receptors, are shown in table 1 below.

TABLE 1

| Ex. | $hK_i$ GABA A $\alpha5$ [nM] |
|---|---|
| 1 | 2.2 |
| 2 | 1.6 |
| 3 | 8.6 |
| 4 | 1.1 |
| 5 | 1.3 |
| 6 | 1.7 |
| 7 | 1.3 |
| 8 | 1.7 |
| 9 | 4.1 |
| 10 | 1.6 |
| 11 | 1.4 |
| 12 | 10.1 |
| 13 | 3.4 |
| 14 | 3.5 |
| 15 | 0.6 |
| 16 | 0.9 |
| 17 | 1.8 |
| 18 | 3.5 |
| 19 | 0.4 |
| 20 | 1 |
| 21 | 2 |
| 22 | 43.4 |
| 23 | 3.9 |

TABLE 1-continued

| Ex. | $hK_i$ GABA A $\alpha5$ [nM] |
|---|---|
| 24 | 0.7 |
| 25 | 1.7 |
| 26 | 1.2 |
| 27 | 0.6 |
| 28 | 1.5 |
| 29 | 2 |
| 30 | 4 |
| 31 | 2.7 |
| 32 | 1.8 |
| 33 | 3.1 |
| 34 | 13.6 |
| 35 | 6.8 |
| 36 | 7.7 |
| 37 | 4.4 |
| 38 | 1.3 |
| 39 | 2.1 |
| 40 | 11.8 |
| 41 | 1.1 |
| 42 | 4.5 |
| 43 | 10.8 |
| 44 | 0.7 |
| 45 | 1.8 |
| 46 | 2.5 |
| 47 | 1.1 |
| 48 | 1.7 |
| 49 | 16 |
| 50 | 8.7 |
| 51 | 10.2 |
| 52 | 13.7 |
| 53 | 51.3 |
| 54 | 67.2 |
| 55 | 50.5 |
| 56 | 13.5 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 0.1 to 1000 mg per person of a compound of formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

TABLE 2

| possible tablet composition | |
|---|---|
| Ingredient | mg/tablet |
| Active substance | 5 |
| Lactose | 45 |
| Corn starch | 15 |
| Microcrystalline cellulose | 34 |
| Magnesium stearate | 1 |
| Tablet weight | 100 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

EXAMPLE B

Capsules of the following composition are manufactured:

TABLE 3

| possible capsule composition | |
|---|---|
| Ingredient | mg/capsule |
| Active substance | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

TABLE 4

| possible suppository composition | |
|---|---|
| Ingredient | mg/supp. |
| Active substance | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1 to 53 are provided for illustration of the invention. They should not be considered as limiting the scope of the invention, but merely as being representative thereof.

EXAMPLE 1

6-(5-Hydroxymethyl-3-phenyl-isoxazol-4-yl-methoxy)-N-isopropyl-nicotinamide

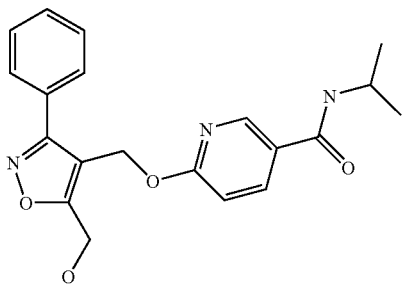

a) 5-(tert-Butyl-dimethyl-silanyloxymethyl)-3-phenyl-isoxazole-4-carboxylic acid ethyl ester Prepared according to *Synthesis* 1984, 868-870. To a solution of 5-hydroxymethyl-3-phenyl-isoxazole-4-carboxylic acid ethyl ester (10.0 g, 40 mmol) in DMF (100 mL) was added tert-butyldimethylchlorosilane (5.49 g, 36 mmol) and imidazole (2.75 g, 40 mmol). The reaction mixture was stirred overnight, then the solvent was evaporated and the residue was partitioned (diethylether/water). The organic phase was then dried over sodium sulfate, filtered and concentrated. After chromatographic purification (silica, heptane:ethyl acetate=100:0 to 9:1) the title compound was obtained as a colorless oil (12.2 g, 84%). MS: m/e=362.3 [M+H]$^+$.

b) [5-(tert-Butyl-dimethyl-silanyloxymethyl)-3-phenyl-isoxazol-4-yl]-methanol 5-(tert-Butyl-dimethyl-silanyloxymethyl)-3-phenyl-isoxazole-4-carboxylic acid ethyl ester (12.2 g, 34 mmol) was dissolved in THF (200 mL), lithium borohydride (1.47 g, 67 mmol) was added and the reaction mixture was heated under reflux overnight. After cooling to room temperature aqueous saturated Seignette salt solution was added and the mixture was stirred for 1 h. After extractive workup (ethyl acetate/diethylether) the organic phase was dried over sodium sulfate, filtered and concentrated. Chromatographic purification (silica, heptane:ethyl acetate=100:0 to 85:15) afforded the title compound as a light yellow oil (4.4 g, 41%). MS: m/e=320.4 [M+H]$^+$.

c) 6-[5-(tert-Butyl-dimethyl-silanyloxymethyl)-3-phenyl-isoxazol-4-ylmethoxy]-nicotinic acid methyl ester A solution of [5-(tert-butyl-dimethyl-silanyloxymethyl)-3-phenyl-isoxazol-4-yl]-methanol (4.09 g, 12.8 mmol) in THF (20 mL) was added dropwise to a suspension of sodium hydride (0.73 g of a 55% dispersion in mineral oil, 16.7 mmol). After stirring for 30 min at room temperature, the mixture was cooled in an ice bath and a solution of methyl 6-chloronicotinate (2.20 g, 12.8 mmol) in THF (20 mL) was added dropwise. The ice bath was removed and the reaction mixture was allowed to reach room temperature and was stirred for 2 h. After quenching with water and extractive workup (ethyl acetate/water) the organic phase was dried over sodium sulfate, filtered and concentrated. Chromatographic purification (silica, heptane:ethyl acetate=100:0 to 8:2) afforded the title compound as a colorless oil (2.76 g, 47%). MS: m/e=455.4 [M+H]$^+$.

d) 6-(5-Hydroxymethyl-3-phenyl-isoxazol-4-ylmethoxy)-N-isopropyl-nicotinamide Trimethylaluminum (4.4 mL of a 2M solution in hexane, 8.8 mmol) was slowly added to a solution of isopropylamine (0.76 mL, 8.9 mmol) in dioxane (7.5 mL) and stirred at room temperature for 1 h. Then a solution of 6-[5-(tert-butyl-dimethyl-silanyloxymethyl)-3-phenyl-isoxazol-4-ylmethoxy]-nicotinic acid methyl ester (1.0 g, 2.2 mmol) in dioxane (7.5 mL) was added dropwise. The mixture was stirred at 90° C. for 2 h. After cooling to room temperature and extractive workup (ethyl acetate/aqueous saturated Seignette salt solution) the organic phase was dried (Na$_2$SO$_4$) and filtered over a silica pad. The solvent was evaporated to furnish an intermediate which was dissolved in a tetrabutylammonium fluoride solution (2 mL of a 1M in THF). After 1 h the reaction mixture was extractively worked up (ethyl acetate/aqueous saturated citric acid). The organic phase was dried over sodium sulfate, filtred and concentrated and then purified by HPLC (Chiralpak AD, heptane/ethanol) to afford the title compound as a colorless oil (0.15 g, 18%). MS: m/e=368.3 [M+H]$^+$.

EXAMPLE 2

N-(2-Hydroxy-ethyl)-6-(5-hydroxymethyl-3-phenyl-isoxazol-4-ylmethoxy)-nicotinamide

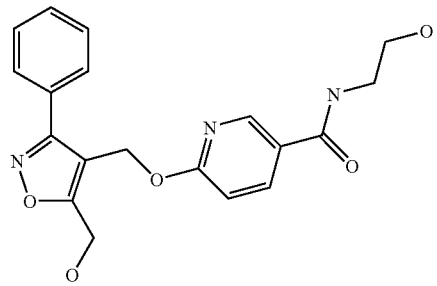

a) 3-Phenyl-5-((E)-styryl)-isoxazole-4-carboxylic acid

To a solution of 5-methyl-3-phenyl-isoxazole-4-carboxylic acid ethyl ester (2.28 g, 10 mmol) and benzaldehyde (1.01 mL, 10 mmol) in ethanol (15 mL) was added sodium ethoxide (0.74 g, 11 mmol) and the reaction mixture was heated under reflux for 10 min. Aqueous hydrochloric acid (1 M, 12 mL) was then added and after stirring for 15 min the precipitate was filtered and dried to afford the title compound as a light brown solid (2.0 g, 71%). MS: m/e=292.1 [M+H]$^+$.

b) [3-Phenyl-5-((E)-styryl)-isoxazol-4-yl]-methanol

To a stirred solution of 3-phenyl-5-((E)-styryl)-isoxazole-4-carboxylic acid (2.0 g, 6.9 mmol) in THF (50 mL) was added triethylamine (0.95 mL, 6.9 mmol). Then at room temperature ethyl chloroformate (0.65 mL, 6.9 mmol) was added dropwise. After 30 min the precipitated salt was filtered and washed with a small amount of THF. The filtrate was added to a solution of sodium borohydride (0.65 g, 17.1 mmol) in water (20 mL) at 5° C. After stirring for 1 h at 5° C. aqueous sodium hydroxide (2 M, 40 mL) was added. Extraction with ethyl acetate, drying over sodium sulfate, filtering and concentration afforded the title compound as a white solid (1.89 g, 99%). MS: m/e=278.1 [M+H]$^+$.

c) 6-[3-Phenyl-5-((E)-styryl)-isoxazol-4-ylmethoxy]-nicotinic acid methyl ester A stirred solution of [3-phenyl-5-((E)-styryl)-isoxazol-4-yl]-methanol (1.50 g, 5.4 mmol) in THF (50 mL) was cooled in an ice bath. Sodium hydride (0.28 g of a 55% dispersion in mineral oil, 6.4 mmol) was added and the mixture was stirred for 30 min whilst allowing to warm to room temperature. To the resulting suspension was added methyl 6-chloropyridine-3-carboxylate (0.93 g, 5.4 mmol). After stirring for 2 h the reaction mixture was quenched with aqueous saturated sodium bicarbonate solution (20 mL). Evaporation of the organic solvent was followed by extraction with ethyl acetate. The organic phase was dried over sodium sulfate, filtered, concentrated and purified by chromatography (silica, heptane:ethyl acetate=90:10 to 60:40) to afford the title compound as an off-white solid (0.78 g, 35%). MS: m/e=413.5 [M+H]$^+$.

d) 6-(5-Formyl-3-phenyl-isoxazol-4-ylmethoxy)-nicotinic acid methyl ester

A mixture of 6-[3-phenyl-5-((E)-styryl)-isoxazol-4-ylmethoxy]-nicotinic acid methyl ester (0.62 g, 1.5 mmol), osmium(VIII) oxide solution (0.38 mL of a 2.5% solution in tert-butanol, 0.037 mmol), sodium metaperiodate (1.29 g, 6 mmol), benzyltriethylammonium chloride (0.14 g, 0.6 mmol) in dioxane (13 mL) and water (4.5 mL) was irradiated in the microwave for 10 min at 120° C. Extractive workup (ethyl acetate/water) was followed by drying of the organic phase over sodium sulfate, filtered and concentrated. Purification by chromatography (silica, heptane:ethyl acetate=100:0 to 60:40) afforded the title compound as a light yellow solid (0.26 g, 51%). MS: m/e=339.3 [M+H]$^+$.

e) 6-(5-Hydroxymethyl-3-phenyl-isoxazol-4-yl-methoxy)-nicotinic acid methyl ester A solution of 6-(5-formyl-3-phenyl-isoxazol-4-ylmethoxy)-nicotinic acid methyl ester (0.25 g, 0.74 mmol) in methanol (10 mL) was treated at room temperature with sodium borohydride (0.03 g, 0.74 mmol) and stirred for 1 h. After quenching with aqueous citric acid (5 mL of a 10% solution) and extraction with ethyl acetate the organic phase was dried (Na$_2$SO$_4$) filtered and concentrated. Purification by chromatography (silica, heptane:ethyl acetete=90:10 to 40:60) afforded the title compound as a white solid (0.22 g, 89%). MS: m/e=341.1 [M+H]$^+$.

f) N-(2-Hydroxy-ethyl)-6-(5-hydroxymethyl-3-phenyl-isoxazol-4-ylmethoxy)-nicotinamide To a stirred solution of 6-(5-hydroxymethyl-3-phenyl-isoxazol-4-ylmethoxy)-nicotinic acid methyl ester (0.11 g, 0.32 mmol) in toluene (0.5 mL) was added ethanolamine (0.03 g, 0.39 mmol) and 1,5,7-triazabicyclo[4.4.0]dec-5-ene (0.03 g, 0.17 mmol). The reaction mixture was stirred for 68 h, adsorbed on silica gel and purification by chromatography (silica, dichloromethane:methanol=100:0 to 90:10) afforded the title compound as a white solid (0.10 g, 85%). MS: m/e=370.1 [M+H]$^+$.

EXAMPLE 3

(1,1-Dioxo-1,6-thiomorpholin-4-yl)-{6-[3-(4-fluoro-phenyl)-5-hydroxymethyl-isoxazol-4-ylmethoxy]-pyridin-3-yl}-methanone

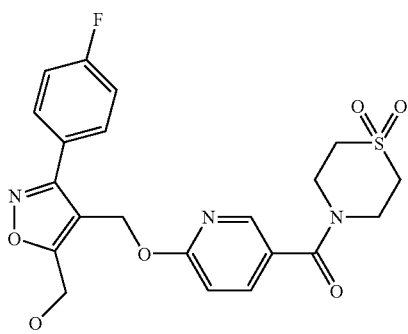

a) 3-(4-Fluoro-phenyl)-5-((E)-styryl)-isoxazole-4-carboxylic acid

To a solution of 3-(4-fluoro-phenyl)-5-methyl-isoxazole-4-carboxylic acid ethyl ester (20.0 g, 80.2 mmol) and benzaldehyde (8.19 mL, 80.2 mmol) in ethanol (113 mL) was added sodium ethoxide (2.71 M, 32.5 mL, 88.3 mmol) and the reaction mixture was heated under reflux for 1 h. Hydrochloric acid (1 N, 96.3 mL) was added and the resulting mixture was extracted with toluene. The solvent was then distilled off to afford the title compound (19.1 g, 77%) as a light yellow solid. MS: m/e=308.0 [M−H]$^-$.

b) [3-(4-Fluoro-phenyl)-5-((E)-styryl)-isoxazol-4-yl]-methanol

To a solution of 3-(4-fluoro-phenyl)-5-((E)-styryl)-isoxazole-4-carboxylic acid (19.0 g, 61.4 mmol) and triethylamine (8.6 mL, 61.4 mmol) in THF (475 mL) was added at room temperature a solution of ethyl chloroformate (5.97 mL, 61.4 mmol) in THF (55 mL). After 1 h the triethylamine hydrochloride salt was filtered off and washed with a small amount of THF. The mixture was added to a solution of sodium borohydride (6.05 g, 154 mmol) and water (55 mL). After stirring overnight at room temperature aqueous sodium hydroxide solution (1 N, 180 mL) was added. Extraction with tert-butylmethylether, removal of the solvent by distillation and chromatography (silica, dichloromethane:methanol=1:0 to 95:5) afforded the title compound (11.4 g, 63%) as light yellow solid. MS: m/e=296.2 [M+H]$^+$.

c) 6-[3-(4-Fluoro-phenyl)-5-((E)-styryl)-isoxazol-4-ylmethoxy]-nicotinic acid methyl ester To a suspension of sodium hydride (813 mg, 18.6 mmol) in 28 mL THF was added a solution of [3-(4-fluoro-phenyl)-5 ((E)-styryl)-isoxazol-4-yl]-methanol (5.00 g, 16.9 mmol) in THF (52 mL) and stirring was continued for 1 h at room temperature. A solution of methyl 6-chloronicotinate (3.26 g, 18.6 mmol) in THF (52 mL) was added. The mixture was stirred at room temperature for 3 h. Then water (50 mL) was added cautiously and then saturated ammonium chloride solution (150 mL) and water (100 mL). Extraction with ethyl acetate and chromatography (silica, ethyl acetate:heptane=1:4 to 1:1) afforded the title compound (3.88 g, 94%) as a white solid. MS: m/e=431.3 [M+H]$^+$.

d) 6-[3-(4-Fluoro-phenyl)-5-formyl-isoxazol-4-ylmethoxy]-nicotinic acid methyl ester A mixture of 6-[3-(4-fluoro-phenyl)-5-((E)-styryl)-isoxazol-4-ylmethoxy]-nicotinic acid methyl ester (3.88 g, 9.01 mmol), osmium(VIII) oxide (57.3 mg, 0.23 mmol), sodium metaperiodate (7.71 g, 36.1 mmol), benzyltriethylammonium chloride (838 mg, 3.61 mmol) in dioxane (60 mL) and water (20 mL) was heated for 15 min at 120° C. in a microwave. Water was then added to the reaction mixture and the resulting mixture extracted with ethyl acetate. The organic extract was then evaporated and the residue purified by chromatography (silica, ethyl acetate:heptane=1:4 to 2:3) to afford the title compound (2.51 g, 78%) as off white oil. MS: m/e=357.2 [M+H]$^+$.

e) 6-[3-(4-Fluoro-phenyl)-5-hydroxymethyl-isoxazol-4-ylmethoxy]-nicotinic acid methyl ester 6-[3-(4-Fluoro-phenyl)-5-formyl-isoxazol-4-ylmethoxy]-nicotinic acid methyl ester (2.50 g, 7.02 mmol) and sodium borohydride (553 mg, 14.0 mmol) in methanol (125 mL) were stirred for 2 h at room temperature. Addition of 10% aqueous citric acid (200 mL) and extraction with ethyl acetate yielded 6-[3-(4-fluoro-phenyl)-5-hydroxymethyl-isoxazol-4-ylmethoxy]-nicotinic acid methyl ester (2.60 g, quant.) as white solid. MS: m/e=359.2 [M+H]+.

f) 6-[3-(4-Fluoro-phenyl)-5-hydroxymethyl-isoxazol-4-ylmethoxy]-nicotinic acid

To 6-[3-(4-fluoro-phenyl)-5-hydroxymethyl-isoxazol-4-ylmethoxy]-nicotinic acid methyl ester (1.00 g, 2.79 mmol) in THF (6.25 mL), methanol (1.75 mL) and water (6.25 mL) was added lithium hydroxide (136 mg, 5.58 mmol). The reaction mixture was stirred overnight at room temperature. Addition of aqueous hydrochloride solution (1 N, 100 mL) and extraction with ethyl acetate yielded the title compound (1.00 g, 100%) as a white solid. MS: m/e=345.2 [M+H]+.

g) (1,1-Dioxo-1,6-thiomorpholin-4-yl)-{6-[3-(4-fluoro-phenyl)-5-hydroxymethyl-isoxazol-4-ylmethoxy]-pyridin-3-yl}-methanone To a solution of 6-[3-(4-fluoro-phenyl)-5-hydroxymethyl-isoxazol-4-ylmethoxy]-nicotinic acid (250 mg, 0.73 mmol) in THF (6.6 mL) was added 1-hydroxybenzotriazole hydrate (113 mg, 0.73 mmol), N-ethyldiisopropylamine (317 ul, 1.82 mmol), N-(3-dimethylaminopropyl)-N'-ethylcarbodiimide hydrochloride (142 mg, 0.73 mmol) and thiomorpholine 1,1-dioxide (98.1 mg, 0.73 mmol). The reaction mixture was stirred overnight at room temperature. Evaporation of the mixture followed by chromatography (silica, dichloromethane:methanol=1:0 to 9:1) afforded the title compound (0.27 g, 80%) as a white solid. MS: m/e=462.3 [M+H]+.

EXAMPLE 4

6-[3-(4-Fluoro-phenyl)-5-hydroxymethyl-isoxazol-4-ylmethoxy]-N-isopropyl-nicotinamide

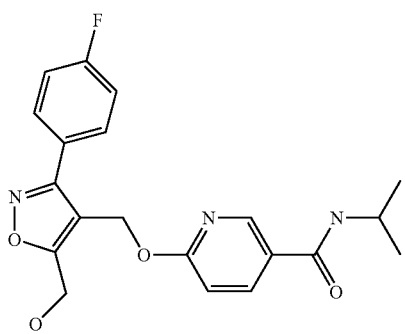

A trimethylaluminium solution (2 M in toluene, 418 µL, 0.84 mmol) was added to a solution of isopropylamine (49.6 mg, 0.84 mmol) in dioxane (3.75 mL). 6-[3-(4-Fluoro-phenyl)-5-hydroxymethyl-isoxazol-4-ylmethoxy]-nicotinic acid methyl ester (75.0 mg, 0.21 mmol) in dioxane (3.75 mL) was added after 1 h at 50° C. The reaction mixture was stirred at 85° C. overnight. Again trimethylaluminium solution in toluene (2 M, 418 µL, 0.84 mmol) and isopropylamine (49.6 mg, 0.84 mmol) was added and stirring was continued for 3 h at 85° C. The solvent was removed by distillation. The residue was purified by chromatography (silica, ethyl acetate:heptane=1:1 to 7:3) to afford the title compound (32 mg, 39%) as white solid. MS: m/e=386.2 [M+H]+.

EXAMPLE 5

6-[3-(4-Fluoro-phenyl)-5-hydroxymethyl-isoxazol-4-ylmethoxy]-N-(tetrahydro-pyran-4-yl)-nicotinamide

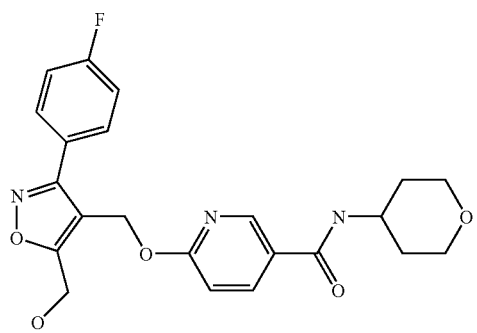

A trimethylaluminium solution (2 M in toluene, 418 µL, 0.84 mmol) was added to a solution of 4-aminotetrahydropyran (87.2 mg, 0.84 mmol) in dioxane (3.75 mL). 6-[3-(4-Fluoro-phenyl)-5-hydroxymethyl-isoxazol-4-ylmethoxy]-nicotinic acid methyl ester (75.0 mg, 0.21 mmol) in dioxane (3.75 mL) was added after 1 h at 50° C. The reaction mixture was stirred at 85° C. overnight. Again trimethylaluminium solution in toluene (2 M in toluene, 418 µL, 0.84 mmol) and 4-aminotetrahydropyran (87.2 mg, 0.84 mmol) were added and stirring was continued for 3 h at 85° C. The solvent was removed by distillation. The residue was purified by chromatography (Isolute® SPE flash NH2 column, ethyl acetate:heptane=1:1 to 9:1) to afford the title compound (24 mg, 27%) as white solid. MS: m/e=428.2 [M+H]+.

EXAMPLE 6

N-Cyclopropylmethyl-6-[3-(4-fluoro-phenyl)-5-hydroxymethyl-isoxazol-4-ylmethoxy]-nicotinamide

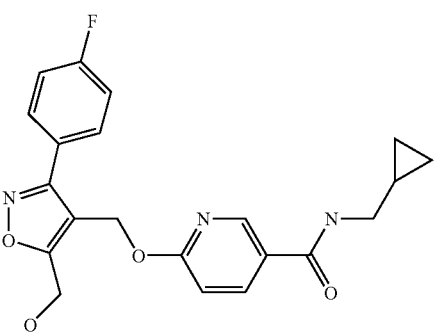

A trimethylaluminium solution (2 M in toluene, 418 µL, 0.84 mmol) was added to a solution of aminomethylcyclopropane (61.3 mg, 0.84 mmol) in dioxane (3.75 mL). 6-[3-(4-Fluoro-phenyl)-5-hydroxymethyl-isoxazol-4-ylmethoxy]-nicotinic acid methyl ester (75.0 mg, 0.21 mmol) in dioxane (3.75 mL) was added after 1 h at 50° C. The reaction mixture was stirred at 85° C. overnight. Again trimethylaluminium solution in toluene (2 M in toluene, 418 µL, 0.84 mmol) was added and stirring was continued for 3 h at 85° C. The solvent was removed by distillation. The residue was purified by chromatography (silica, ethyl acetate:heptane=4:6 to 8:2) to yield the title compound (30 mg, 36%) as a light yellow solid. MS: m/e=398.2 [M+H]+.

EXAMPLE 7

6-[3-(4-Fluoro-phenyl)-5-hydroxymethyl-isoxazol-4-ylmethoxy]-N-(2,2,2-trifluoro-ethyl)-nicotinamide

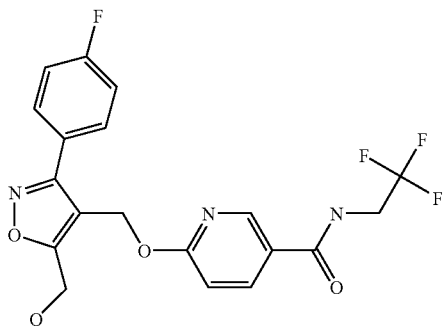

A trimethylaluminium solution (2 M in toluene, 418 µL, 0.84 mmol) was added to a solution of 2,2,2-trifluoroethylamine (84.5 mg, 0.84 mmol) in dioxane (3.75 mL). 6-[3-(4-Fluoro-phenyl)-5-hydroxymethyl-isoxazol-4-ylmethoxy]-nicotinic acid methyl ester (75 mg, 0.21 mmol) in dioxane (3.75 mL) was added after 1 h at 50° C. The reaction mixture was stirred at 85° C. overnight. Again trimethylaluminium solution (2 M in toluene, 418 µL, 0.84 mmol) was added and stirring was continued for 3 h at 85° C. The solvent was removed by distillation. The residue was purified by chromatography (silica, ethyl acetate:heptane=4:6 to 6:4 and silica, dichoromethane-methanol 98:2 to 95:5) to afford the title compound (70 mg, 78%) as white solid. MS: m/e=426.2 [M+H]+.

EXAMPLE 8

N-Cyclopropyl-6-[3-(4-fluoro-phenyl)-5-hydroxymethyl-isoxazol-4-ylmethoxy]-nicotinamide

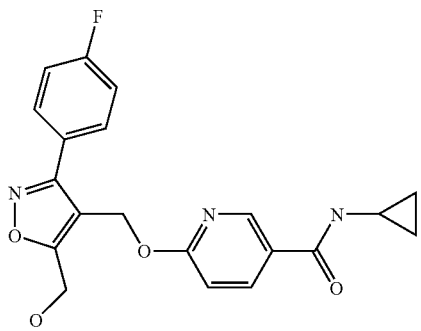

Trimethylaluminium solution (2M in toluene, 0.51 mL, 1.00 mmol) was added to a solution of cyclopropylamine (71.9 µL, 1.00 mmol) in dioxane (4.0 mL). After 45 min stirring at 50° C. a solution of 6-[3-(4-fluoro-phenyl)-5-hy-droxymethyl-isoxazol-4-ylmethoxy]-nicotinic acid methyl ester (90 mg, 0.25 mmol) in dioxane (4.0 mL) was added and stirring was continued overnight at 85° C. The dioxane was removed by distillation. The remaining material was purified by chromatography (silica, ethyl acetate) to afford the title compound (40 mg, 42%) as light brown solid. MS: m/e=382.1 [M−H]−.

EXAMPLE 9

6-[3-(4-Fluoro-phenyl)-5-hydroxymethyl-isoxazol-4-ylmethoxy]-N-(2-methoxy-ethyl)-nicotinamide

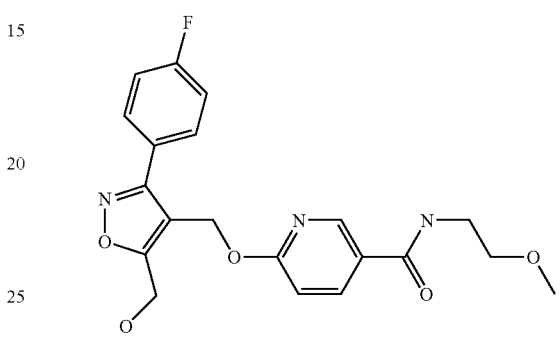

Trimethylaluminium solution (2 M in toluene, 0.51 mL, 1.00 mmol) was added to a solution of 2-methoxyethylamine (88.0 µL, 1.00 mmol) in dioxane (4 mL). After stirring for 45 min at 50° C. a solution of 6-[3-(4-fluoro-phenyl)-5-hydroxymethyl-isoxazol-4-ylmethoxy]-nicotinic acid methyl ester (90.0 mg, 0.25 mmol) in dioxane (4 mL) was added and stirring was continued overnight at 85° C. The dioxane was removed by distillation. The remaining material was purified by chromatography (silica, ethyl acetate) to yield the title compound (16.1 mg, 16%) as a white solid. MS: m/e=400.0 [M−H]−.

EXAMPLE 10

6-[3-(4-Fluoro-phenyl)-5-hydroxymethyl-isoxazol-4-ylmethoxy]-N-((1R,2R)-2-hydroxy-cyclopentyl)-nicotinamide or 6-[3-(4-Fluoro-phenyl)-5-hydroxymethyl-isoxazol-4-ylmethoxy]-N-((1S,2S)-2-hydroxy-cyclopentyl)-nicotinamide

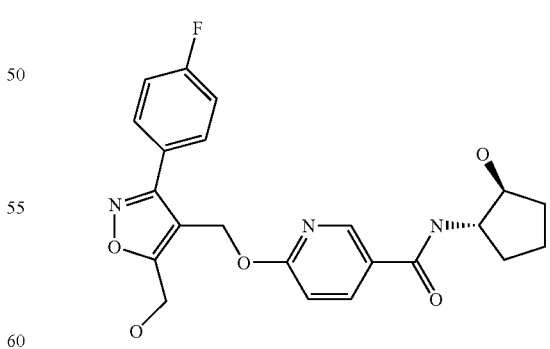

N-Ethyldiisopropylamine (177 µL, 1.02 mmol) was added to a solution of 6-[2-(4-fluoro-phenyl)-5-hydroxymethyl-isoxazol-4-ylmethoxy]-nicotinic acid (100 mg, 0.29 mmol), trans-2-amino cyclopentanol HCl (41.1 mg, 0.29 mmol), 1-hydroxybenzotriazole hydrate (45.3 mg, 0.29 mmol) and N-(3-dimethylaminopropyl)-N-ethylcarbodiimide hydrochloride (56.7 mg, 0.29 mmol) in THF (3 mL). The reaction mixture was stirred overnight at room temperature. The solvent was removed by distillation. The remaining material was purified by chromatography (silica, ethyl acetate:methanol=100:0 to 95:5) to afford the title compound (74 mg, 60%) as a white solid. MS: m/e=426.1 [M−H]⁻.

EXAMPLE 11

6-[3-(4-Fluoro-phenyl)-5-hydroxymethyl-isoxazol-4-ylmethoxy]-N-(2,2,2-trifluoro-1-methyl-ethyl)-nicotinamide

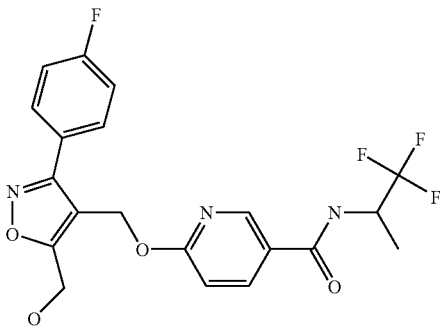

Trimethylaluminium solution (2 M in toluene, 0.56 mL, 1.12 mmol) was added to a solution of 1,1,1-trifluoro-isopropylamine (129 mg, 1.12 mmol) in dioxane (5 mL). After stirring for 1 h at 50° C. a solution of 6-[3-(4-fluoro-phenyl)-5-hydroxymethyl-isoxazol-4-ylmethoxy]-nicotinic acid methyl ester (100 mg, 0.28 mmol) in dioxane (5 mL) was added to the reaction mixture and stirring was continued overnight at 85° C. The dioxane was removed by distillation. The remaining material was purified by chromatography (silica, ethyl acetate:heptane=2:3 to 3:2) to afford the title compound (80 mg, 65%) as a white solid. MS: m/e=438.1 [M−H]⁻

EXAMPLE 12

6-[3-(4-Fluoro-phenyl)-5-hydroxymethyl-isoxazol-4-ylmethoxy]-N-(2-hydroxy-1,1-dimethyl-ethyl)-nicotinamide

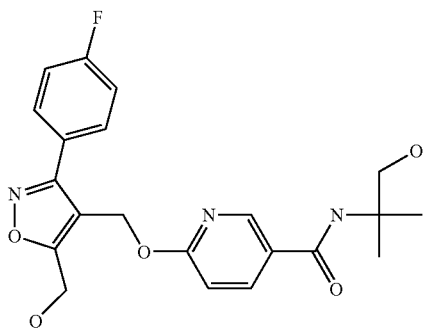

To a solution of 6-[3-(4-fluoro-phenyl)-5-hydroxymethyl-isoxazol-4-ylmethoxy]-nicotinic acid (200 mg, 0.58 mmol) in THF (6 mL) was added 1-hydroxybenzotriazole hydrate (90.8 mg, 0.58 mmol), N-ethyldiisopropylamine (254 μL, 1.45 mmol), N-(3-dimethylaminopropyl)-N'-ethylcarbodiimide hydrochloride (114 mg, 0.58 mmol) and 2-amino-2-methyl-1-propanol (53.4 mg, 0.58 mmol). The reaction mixture was stirred overnight at room temperature. Chromatography (silica, dichloromethane:methanol=0:100 to 95:5) afforded the title compound (160 mg, 66%) as a colorless oil. MS: m/e=416.2 [M+H]⁺.

EXAMPLE 13

6-[3-(4-Fluoro-phenyl)-5-hydroxymethyl-isoxazol-4-ylmethoxy]-N-(2,2,3,3,3-pentafluoro-propyl)-nicotinamide

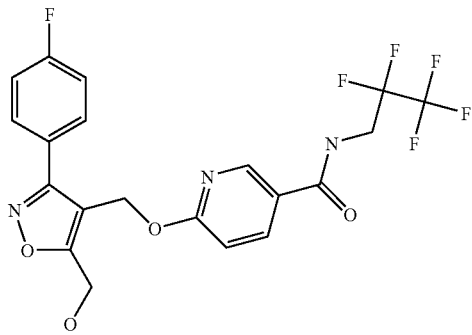

Trimethylaluminium solution (2 M in toluene, 0.84 mL, 1.67 mmol) was added to a solution of 2,2,3,3,3-pentafluoro-propylamine (121 μL, 1.12 mmol) in dioxane (4 mL). After stirring for 45 min at 50° C. a solution of 6-[3-(4-fluoro-phenyl)-5-hydroxymethyl-isoxazol-4-ylmethoxy]-nicotinic acid methyl ester (100 mg, 0.28 mmol) in dioxane (4 mL) was added and stirring was continued overnight at 85° C. The dioxane was removed by distillation. The remaining material was purified by chromatography (silica, ethyl acetate:heptane 1:1) to yield the title compound (103 mg, 77%) as a white solid. MS: m/e=474.2 [M−H]⁻.

EXAMPLE 14

6-[3-(4-Fluoro-phenyl)-5-hydroxymethyl-isoxazol-4-ylmethoxy]-N-((R)-1-hydroxymethyl-propyl)-nicotinamide

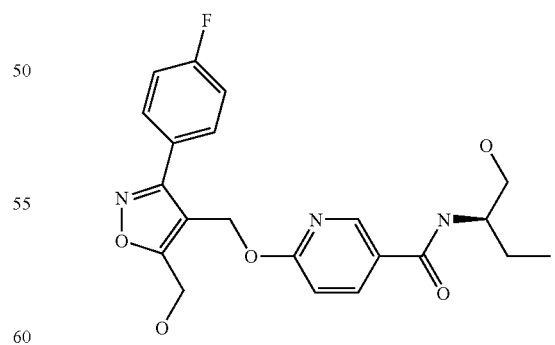

Hydroxybenzotriazole hydrate (45.3 mg, 0.29 mmol), N-ethyldiisopropylamine (253 μL, 1.45 mmol) and N-(3-dimethylaminopropyl)-N'-ethylcarbodiimide hydrochloride (56.7 mg, 0.29 mmol) were added at 0° C. to a solution of 6-[3-(4-fluoro-phenyl)-5-hydroxymethyl-isoxazol-4-ylmethoxy]-nicotinic acid (100 mg, 0.29 mmol) and (R)-(−)-2- amino-1-butanol (34.0 µL, 0.35 mmol) in THF (8 mL). The reaction mixture was stirred at room temperature overnight. Extraction with 1 N aqueous hydrochloric acid/ethyl acetate and chromatography (silica, ethyl acetate:heptane=1:1 to 100:0) afforded the title compound (60 mg, 50%) as a white solid. MS: m/e=414.2 [M–H]⁻.

EXAMPLE 15

6-[3-(4-Fluoro-phenyl)-5-hydroxymethyl-isoxazol-4-ylmethoxy]-N-((S)-1-hydroxymethyl-propyl)-nicotinamide

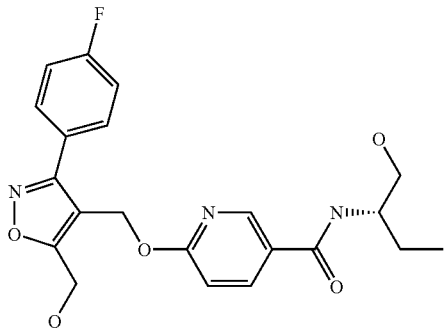

Hydroxybenzotriazole hydrate (45.3 mg, 0.29 mmol), N-ethyldiisopropylamine (253 µL, 1.45 mmol) and N-(3-dimethylaminopropyl)-N'-ethylcarbodiimide hydrochloride (56.7 mg, 0.29 mmol) were added at 0° C. to a solution of 6-[3-(4-fluoro-phenyl)-5-hydroxymethyl-isoxazol-4-ylmethoxy]-nicotinic acid (100 mg, 0.29 mmol) and (S)-(+)-2-amino-1-butanol (34.0 µL, 0.35 mmol) in THF (8 mL). The reaction mixture was stirred at room temperature overnight. Extraction with 1 N aqueous hydrochloric acid/ethyl acetate and chromatography (silica, ethyl acetate:heptane=0:100 to 100:0) afforded the title compound (75 mg, 62%) as a white solid. MS: m/e=414.2 [M–H]⁻.

EXAMPLE 16

6-[3-(4-Fluoro-phenyl)-5-hydroxymethyl-isoxazol-4-ylmethoxy]-N-(1-methyl-1H-pyrazol-4-yl)-nicotinamide

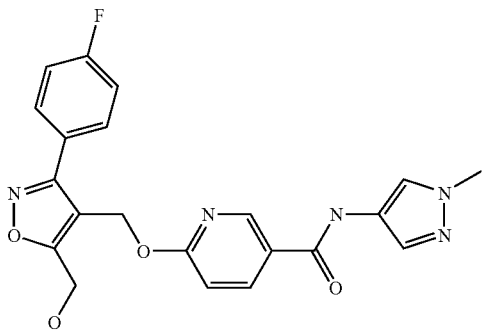

To a solution of 6-[3-(4-fluoro-phenyl)-5-hydroxymethyl-isoxazol-4-ylmethoxy]-nicotinic acid (100 mg, 0.29 mmol) in THF (3 mL) were added 1-hydroxybenzotriazole hydrate (45.3 mg, 0.29 mmol), N-ethyldiisopropylamine (127 µL, 0.73 mmol), N-(3-dimethylaminopropyl)-N'-ethylcarbodiimide hydrochloride (56.7 mg, 0.29 mmol) and 1-methyl-1H-pyrazol-4-ylamine (28.2 mg, 0.29 mmol). The reaction mixture was stirred overnight at room temperature. Chromatography (silica, ethyl acetate:heptane=2:1 to 9:1) afforded the title compound (70 mg, 57%) as a white solid. MS: m/e=424.2 [M+H]⁺.

EXAMPLE 17

6-[3-(4-Fluoro-phenyl)-5-hydroxymethyl-isoxazol-4-ylmethoxy]-N-(3-methyl-oxetan-3-yl)-nicotinamide

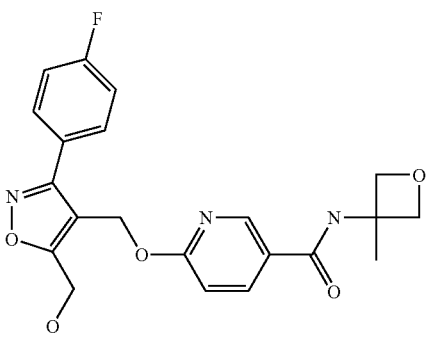

To a solution of 6-[3-(4-fluoro-phenyl)-5-hydroxymethyl-isoxazol-4-ylmethoxy]-nicotinic acid (100 mg, 0.29 mmol) in DMF (3.3 mL) was added 1,1'-carbonyl-diimidazole (58.2 mg, 0.35 mmol). The reaction mixture was stirred for 1 h at 60° C. 3-Methyl-3-oxetanamine (27.8 mg, 0.32 mmol) was then added at room temperature and the mixture was stirred overnight. Extraction with water/ethyl acetate and chromatography (silica, ethyl acetate:heptane=1:4 to 1:1) afforded the title compound (10 mg, 8%) as a white solid. MS: m/e=414.2 [M+H]⁺.

EXAMPLE 18

{6-[3-(4-Chloro-phenyl)-5-hydroxymethyl-isoxazol-4-ylmethoxy]-pyridin-3-yl}-(1,1-dioxo-1-thiomorpholin-4-yl)-methanone

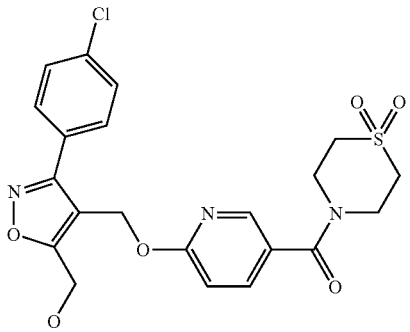

A solution of {6-[3-(4-chloro-phenyl)-5-methyl-isoxazol-4-ylmethoxy]-pyridin-3-yl}-(1,1-dioxo-1-thiomorpholin-4-yl)-methanone (44.5 mg, 0.096 mmol) in DMSO (2 mL) was added to a suspension of CYP3A4 (800 nmol)) and NADP in a total volume of 1000 mL reaction buffer (823 mL 0.1M K⁺ phosphate buffer pH 7.4, 50 mL 1M trisodium citrate, 10 mL 1M magnesium chloride, 2.5 mL 20 mM NADP). The mixture was shaken in a 2 L baffled Erlenmeyer flask at 220 rpm at 27° C. for 4 h, by which time the ratio of substrate:product (12:8 at 3 h, and 11:9 at 4 h) remained almost constant (reaction monitoring: 0.2 mL suspension was treated with 0.2 mL acetonitrile, centrifuged at 13,200 rpm for 2 min, and supernatant was analyzed by HPLC). The suspension (1000 mL) was extracted with 2 L ethyl acetate. The solvent was distilled off and the residue was dissolved in 100 mL water. This was applied to a 10 g reverse phase C18 cartridge which was eluted with a step gradient of acetonitrile in water (15 mL aliquots). Metabolite containing fractions eluting at 35% MeCN were pooled as appropriate and after removal of organic solvent by rotary evaporation were freeze dried to afford the title compound (8.4 mg, 18%) as a white solid. MS: m/e=536.1 [M+CH$_3$COO]$^-$.

EXAMPLE 19

6-[3-(4-Chloro-phenyl)-5-hydroxymethyl-isoxazol-4-ylmethoxy]-N-isopropyl-nicotinamide

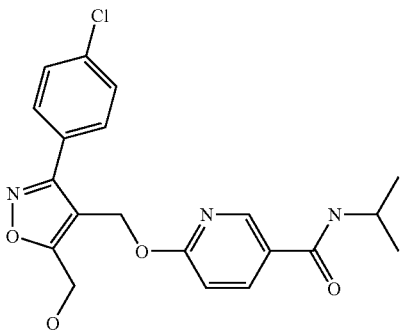

As described for example 18, biotransformation of 6-[3-(4-chloro-phenyl)-5-methyl-isoxazol-4-ylmethoxy]-N-isopropyl-nicotinamide (47 mg, 0.12 mmol) by CYP 3A4 was performed. The residue was purified by chromatography (silica, dichloromethane) to afford the title compound (8.5 mg, 49%) as a white solid. MS: m/e=402.2 [M+H]$^+$.

EXAMPLE 20

6-[3-(4-Chloro-phenyl)-5-hydroxymethyl-isoxazol-4-ylmethoxy]-N-cyclopropyl-nicotinamide

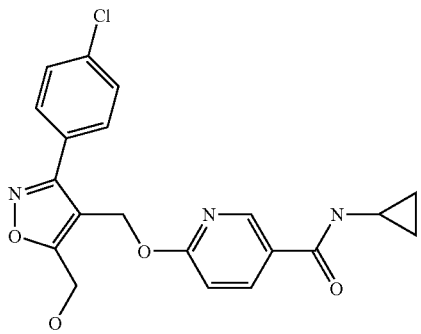

a) 3-(4-Chloro-phenyl)-5-([E]-styryl)-isoxazole-4-carboxylic acid

To a stirred solution of 3-(4-chloro-phenyl)-5-methyl-isoxazole-4-carboxylic acid ethyl ester (9.6 g, 36.1 mmol) and benzaldehyde (3.69 mL, 36.1 mmol) in ethanol (54 mL) was added sodium ethoxide (2.71 M, 14.6 mL, 39.7 mmol) and the reaction was heated unded reflux for 10 min. Hydrochloric acid (1 N, 43.4 mL) was added and the resulting mixture was then triturated with dichloromethane and filtered to afford the title compound (6.21 g, 53%) as a light yellow solid. MS: m/e=324.1 [M−H]$^-$.

b) [3-(4-Chloro-phenyl)-5-([E]-styryl)-isoxazol-4-yl]-methanol

To a solution of 3-(4-chloro-phenyl)-5-([E]-styryl)-isoxazole-4-carboxylic acid (6.0 g, 18.4 mmol) and triethylamine (2.58 mL, 18.4 mmol) in THF (150 mL) was added at room temperature a solution of ethyl chloroformate (1.8 mL, 18.4 mmol) in THF (17.4 mL). After 1 h triethylamine hydrochloride salt was filtered off, and washed with a small amount of THF. The solution was then added to a solution of sodium borohydride (1.82 g, 46.1 mmol) in water (18 mL). After stirring overnight at room temperature sodium hydroxide solution (1 N) was added. Extraction with tert-butylmethylether and purification by chromatography (silica, dichloromethane) afforded the title compound (4.52 g, 79%) as a white solid. MS: m/e=369.9 [M+OAc]$^-$.

c) 6-[3-(4-Chloro-phenyl)-5-([E]-styryl)-isoxazol-4-ylmethoxy]-nicotinic acid methyl ester To a suspension of sodium hydride (2.64 g, 60.5 mmol) in THF (100 mL) was added a solution of [3-(4-chloro-phenyl)-5-([E]-styryl)-isoxazol-4-yl]-methanol (17.2 g, 55.0 mmol) in THF (185 mL) at 0° C. The reaction mixture was stirred for 60 min at room temperature. A solution of methyl 6-chloronicotinate (10.6 g, 60.5 mmol) in THF (185 mL) was added at 0° C. The mixture was stirred at room temperature for 2 h and the product was extracted with ethyl acetate/aqueous ammonium chloride and ethyl acetate/brine. Chromatography (silica, ethyl acetate:heptane 2:8 to 7:3) afforded the title compound (15.6 g, 64%) as a white solid. MS: m/e (%)=446 (0.7, M$^+$), 309 (47), 294 (28), 240 (26), 131 (100), 103 (51).

d) 6-[3-(4-Chloro-phenyl)-5-formyl-isoxazol-4-ylmethoxy]-nicotinic acid methyl ester 6-[3-(4-Chloro-phenyl)-5-([E]-styryl)-isoxazol-4-ylmethoxy]-nicotinic acid methyl ester (6.35 g, 14.2 mmol) was treated with osmium(VIII) oxide (90.3 mg, 355 μmol), sodium metaperiodate (12.2 g, 56.8 mmol) and benzyltriethylammonium chloride (1.32 mg, 5.68 mmol) in dioxane (140 mL) and water (47 mL). The mixture was heated for 35 min at 120° C. in a microwave. Extraction with ethyl acetate/water and chromatogaphy (silica, ethyl acetate:heptane 1:9 to 1:1) afforded the title compound (3.43 g, 65%) as a white solid. MS: m/e=373.1 [M+H]$^+$.

e) 6-[3-(4-Chloro-phenyl)-5-hydroxymethyl-isoxazol-4-ylmethoxy]-nicotinic acid methyl ester Sodium borohydride (719 mg, 18.2 mmol) was added in portions to 6-[3-(4-chloro-phenyl)-5-formyl-isoxazol-4-ylmethoxy]-nicotinic acid methyl ester (3.4 g, 9.12 mmol) in methanol (170 mL). After stirring for 1 h at room temperature a solution of citric acid (10% in water) was added. Extraction with ethyl acetate and chromatography (silica, ethyl acetate:heptane=1:9 to 1:1) afforded the title compound (3.11 g, 91%) as a white solid. MS: m/e=375.1 [M+H]⁺.

f) 6-[3-(4-Chloro-phenyl)-5-hydroxymethyl-isoxazol-4-ylmethoxy]-nicotinic acid 6-[3-(4-Chloro-phenyl)-5-hydroxymethyl-isoxazol-4-ylmethoxy]-nicotinic acid methyl ester (3.0 g, 8.0 mmol) in THF (20 mL), methanol (5.2 mL) and water (19 mL) was treated with lithium hydroxide monohydrate (678 mg, 16.0 mmol) for 8 h at room temperature. Hydrochloride acid (1 N, 25 mL) and water (200 mL) were added to the reaction mixture. The precipitate was filtered off and washed with water and ethyl acetate to afford the title compound (2.67 g, 93%) as a white solid. MS: m/e=359.0 [M–H]⁻.

g) 6-[3-(4-Chloro-phenyl)-5-hydroxymethyl-isoxazol-4-ylmethoxy]-N-cyclopropyl-nicotinamide To a solution of 6-[3-(4-chloro-phenyl)-5-hydroxymethyl-isoxazol-4-ylmethoxy]-nicotinic acid (100 mg, 0.28 mmol) and cyclopropylamine (16.1 mg, 0.28 mmol) in THF (10 mL) were added at 0° C., 1-hydroxybenzotriazole hydrate (43.3 mg, 0.28 mmol), N-ethyldiisopropylamine (121 µL, 0.69 mmol) and N-(3-dimethylaminopropyl)-N'-ethylcarbodiimide hydrochloride (54.2 mg, 0.28 mmol). The mixture was stirred at room temperature overnight. The solvent was removed by distillation. The remaining material was purified by chromatography (silica, dichloromethane:ethyl acetate=4:6 to 1:0) to afford the title compound (95.2 mg, 86%) as a white solid. MS: m/e=398.0 [M–H]⁺.

EXAMPLE 21

6-[3-(4-Chloro-phenyl)-5-hydroxymethyl-isoxazol-4-ylmethoxy]-N-(2,2,2-trifluoro-ethyl)-nicotinamide

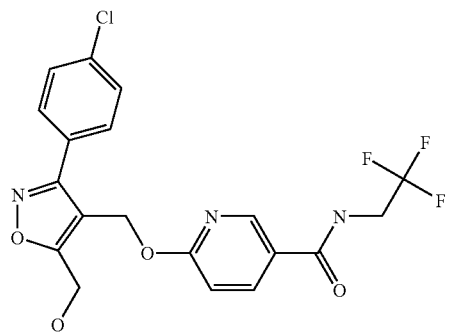

To a solution of 6-[3-(4-chloro-phenyl)-5-hydroxymethyl-isoxazol-4-ylmethoxy]-nicotinic acid (100 mg, 0.28 mmol) and 2,2,2-trifluoroethylamine (38.3 mg, 0.28 mmol) in THF (10 mL) were added at 0° C., 1-hydroxybenzotriazole hydrate (43.3 mg, 0.28 mmol), N-ethyldiisopropylamine (121 µL, 0.69 mmol) and N-(3-dimethylaminopropyl)-N'-ethylcarbodiimide hydrochloride (54.2 mg, 0.28 mmol). The reaction mixture was stirred at room temperature overnight. The solvent was removed by distillation. The remaining material was purified by chromatography (silica, ethyl acetate:heptane=1:9 to 1:1) to afford the title compound (81 mg, 66%) as a white solid. MS: m/e=440.1 [M–H]⁻.

EXAMPLE 22

6-[3-(4-Chloro-phenyl)-5-hydroxymethyl-isoxazol-4-ylmethoxy]-N,N-dimethyl-nicotinamide

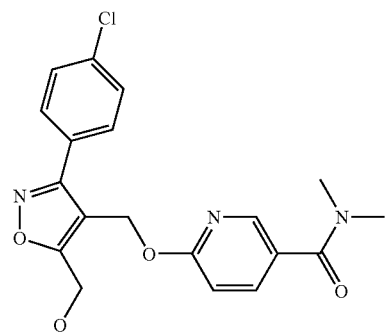

To a solution of 6-[3-(4-chloro-phenyl)-5-hydroxymethyl-isoxazol-4-ylmethoxy]-nicotinic acid (100 mg, 0.28 mmol) and dimethylamine hydrochloride (23.1 mg, 0.28 mmol) in THF (10 mL) were added at 0° C., 1-hydroxybenzotriazole hydrate (43.3 mg, 0.28 mmol), N-ethyldiisopropylamine (170 µL, 0.97 mmol) and N-(3-dimethylaminopropyl)-N'-ethylcarbodiimide hydrochloride (54.2 mg, 0.28 mmol). The reaction mixture was stirred at room temperature overnight. The solvent was removed by distillation. The remaining material was purified by chromatography (silica, ethyl acetate:heptane=4:6 to 1:0) to afford the title compound (66 mg, 61%) as a white solid. MS: m/e=446.3 [M+OAc]⁻.

EXAMPLE 23

6-[3-(4-Chloro-phenyl)-5-hydroxymethyl-isoxazol-4-ylmethoxy]-N-(2-hydroxy-1,1-dimethyl-ethyl)-nicotinamide

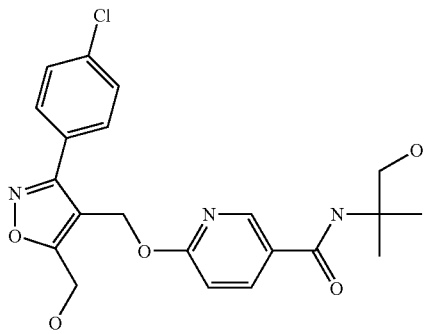

To a solution of 6-[3-(4-chloro-phenyl)-5-hydroxymethyl-isoxazol-4-ylmethoxy]-nicotinic acid (100 mg, 0.28 mmol) and 2-amino-2-methyl-1-propanol (25.5 mg, 0.28 mmol) in THF (10 mL) were added at 0° C., 1-hydroxybenzotriazole hydrate (43.3 mg, 0.28 mmol), N-ethyldiisopropylamine (121 µL, 0.69 mmol) and N-(3-dimethylaminopropyl)-N'-ethylcarbodiimide hydrochloride (54.2 mg, 0.28 mmol). The reaction mixture was stirred at room temperature overnight.

The solvent was removed by distillation. The remaining material was purified by chromatography (silica, dichloromethane:methanol=99:1 to 95:5) to afford the title compound (91 mg, 76%) as a white solid. MS: m/e=430.1 [M−H]⁻.

EXAMPLE 24

6-[3-(4-Chloro-phenyl)-5-hydroxymethyl-isoxazol-4-ylmethoxy]-N-(1-methyl-1H-pyrazol-4-yl)-nicotinamide

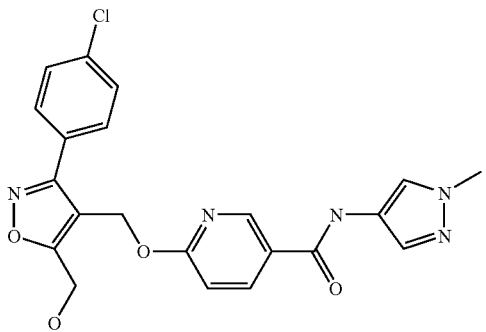

To a solution of 6-[3-(4-chloro-phenyl)-5-hydroxymethyl-isoxazol-4-ylmethoxy]-nicotinic acid (100 mg, 0.28 mmol) and 1-methyl-1H-pyrazol-4-ylamine (26.9 mg, 0.28 mmol) in THF (10 mL) were added at 0° C., 1-hydroxybenzotriazole hydrate (43.3 mg, 0.28 mmol), N-ethyldiisopropylamine (121 µL, 0.69 mmol) and N-(3-dimethylaminopropyl)-N'-ethylcarbodiimide hydrochloride (54.2 mg, 0.28 mmol). The reaction mixture was stirred at room temperature overnight. The solvent was removed by distillation. The remaining material was purified by chromatography (silica, dichloromethane:methanol=99:1 to 95:5) to afford the title compound (101 mg, 83%) as a white solid. MS: m/e=440.2 [M+H]⁺.

EXAMPLE 25

6-[3-(4-Chloro-phenyl)-5-hydroxymethyl-isoxazol-4-ylmethoxy]-N-([S]-2,2,2-trifluoro-1-methyl-ethyl)-nicotinamide

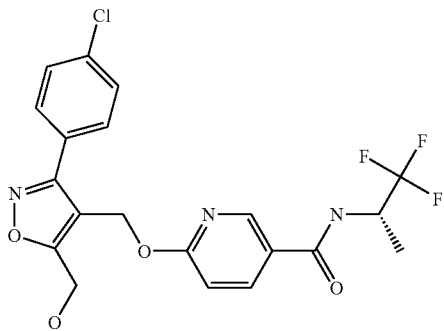

To a solution of 6-[3-(4-chloro-phenyl)-5-hydroxymethyl-isoxazol-4-ylmethoxy]-nicotinic acid (100 mg, 0.28 mmol) and L-2,2,2-trifluoro-1-(methyl)ethylamine (32 mg, 0.28 mmol) in THF (10 mL) were added at 0° C., 1-hydroxybenzotriazole hydrate (43.3 mg, 0.28 mmol), N-ethyldiisopropylamine (121 µL, 0.69 mmol) and N-(3-dimethylaminopropyl)-N'-ethylcarbodiimide hydrochloride (54.2 mg, 0.28 mmol). The reaction mixture was stirred at room temperature overnight. The solvent was removed by distillation. The remaining material was purified by chromatography (silica, ethyl acetate:heptane=2:8 to 1:0, then silica, dichloromethane:methanol=99:1 to 95:5) to afford the title compound (75 mg, 60%) as a white solid. MS: m/e=454.1 [M−H]⁻.

EXAMPLE 26

6-[3-(4-Chloro-phenyl)-5-hydroxymethyl-isoxazol-4-ylmethoxy]-N-((1S,2S)-2-hydroxy-cyclopentyl)-nicotinamide or 6-[3-(4-Chloro-phenyl)-5-hydroxymethyl-isoxazol-4-ylmethoxy]-N-((1R,2R)-2-hydroxy-cyclopentyl)-nicotinamide

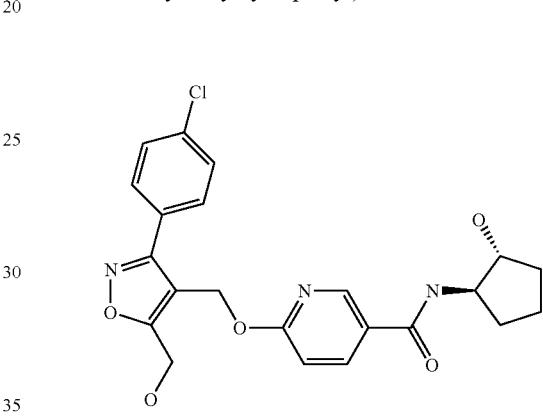

a) 6-[3-(4-Chloro-phenyl)-5-hydroxymethyl-isoxazol-4-ylmethoxy]-N-([1S,2S]-2-hydroxy-cyclopentyl)-nicotinamide and 6-[3-(4-Chloro-phenyl)-5-hydroxymethyl-isoxazol-4-ylmethoxy]-N-([1R,2R]-2-hydroxy-cyclopentyl)-nicotinamide To a solution of 6-[3-(4-chloro-phenyl)-5-hydroxymethyl-isoxazol-4-ylmethoxy]-nicotinic acid (300 mg, 0.83 mmol) and trans-2-amino cyclopentanol hydrochloride (118 mg, 0.83 mmol) in THF (10 mL) were added at 0° C. 1-hydroxybenzotriazole hydrate (130 mg, 0.83 mmol), N-ethyldiisopropylamine (509 µL, 2.91 mmol) and N-(3-dimethylaminopropyl)-N'-ethylcarbodiimide hydrochloride (163 mg, 0.83 mmol). The reaction mixture was stirred at room temperature overnight. The solvent was removed by distillation. The remaining material was purified by chromatography (silica, dichloromethane:methanol=99:1 to 95:5) to afford the title compound (230 mg, 62%) as a white solid. MS: m/e=442.2 [M−H]⁻.

b) 6-[3-(4-Chloro-phenyl)-5-hydroxymethyl-isoxazol-4-ylmethoxy]-N-((1S,2S)-2-hydroxy-cyclopentyl)-nicotinamide or 6-[3-(4-Chloro-phenyl)-5-hydroxymethyl-isoxazol-4-ylmethoxy]-N-((1R,2R)-2-hydroxy-cyclopentyl)-nicotinamide 6-[3-(4-Chloro-phenyl)-5-hydroxymethyl-isoxazol-4-ylmethoxy]-N-([1S,2S]-2-hydroxy-cyclopentyl)-nicotinamide and 6-[3-(4-chloro-phenyl)-5-hydroxymethyl-isoxazol-4-ylmethoxy]-N-([1R,2R]-2-hydroxy-cyclopentyl)-nicotinamide (230 mg) were separated by chiral HPLC (Chiralpak AD, isopropanol:heptane=30:70) to yield 6-[3-(4-chloro-phenyl)-5-hydroxymethyl-isoxazol-4-ylmethoxy]-N-([1S,2S]-2-hydroxy-cyclopentyl)-nicotinamide or 6-[3-(4-chloro-phenyl)-5-hydroxymethyl-isoxazol-4-ylmethoxy]-N-([1R,2R]-2-hydroxy-cyclopentyl)-nicotinamide (110 mg, (−)-enantiomer, first eluting) as a colourless oil. MS: m/e=442.2 [M−H]⁻.

EXAMPLE 27

6-[3-(4-Chloro-phenyl)-5-hydroxymethyl-isoxazol-4-ylmethoxy]-N-([1R,2R]-2-hydroxy-cyclopentyl)-nicotinamide or 6-[3-(4-Chloro-phenyl)-5-hydroxymethyl-isoxazol-4-ylmethoxy]-N-([1S,2S]-2-hydroxy-cyclopentyl)-nicotinamide

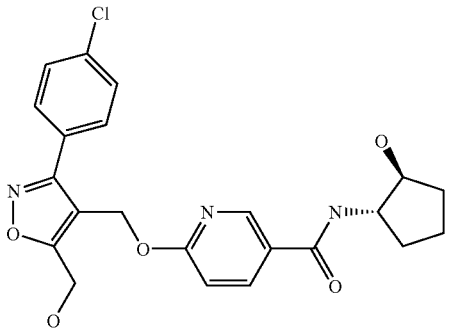

6-[3-(4-Chloro-phenyl)-5-hydroxymethyl-isoxazol-4-yl-methoxy]-N-([1S,2S]-2-hydroxy-cyclopentyl)-nicotinamide and 6-[3-(4-chloro-phenyl)-5-hydroxymethyl-isoxazol-4-yl-methoxy]-N-([1R,2R]-2-hydroxy-cyclopentyl)-nicotinamide (230 mg) were separated by chiral HPLC (Chiralpak AD, isopropanol:heptane=30:70) to yield 6-[3-(4-chloro-phenyl)-5-hydroxymethyl-isoxazol-4-ylmethoxy]-N-([1S,2S]-2-hydroxy-cyclopentyl)-nicotinamide or 6-[3-(4-chloro-phenyl)-5-hydroxymethyl-isoxazol-4-ylmethoxy]-N-([1R,2R]-2-hydroxy-cyclopentyl)-nicotinamide (110 mg, (+)-enantiomer, second eluting) as a colourless oil. MS: m/e=442.2 [M−H]⁻.

EXAMPLE 28

6-[3-(3,4-Difluoro-phenyl)-5-hydroxymethyl-isoxazol-4-ylmethoxy]-N-isopropyl-nicotinamide

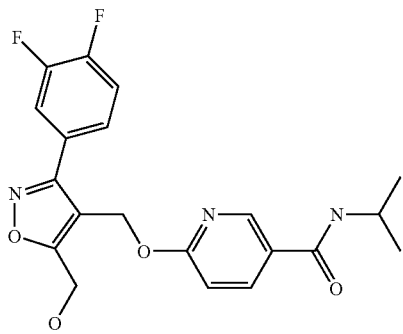

a) 3-(3,4-Difluoro-phenyl)-5-([E]-styryl)-isoxazole-4-carboxylic acid

To a stirred solution of 3-(3,4-difluoro-phenyl)-5-methyl-isoxazole-4-carboxylic acid ethyl ester (50 g, 187 mmol) and benzaldehyde (19.1 mL, 187 mmol) in ethanol (280 mL) was added sodium ethoxide (2.71 M, 75.8 mL, 206 mmol) and the reaction was stirred at reflux for 1 h. Hydrochloric acid (1 N, 225 mL) was added and the resulting mixture was then triturated with dichloromethane and filtered to afford the title compound (53.5 g, 87%) as a light yellow solid. MS: m/e=328.3 [M+H]⁺.

b) [3-(3,4-Difluoro-phenyl)-5-([E]-styryl)-isoxazol-4-yl]-methanol

To a solution of 3-(3,4-difluoro-phenyl)-5-([E]-styryl)-isoxazole-4-carboxylic acid (18 g, 55.0 mmol) and triethylamine (7.7 mL, 55.0 mmol) in THF (450 mL) was added at room temperature a solution of ethyl chloroformate (5.35 mL, 55.0 mmol) in THF (52 mL). After 1 h triethylamine hydrochloride salt was filtered off and washed with a small amount of THF. The solution was added to a solution of sodium borohydride (5.42 g, 138 mmol) in water (52 mL). The mixture was stirred overnight at room temperature. Sodium hydroxide solution (1 N, 180 mL) was added. Extraction with tert-butylmethylether and chromatography (silica, dichloromethane) afforded the title compound (12.6 g, 73%) as a light green solid. MS: m/e=314.2 [M+H]⁺.

c) 6-[3-(3,4-Difluoro-phenyl)-5-([E]-styryl)-isoxazol-4-ylmethoxy]-nicotinic acid methyl ester To a suspension of sodium hydride (1.23 mg, 28.1 mmol) in 45 mL THF was added a solution of [3-(3,4-difluoro-phenyl)-5-([E]-styryl)-isoxazol-4-yl]-methanol (8.0 g, 25.5 mmol) in THF (84 mL) at room temperature. The reaction mixture was stirred for 1 h at room temperature. A solution of methyl 6-chloronicotinate (4.92 g, 28.1 mmol) in THF (84 mL) was added. The reaction was stirred at room temperature for 3 h and water (150 mL) and saturated aqueous ammonium chloride solution (100 mL) were added. Extraction with ethyl acetate and chromatography (silica, ethyl acetate:heptane=1:4 to 2:3) afforded the title compound (9.24 g, 81%) as a yellow solid. MS: m/e=507.1 [M+CH₃COO]⁻.

d) 6-[3-(3,4-Difluoro-phenyl)-5-formyl-isoxazol-4-ylmethoxy]-nicotinic acid methyl ester 6-[3-(3,4-Difluoro-phenyl)-5-([E]-styryl)-isoxazol-4-yl-methoxy]-nicotinic acid methyl ester (5.0 g, 11.2 mmol), osmium(VIII) oxide (70.9 mg, 0.28 mmol), sodium metaperiodate (9.54 mg, 44.6 mmol), benzyltriethylammonium chloride (1.04 mg, 4.46 mmol) in dioxane (75 mL) and water (25 mL) were heated for 15 min at 120° C. in a microwave. Addition of water and extraction with ethyl acetate and chromatography (silica, ethyl acetate:heptane=1:4 to 1:1) afforded the title compound (2.54 g, 61%) as a white solid. MS: m/e=375.1 [M+H]⁺.

e) 6-[3-(3,4-Difluoro-phenyl)-5-hydroxymethyl-isoxazol-4-ylmethoxy]-nicotinic acid methyl ester 6-[3-(3,4-Difluoro-phenyl)-5-formyl-isoxazol-4-ylmethoxy]-nicotinic acid methyl ester (3.50 g, 9.35 mmol) in methanol (125 mL) was treated with sodium borohydride (737 mg, 18.7 mmol) for 30 min at room temperature. Addition of aqueous citric acid solution (10%, 300 mL) and extraction with ethyl acetate afforded the title compound (3.0 g, 85%) as a white solid. MS: m/e=377.2 [M+H]$^+$.

f) 6-[3-(3,4-Difluoro-phenyl)-5-hydroxymethyl-isoxazol-4-ylmethoxy]-N-isopropyl-nicotinamide A trimethylaluminium solution (2M in toluene, 798 ul, 1.60 mmol) was added to a solution of isopropylamine (63.2 mg, 1.06 mmol) in dioxane (5 mL). 6-[3-(3,4-Difluoro-phenyl)-5-hydroxymethyl-isoxazol-4-ylmethoxy]-nicotinic acid methyl ester (100 mg, 0.27 mmol) in dioxane (5 mL) was added after 1 h at 50° C. The reaction mixture was stirred at 85° C. overnight. The solvent was removed by distillation. The residue was purified by chromatography (silica, ethyl acetate:heptane=2:3 to 7:3) to afford the title compound (30 mg, 28%) as a light brown solid. MS: m/e=404.3 [M+H]$^+$.

EXAMPLE 29

6-[3-(3,4-Difluoro-phenyl)-5-hydroxymethyl-isoxazol-4-ylmethoxy]-N-(tetrahydro-pyran-4-yl)-nicotinamide

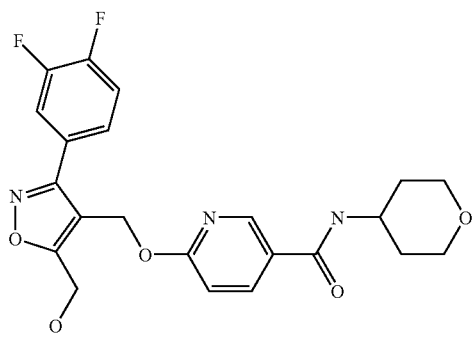

A trimethylaluminium solution (2 M in toluene, 532 µL, 1.06 mmol) was added to a solution of 4-aminotetrahydropyran (111 mg, 1.06 mmol) in dioxane (5 mL). 6-[3-(3,4-Difluoro-phenyl)-5-hydroxymethyl-isoxazol-4-ylmethoxy]-nicotinic acid methyl ester (100 mg, 0.27 mmol) in dioxane (5 mL) was added after 1 h at 50° C. The reaction mixture was stirred at 85° C. overnight. Again trimethylaluminium solution (2 M in toluene, 500 µL, 1.0 mmol) was added and stirring was continued for 3 h at 85° C. The solvent was removed by distillation. The residue was purified by chromatography (silica, dichloromethane:methanol=100:0 to 95:5) to afford the title compound (60 mg, 50%) as a white solid. MS: m/e=446.4 [M+H]$^+$.

EXAMPLE 30

N-Cyclopropylmethyl-6-[3-(3,4-difluoro-phenyl)-5-hydroxymethyl-isoxazol-4-ylmethoxy]-nicotinamide

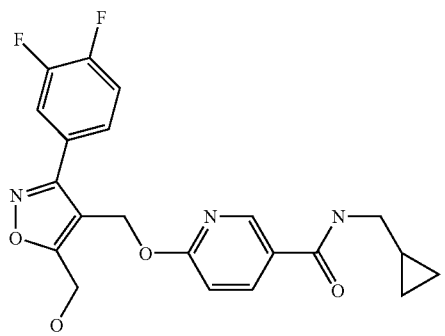

Trimethylaluminium solution (2 M in toluene, 0.8 mL, 1.60 mmol) was added to a solution of aminomethylcyclopropane (78 mg, 1.06 mmol) in dioxane (5 mL). The mixture was stirred for 1 h at 50° C. Then a solution of 6-[3-(3,4-difluoro-phenyl)-5-hydroxymethyl-isoxazol-4-ylmethoxy]-nicotinic acid methyl ester (100 mg, 0.27 mmol) in dioxane (5 mL) was added. The reaction mixture was stirred overnight at 85° C. The dioxane was removed by distillation. The remaining material was purified by chromatography (silica, ethyl acetate:heptane=2:3 to 3:2) to afford the title compound (30 mg, 27%) as a colourless oil. MS: m/e=416.2 [M+H]$^+$.

EXAMPLE 31

6-[3-(3,4-Difluoro-phenyl)-5-hydroxymethyl-isoxazol-4-ylmethoxy]-N-(2,2,2-trifluoro-ethyl)-nicotinamide

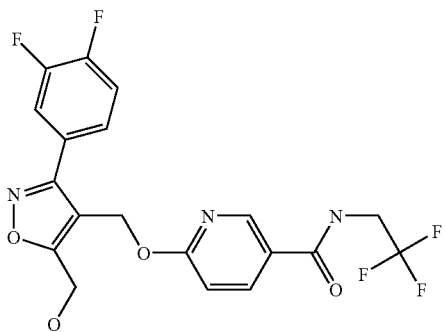

Trimethylaluminium solution (2M in toluene, 0.8 mL, 1.60 mmol) was added to a solution of 2,2,2,-trifluoroethylamine (108 mg, 1.06 mmol) in dioxane (5 mL). The mixture was stirred for 1 h at 50° C. Then a solution of 6-[3-(3,4-difluoro-phenyl)-5-hydroxymethyl-isoxazol-4-ylmethoxy]-nicotinic acid methyl ester (100 mg, 0.27 mmol) in dioxane (5 mL) was added. The reaction mixture was stirred overnight at 85° C. The dioxane was removed by distillation. The remaining material was purified by chromatography (silica, ethyl acetate:heptane=2:3 to 3:2) to afford the title compound (70 mg, 59%) as a white solid. MS: m/e=444.2 [M+H]⁺.

EXAMPLE 32

6-[3-(3,4-Difluoro-phenyl)-5-hydroxymethyl-isoxazol-4-ylmethoxy]-N-(2,2,2-trifluoro-1-methylethyl)-nicotinamide

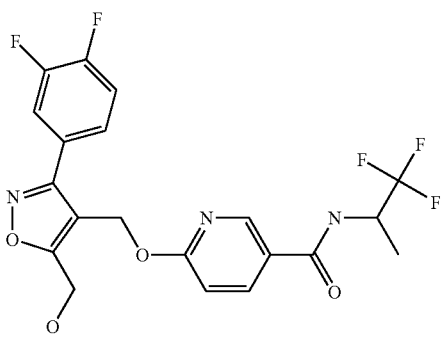

Trimethylaluminium solution (2 M in toluene, 0.8 mL, 1.60 mmol) was added to a solution of 1,1,1-trifluoro-isopropylamine (123 mg, 1.06 mmol) in dioxane (5 mL). The mixture was stirred for 1 h at 50° C. Then a solution of 6-[3-(3,4-difluoro-phenyl)-5-hydroxymethyl-isoxazol-4-ylmethoxy]-nicotinic acid methyl ester (100 mg, 0.27 mmol) in dioxane (5 mL) was added. The reaction mixture was stirred overnight at 85° C. The dioxane was removed by distillation. The remaining material was purified by chromatography (silica, ethyl acetate-heptane=2:3 to 3:2) to afford the title compound (65 mg, 53%) as a light brown solid. MS: m/e=458.1 [M+H]⁺.

EXAMPLE 33

N-Cyclopropyl-6-[3-(3,4-difluoro-phenyl)-5-hydroxymethyl-isoxazol-4-ylmethoxy]-nicotinamide

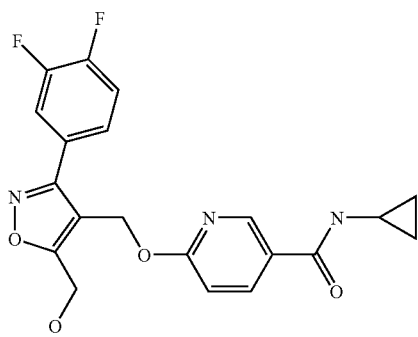

Trimethylaluminium solution (2 M in toluene, 0.8 mL, 1.60 mmol) was added to a solution of cyclopropylamine (62.0 mg, 1.06 mmol) in dioxane (5 mL). The mixture was stirred for 1 h at 50° C. Then a solution of 6-[3-(3,4-difluoro-phenyl)-5-hydroxymethyl-isoxazol-4-ylmethoxy]-nicotinic acid methyl ester (100 mg, 0.27 mmol) in dioxane (5 mL) was added. The reaction mixture was stirred overnight at 85° C. The dioxane was removed by distillation. The remaining material was purified by chromatography (silica, ethyl acetate:heptane=8:2 to 1:0) to afford the title compound (27 mg, 25%) as a colourless oil. MS: m/e=402.3 [M+H]⁺.

EXAMPLE 34

6-[3-(3,4-Difluoro-phenyl)-5-hydroxymethyl-isoxazol-4-ylmethoxy]-N-(2-hydroxy-1,1-dimethylethyl)-nicotinamide

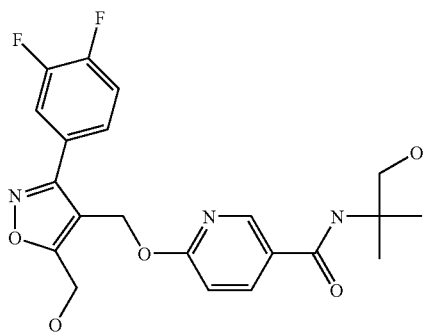

a) 6-[3-(3,4-Difluoro-phenyl)-5-hydroxymethyl-isoxazol-4-ylmethoxy]-nicotinic acid 6-[3-(3,4-Difluoro-phenyl)-5-hydroxymethyl-isoxazol-4-ylmethoxy]-nicotinic acid methyl ester (1.00 g, 2.66 mmol) in THF (6.25 mL), methanol (1.75 mL), and water (6.25 mL) was treated with lithium hydroxide (130 mg, 5.31 mmol) overnight at room temperature. Addition of aqueous hydrochloride solution (1 N, 100 mL) and extraction with ethyl acetate afforded the title compound (850 mg, 88%) as a white solid. MS: m/e=361.1 [M−H]⁻.

b) 6-[3-(3,4-Difluoro-phenyl)-5-hydroxymethyl-isoxazol-4-ylmethoxy]-N-(2-hydroxy-1,1-dimethylethyl)-nicotinamide To a solution of 6-[3-(3,4-difluoro-phenyl)-5-hydroxymethyl-isoxazol-4-ylmethoxy]-nicotinic acid (200 mg, 0.58 mmol) in THF (6 mL) were added 1-hydroxybenzotriazole hydrate (86.3 mg, 0.55 mmol), N-ethyldiisopropylamine (241 µL, 1.38 mmol), N-(3-dimethylaminopropyl)-N'-ethyl-carbodiimide hydrochloride (108 mg, 0.55 mmol) and 2-amino-2-methyl-1-propanol (50.7 mg, 0.55 mmol). The reaction mixture was stirred overnight at room temperature. Chromatography (silica, dichloromethane:methanol=0:100 to 95:5) afforded the title compound (120 mg, 50%) as a colourless oil. MS: m/e=434.4 [M+H]+.

EXAMPLE 35

6-[3-(3,4-Difluoro-phenyl)-5-hydroxymethyl-isoxazol-4-ylmethoxy]-N-(2,2,3,3,3-pentafluoro-propyl)-nicotinamide

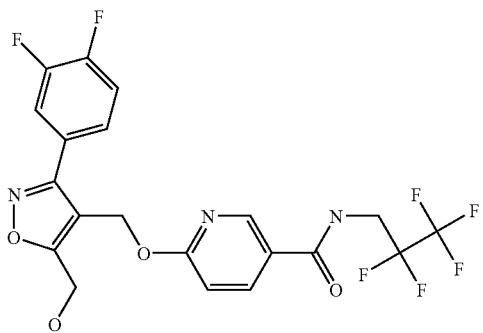

Trimethylaluminium solution (2M in toluene, 0.80 mL, 1.60 mmol) was added to a solution of 2,2,3,3,3-pentafluoropropylamine (116 µL, 1.10 mmol) in dioxane (4 mL). The mixture was stirred for 45 min at 50° C. Then a solution of 6-[3-(3,4-difluoro-phenyl)-5-hydroxymethyl-isoxazol-4-ylmethoxy]-nicotinic acid methyl ester (100 mg, 0.27 mmol) in dioxane (4 mL) was added and the reaction mixture was stirred overnight at 85° C. The dioxane was removed by distillation. The remaining material was purified by chromatography (silica, ethyl acetate:heptane=1:1) to afford the title compound (96 mg, 73%) as a white solid. MS: m/e=492.1 [M−H]−.

EXAMPLE 36

6-[3-(3,4-Difluoro-phenyl)-5-hydroxymethyl-isoxazol-4-ylmethoxy]-N-(2-methoxy-ethyl)-nicotinamide

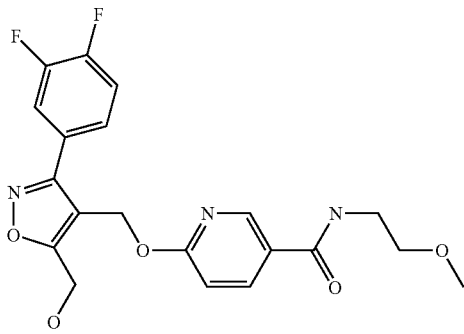

Trimethylaluminium solution (2 M in toluene, 0.80 mL, 1.60 mmol) was added to a solution of 2-methoxyethylamine (93.3 µL, 1.06 mmol) in dioxane (4 mL). The mixture was stirred for 45 min at 50° C. Then a solution of 6-[3-(3,4-difluoro-phenyl)-5-hydroxymethyl-isoxazol-4-ylmethoxy]-nicotinic acid methyl ester (100 mg, 0.27 mmol) in dioxane (4 mL) was added and the reaction mixture was stirred overnight at 85° C. The dioxane was removed by distillation. The remaining material was purified by chromatography (silica, ethyl acetate:heptane=2:3 to 1:0) to afford the title compound (14 mg, 13%) as a white solid. MS: m/e=418.2 [M−H]−.

EXAMPLE 37

6-[3-(3,4-Difluoro-phenyl)-5-hydroxymethyl-isoxazol-4-ylmethoxy]-N-([R]-1-hydroxymethyl-propyl)-nicotinamide

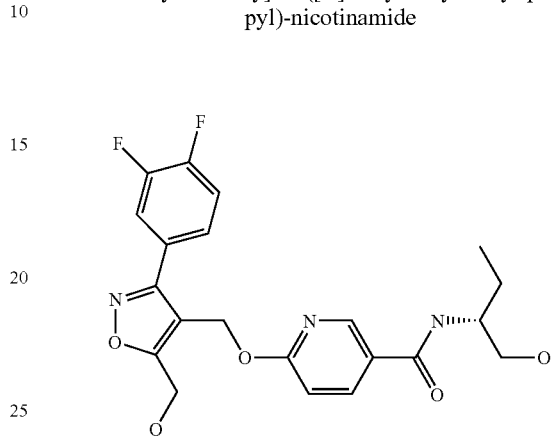

Hydroxybenzotriazole hydrate (43.1 mg, 0.28 mmol), N-ethyldiisopropylamine (241 µL, 1.38 mmol) and N-(3-dimethylaminopropyl)-N-ethylcarbodiimide hydrochloride (54.0 mg, 0.28 mmol) were added at 0° C. to a solution 6-[3-(3,4-difluoro-phenyl)-5-hydroxymethyl-isoxazol-4-ylmethoxy]-nicotinic acid (100 mg, 0.28 mmol) and [R]-(−)-2-amino-1-butanol (32.4 µL, 0.33 mmol) in THF (8 mL). The reaction mixture was stirred at room temperature overnight. Addition of aqueous hydrochloric acid (1 N, 10 mL), extraction with ethyl acetate and chromatography (silica, ethyl acetate:heptane=0:1 to 1:0) afforded the title compound (45 mg, 38%) as a white solid. MS: m/e=434.4 [M+H]+.

EXAMPLE 38

6-[3-(3,4-Difluoro-phenyl)-5-hydroxymethyl-isoxazol-4-ylmethoxy]-N-([S]-1-hydroxymethyl-propyl)-nicotinamide

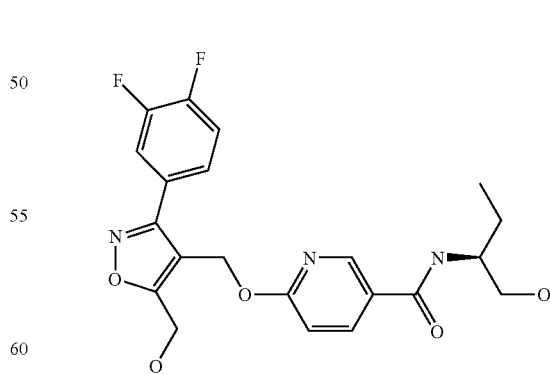

Hydroxybenzotriazole hydrate (43.1 mg, 0.28 mmol), N-ethyldiisopropylamine (241 µL, 1.38 mmol) and N-(3-dimethylaminopropyl)-N-ethylcarbodiimide hydrochloride (54.0 mg, 0.28 mmol) were added at 0° C. to a solution 6-[3-(3,4-difluoro-phenyl)-5-hydroxymethyl-isoxazol-4-ylmethoxy]-nicotinic acid (100 mg, 0.29 mmol) and [S]-(+)-2-amino-1-butanol (32.3 µL, 0.33 mmol) in THF (8 mL). The reaction mixture was stirred at room temperature overnight. Addition of aqueous hydrochloric acid (1 N, 10 mL), extraction with ethyl acetate and chromatography (silica, ethyl acetate:heptane=0:1 to 1:0) afforded the title compound (73 mg, 61%) as a brown solid. MS: m/e=434.4 [M+H]$^+$.

EXAMPLE 39

6-[3-(3,4-Difluoro-phenyl)-5-hydroxymethyl-isoxazol-4-ylmethoxy]-N-(1-methyl-1H-pyrazol-4-yl)-nicotinamide

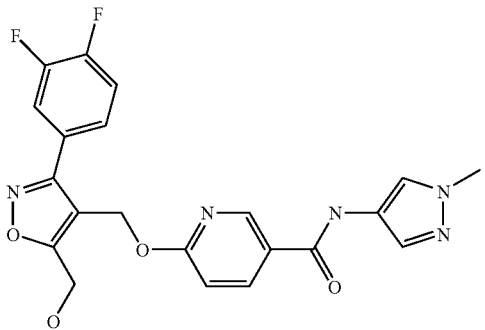

To a solution of 6-[3-(3,4-difluoro-phenyl)-5-hydroxymethyl-isoxazol-4-ylmethoxy]-nicotinic acid (100 mg, 0.28 mmol) in THF (3 mL) were added 1-hydroxybenzotriazole hydrate (43.1 mg, 0.28 mmol), N-ethyldiisopropylamine (120 µL, 0.69 mmol), N-(3-dimethylaminopropyl)-N'-ethylcarbodiimide hydrochloride (54.0 mg, 0.28 mmol) and 1-methyl-1H-pyrazol-4-ylamine (26.8 mg, 0.28 mmol). The reaction mixture was stirred overnight at room temperature. Chromatography (silica, ethyl acetate:heptane=2:1 to 9) afforded the title compound (3.5 mg, 3%) as a colourless oil. MS: m/e=442.2 [M+H]$^+$.

EXAMPLE 40

N-tert-Butyl-6-[3-(3,4-difluoro-phenyl)-5-hydroxymethyl-isoxazol-4-ylmethoxy]-nicotinamide

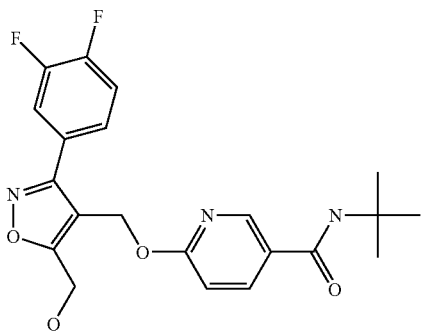

A trimethylaluminium solution (2 M in toluene, 798 µL, 1.6 mmol) in dioxane (7.5 mL) was added to tert-butylamine (174 µL, 1.6 mmol) and the mixture was stirred for 1 h at 50° C. 6-[3-(3,4-Difluoro-phenyl)-5-hydroxymethyl-isoxazol-4-ylmethoxy]-nicotinic acid methyl ester (150 mg, 0.4 mmol) in dioxane (7.5 mL) was added and stirring was continued overnight at 85° C. Chromatography (silica, ethyl acetate:heptane=1:4 to 1:1) afforded the title compound (20 mg, 13%) as a colourless solid. MS: m/e=416.4 [M–H]$^-$.

EXAMPLE 41

6-[3-(3,4-Difluoro-phenyl)-5-hydroxymethyl-isoxazol-4-ylmethoxy]-N-morpholin-4-yl-nicotinamide

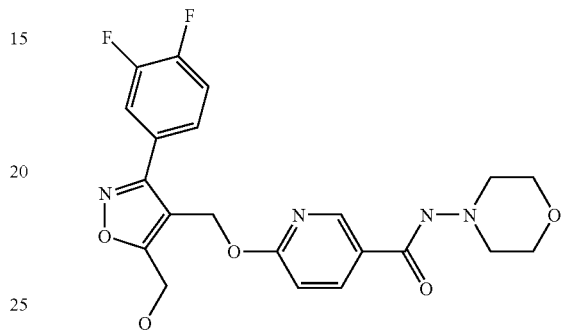

Hydroxybenzotriazole hydrate (64.7 mg, 0.41 mmol), N-ethyldiisopropylamine (181 ul, 1.04 mmol) and N-(3-dimethylaminopropyl)-N'-ethylcarbodiimide hydrochloride (81 mg, 0.41 mmol) were added to a mixture of 6-[3-(3,4-difluoro-phenyl)-5-hydroxymethyl-isoxazol-4-ylmethoxy]-nicotinic acid (150 mg, 0.41 mmol) and 4-aminomorpholine (41.5 µL, 0.41 mmol) in THF (15 mL) at room temperature. After stirring overnight the solvent was removed by distillation and the residue was purified by chromatography (silica, dichloromethane:methanol=98:2 to 95:5) afforded the title compound (130 mg, 70%) as a white solid. MS: m/e=445.2 [M–H]$^-$.

EXAMPLE 42

6-[3-(3,4-Difluoro-phenyl)-5-hydroxymethyl-isoxazol-4-ylmethoxy]-N-pyrrolidin-1-yl-nicotinamide

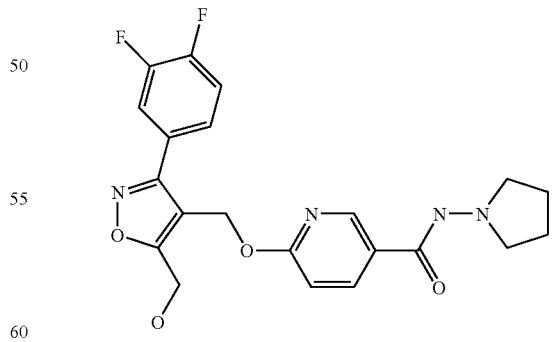

Hydroxybenzotriazole hydrate (64.7 mg; 0.41 mmol), N-ethyldiisopropylamine (181 µL, 1.04 mmol) and N-(3-dimethylaminopropyl)-N'-ethylcarbodiimide hydrochloride (81 mg, 0.41 mmol) were added to a mixture of 6-[3-(3,4-difluoro-phenyl)-5-hydroxymethyl-isoxazol-4-ylmethoxy]-nicotinic acid (150 mg, 0.41 mmol) and 1-aminopyrrolidine

EXAMPLE 43

(1,1-Dioxo-1,6-thiomorpholin-4-yl)-[6-(5-hydroxymethyl-3-pyridin-2-yl-isoxazol-4-ylmethoxy)-pyridin-3-yl]-methanone

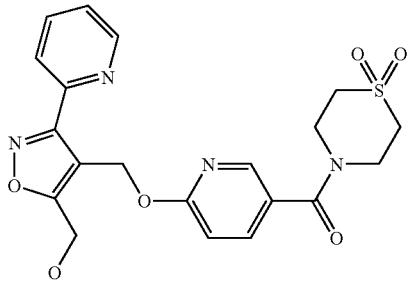

a) 5-Methyl-3-pyridin-2-yl-isoxazole-4-carboxylic acid ethyl ester

To a solution of N-chlorosuccinimide (46.58 g, 349 mmol) in chloroform (211 mL) and pyridine (2.8 mL, 35 mmol) was added at room temperature within 15 min a solution of pyridine-2-carbaldehyde oxime (42.6 g, 349 mmol) in chloroform (1090 mL). The reaction mixture was stirred at 50° C. for 3 h and then cooled to room temperature. Within 15 min a solution of (E)-3-pyrrolidin-1-yl-but-2-enoic acid ethyl ester (63.9 g, 349 mmol) in chloroform (42 mL) was added to the reaction mixture, which then was heated again to 50° C. and a solution of triethylamine (48.6 mL, 349 mmol) in chloroform (42 mL) was added dropwise within 1 h. After stirring at 50° C. for 1 h the reaction mixture was cooled to room temperature and then poured on ice water (2 L). Extractive workup followed by drying over sodium sulfate, filtering and evaporation of the organic solvent furnished a dark brown oil. Chromatographic purification (silica, heptane:AcOEt=80:20 to 50:50) afforded the title compound (8.7 g, 11%) as a yellow oil MS: m/e=233.3 [M+H]$^+$.

b) 3-Pyridin-2-yl-5-([E]-styryl)-isoxazole-4-carboxylic acid

To a solution of 5-methyl-3-pyridin-2-yl-isoxazole-4-carboxylic acid ethyl ester (3.0 g, 13 mmol) and benzaldehyde (1.32 mL, 13 mmol) in ethanol (20 mL) was added sodium ethylate (0.97 g, 14 mmol) and the reaction mixture was stirred at reflux for 40 min. Aqueous hydrochloric acid (1 M, 14 mL) was added and stirring was continued for 15 min. The precipitate was filtered and dried to afford the title compound (2.3 g, 61%) as an off-white solid. MS: m/e=290.9 [M−H]$^-$.

c) [3-Pyridin-2-yl-5-([E]-styryl)-isoxazol-4-yl]-methanol

To a solution of 3-pyridin-2-yl-5-([E]-styryl)-isoxazole-4-carboxylic acid (1.1 g, 4 mmol) and triethylamine (0.53 mL, 4 mmol) in THF (15 mL) was added dropwise at room temperature a solution of ethyl chloroformate (0.36 mL, 4 mmol) in THF (15 mL). After 1 h the triethylamine hydrochloride salt was filtered off and washed with a small amount of THF. The filtrate was added to a solution of sodium borohydride (0.36 g, 10 mmol) in water (10 mL). After stirring for 1 h at 5° C. aqueous sodium hydroxide (2 M, 22 mL) was added. Extraction with ethyl acetate, drying over sodium sulfate, filtering and evaporation of the solvent followed by trituration with diisopropylether afforded the title compound (0.76 g, 72%) as a white solid. MS: m/e=279.2 [M+H]$^+$.

d) 6-[3-Pyridin-2-yl-5-([E]-styryl)-isoxazol-4-ylmethoxy]-nicotinonitrile

To a solution of [3-pyridin-2-yl-5-([E]-styryl)-isoxazol-4-yl]-methanol (1.5 g, 5 mmol) in DMF (30 mL) was added 6-chloro-3-pyridine-carbonitrile (0.82 g, 6 mmol) and sodium hydride (0.26 g of a 55% dispersion in mineral oil, 6 mmol). The mixture was stirred at 70° C. for 3 h. Then the temperature was raised to 90° C. for 1 h. After evaporation of the solvent the residue was partitioned (ethyl acetate/brine) and the organic phase was dried (Na$_2$SO$_4$) and filtered. Evaporation of the solvent followed by trituration with diisopropylether afforded the title compound (1.8 g, 88%) as a light brown solid. MS: m/e=381.3 [M+H]$^+$.

e) 6-(5-Formyl-3-pyridin-2-yl-isoxazol-4-yl-methoxy)-nicotinonitrile

A mixture of 6-[3-pyridin-2-yl-5-((E)-styryl)-isoxazol-4-ylmethoxy]-nicotinonitrile (0.57 g, 2 mmol), osmium(VIII) oxide solution (0.38 mL of a 2.5% solution in tert-butanol, 0.04 mmol), sodium metaperiodate (1.29 g, 6 mmol), benzyltriethylammonium chloride (0.14 g, 0.6 mmol) in dioxane (13 mL) and water (4.5 mL) was heated in a microwave for 45 min at 120° C. Extractive workup (ethyl acetate/water) was followed by drying of the organic phase over sodium sulfate and filtering. The solvent was evaporated and the residue was triturated with diisopropylether to afford the title compound (0.23 g, 51%) as a white solid. MS: m/e=307.2 [M+H]$^+$.

f) 6-(5-Hydroxymethyl-3-pyridin-2-yl-isoxazol-4-ylmethoxy)-nicotinonitrile

A suspension of 6-(5-formyl-3-pyridin-2-yl-isoxazol-4-ylmethoxy)-nicotinonitrile (0.77 g, 2.5 mmol) in methanol (20 mL) was cooled in an ice bath and treated with sodium borohydride (0.29 g, 7.7 mmol). The reaction mixture was allowed to reach room temperature and was stirred for 72 h. Additional sodium borohydride (0.29 g, 7.7 mmol) was added and stirring at room temperature was continued for 3 h. After quenching with methanol all volatile components were evaporated. The residue was partitioned (ethyl acetate/brine). The organic layer was dried (Na$_2$SO$_4$), filtered and concentrated to afford the title compound (0.73 g, 94%) as a brown solid. MS: m/e=309.2 [M+H]$^+$.

g) 6-(5-Hydroxymethyl-3-pyridin-2-yl-isoxazol-4-ylmethoxy)-nicotinic acid 6-(5-Hydroxymethyl-3-pyridin-2-yl-isoxazol-4-ylmethoxy)-nicotinonitrile (0.88 g, 2.9 mmol) was dissolved in ethanol (30 mL). Aqueous sodium hydroxide (4 M, 30 mL) was added and the mixture was stirred at 50° C. for 2 h. The mixture was evaporated to half its original volume and aqueous hydrochloric acid (2 M, 30 mL) was added. After stirring (51.8 mg, 0.41 mmol) in THF (15 mL) at room temperature. After stirring overnight the solvent was removed by distillation and the residue was purified by chromatography (silica, dichloromethane:methanol=98:2 to 95:5) afforded the title compound (150 mg, 84%) as a white solid. MS: m/e=429.1 [M−H]$^-$.

overnight the precipitate was filtered and dried to afford the title compound (0.58 g, 62%) as a white solid. MS: m/e=328.2 [M+H]⁺.

h) (1,1-Dioxo-1,6-thiomorpholin-4-yl)-[6-(5-hydroxymethyl-3-pyridin-2-yl-isoxazol-4-ylmethoxy)-pyridin-3-yl]-methanone To a solution of 6-(5-hydroxymethyl-3-pyridin-2-yl-isoxazol-4-ylmethoxy)-nicotinic acid (70 mg, 0.21 mmol) in DMF (5 mL) was added thiomorpholine 1,1-dioxide (40 mg, 0.30 mmol), N,N,N',N'-tetramethyl-O-(benzotriazole-1-yl)-uronium tetrafluoroborate (96 mg, 0.30 mmol) and N,N-diisopropyl ethylamine (0.15 mL, 0.84 mmol). The reaction mixture was stirred overnight at room temperature. After evaporation of the solvent the residue was partitioned (ethyl acetate/aqueous saturated sodium bicarbonate solution) and the organic phase was dried (Na₂SO₄) and concentrated. Chromatography (silica, dichloromethane:methanol=1000:0 to 975:25) afforded the title compound (58 mg, 61%) as a white solid. MS: m/e=445.3 [M+H]⁺.

EXAMPLE 44

6-(5-Hydroxymethyl-3-pyridin-2-yl-isoxazol-4-ylmethoxy)-N-isopropyl-nicotinamide

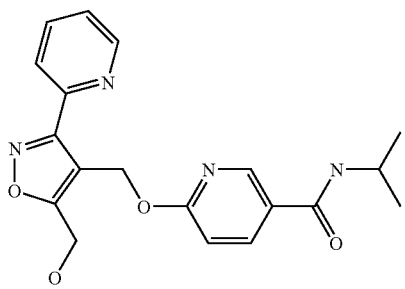

To a solution of 6-(5-hydroxymethyl-3-pyridin-2-yl-isoxazol-4-ylmethoxy)-nicotinic acid (70 mg, 0.21 mmol) in DMF (5 mL) was added isopropylamine (18 mg, 0.30 mmol), N,N,N',N'-tetramethyl-O-(benzotriazole-1-yl)-uronium tetrafluoroborate (0.096 g, 0.30 mmol) and N,N-diisopropylethylamine (0.15 mL, 0.84 mmol). The reaction mixture was stirred overnight at room temperature. After evaporation of the solvent the residue was partitioned (ethyl acetate/aqueous saturated sodium bicarbonate solution) and the organic phase was dried (Na₂SO₄), filtered and concentrated. Chromatography (silica, dichloromethane:methanol=100:0 to 97:3) afforded the title compound (51 mg, 65%) as a colorless oil. MS: m/e=369.1 [M+H]⁺.

EXAMPLE 45

6-(5-Hydroxymethyl-3-pyridin-2-yl-isoxazol-4-ylmethoxy)-N-(tetrahydrofuran-3-yl)-nicotinamide

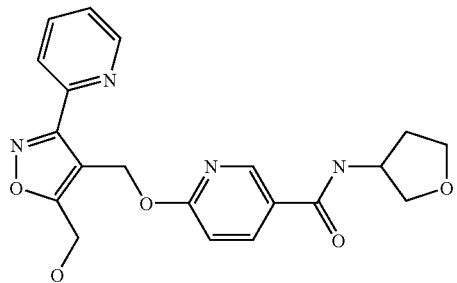

To a solution of 6-(5-hydroxymethyl-3-pyridin-2-yl-isoxazol-4-ylmethoxy)-nicotinic acid (70 mg, 0.21 mmol) in DMF (5 mL) was added 3-aminotetrahydrofuran (26 mg, 0.30 mmol), N,N,N',N'-tetramethyl-O-(benzotriazole-1-yl)-uronium tetrafluoroborate (96 mg, 0.30 mmol) and N,N-diisopropyl ethylamine (0.15 mL, 0.84 mmol). The reaction mixture was stirred overnight at room temperature. After evaporation of the solvent the residue was partitioned (ethyl acetate/aqueous saturated sodium bicarbonate solution) and the organic phase was dried (Na₂SO₄) and concentrated. Chromatography (silica, dichloromethane:methanol=100:0 to 97:3) afforded the title compound (58 mg, 68%) as a colorless oil. MS: m/e=397.1 [M+H]⁺.

EXAMPLE 46

6-(5-Hydroxymethyl-3-pyridin-2-yl-isoxazol-4-ylmethoxy)-nicotinic acid N',N'-dimethyl-hydrazide

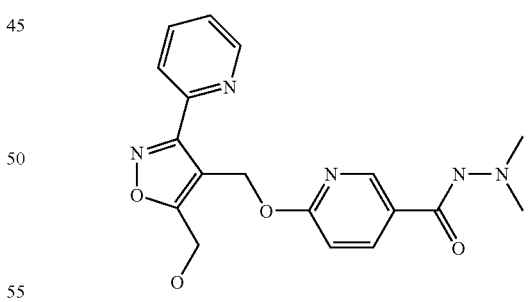

To a solution of 6-(5-hydroxymethyl-3-pyridin-2-yl-isoxazol-4-ylmethoxy)-nicotinic acid (70 mg, 0.21 mmol) in DMF (5 mL) was added N,N-dimethylhydrazine (18 mg, 0.30 mmol), N,N,N',N'-tetramethyl-O-(benzotriazole-1-yl)-uronium tetrafluoroborate (96 mg, 0.30 mmol) and N,N-diisopropyl ethylamine (0.15 mL, 0.84 mmol). The reaction mixture was stirred overnight at room temperature. After evaporation of the solvent the residue was partitioned (ethyl acetate/aqueous saturated sodium bicarbonate solution) and the organic phase was dried (Na₂SO₄), filtered and concentrated. Chromatography (silica, dichloromethane:metha-

EXAMPLE 47

6-(5-Hydroxymethyl-3-pyridin-2-yl-isoxazol-4-yl-methoxy)-N-(tetrahydropyran-4-yl)-nicotinamide

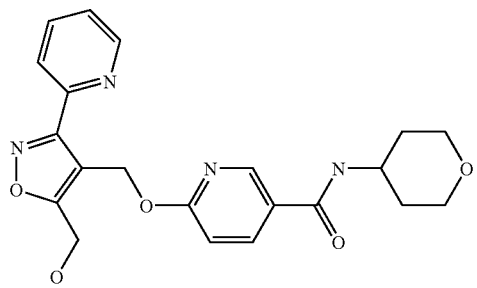

To a solution of 6-(5-hydroxymethyl-3-pyridin-2-yl-isoxazol-4-ylmethoxy)-nicotinic acid (70 mg, 0.21 mmol) in DMF (5 mL) was added 4-aminotetrahydropyrane (30 mg, 0.30 mmol), N,N,N',N'-tetramethyl-O-(benzotriazole-1-yl)-uronium tetrafluoroborate (96 mg, 0.30 mmol) and N,N-diisopropyl ethylamine (0.15 mL, 0.84 mmol). The reaction mixture was stirred overnight at room temperature. After evaporation of the solvent the residue was partitioned (ethyl acetate/aqueous saturated sodium bicarbonate solution) and the organic phase was dried (Na$_2$SO$_4$) and concentrated. Chromatography (silica, dichloromethane:methanol=100:0 to 97:3) afforded the title compound (42 mg, 48%) as a white solid. MS: m/e=411.2 [M+H]$^+$.

EXAMPLE 48

6-(5-Hydroxymethyl-3-pyridin-2-yl-isoxazol-4-yl-methoxy)-N-morpholin-4-yl-nicotinamide

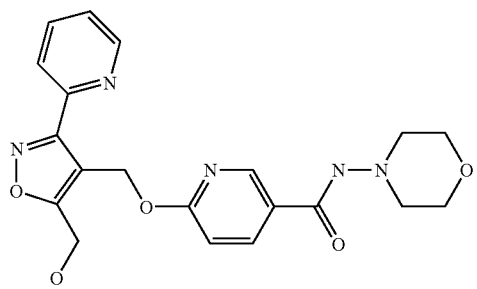

To a solution of 6-(5-hydroxymethyl-3-pyridin-2-yl-isoxazol-4-ylmethoxy)-nicotinic acid (70 mg, 0.21 mmol) in DMF (5 mL) was added 4-aminomorpholine (31 mg, 0.30 mmol), N,N,N',N'-tetramethyl-O-(benzotriazole-1-yl)-uronium tetrafluoroborate (96 mg, 0.30 mmol) and N,N-diisopropyl ethylamine (0.15 mL, 0.84 mmol). The reaction mixture was stirred overnight at room temperature. After evaporation of the solvent the residue was partitioned (ethyl acetate/aqueous saturated sodium bicarbonate solution) and the organic phase was dried (Na$_2$SO$_4$) and concentrated. Chromatography (silica, dichloromethane:methanol=100:0 to 97:3) afforded the title compound (41 mg, 47%) as a colorless oil. MS: m/e=412.2 [M+H]$^+$.

EXAMPLE 49

6-(3-Butyl-5-hydroxymethyl-isoxazol-4-ylmethoxy)-N-isopropyl-nicotinamide

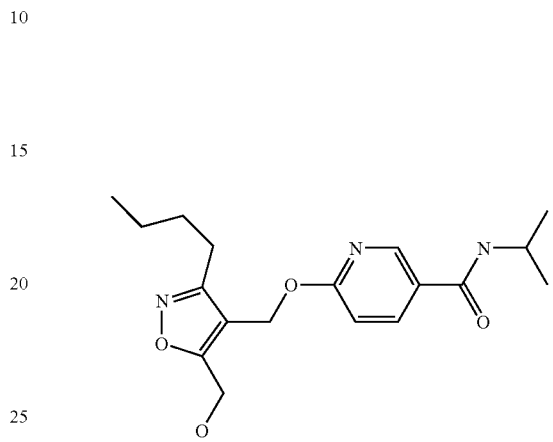

To a solution of 6-[3-butyl-5-hydroxymethyl-isoxazol-4-ylmethoxy]-nicotinic acid methyl ester (100 mg, 0.31 mmol) in toluene (1 mL) was added isopropylamine (55 mg, 0.93 mmol) and 1,5,7-triazabicyclo[4.4.0]dec-5-ene (26 mg, 0.19 mmol). The reaction mixture was stirred for 3.5 days at 50° C. A further portion of isopropylamine was added and the reaction was heated at 50° C. for an additional 3.5 days. Dichloromethane (40 mL) was added and the reaction mixture was concentrated in vacuo onto silica gel and purified by chromatography (silica, dichloromethane:methanol 1:0 to 9:1) to afford the title compound (18 mg, 17%) as a colorless oil. MS: m/e=348.3 [M+H]$^+$.

EXAMPLE 50

6-(3-Butyl-5-hydroxymethyl-isoxazol-4-ylmethoxy)-N-(3-methyloxetan-3-yl)-nicotinamide

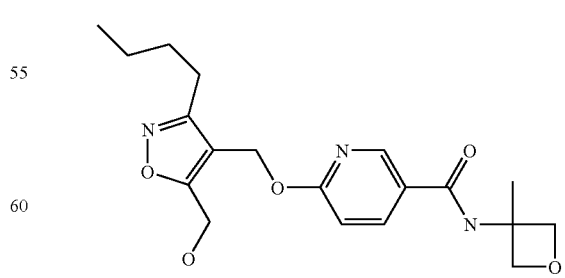

As described in example 52g, 6-[3-butyl-5-hydroxymethyl-isoxazol-4-ylmethoxy]-nicotinic acid (49 mg, 0.16 mmol) was converted, using 3-methyl 3-oxetanamine instead of cyclobutylamine, to the title compound (29 mg, 48%) which was obtained as a colorless oil. MS: m/e=376.3 [M+H]+.

EXAMPLE 51

6-(3-Butyl-5-hydroxymethyl-isoxazol-4-ylmethoxy)-N-(2,2,2-trifluoroethyl)-nicotinamide

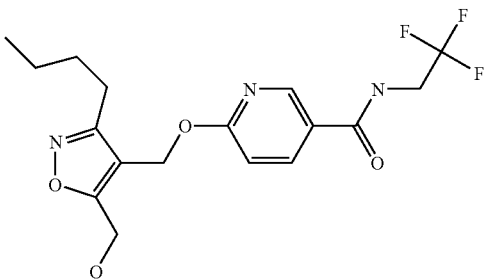

As described in example 53g, 6-[3-butyl-5-hydroxymethyl-isoxazol-4-ylmethoxy]-nicotinic acid (49 mg, 0.16 mmol) was converted, using 2,2,2-trifluoroethylamine hydrochloride instead of cyclobutylamine, to the title compound (11 mg, 18%) which was obtained as a colorless oil. MS: m/e=388.2 [M+H]+.

EXAMPLE 52

6-(3-Butyl-5-hydroxymethyl-isoxazol-4-ylmethoxy)-N-cyclobutyl-nicotinamide

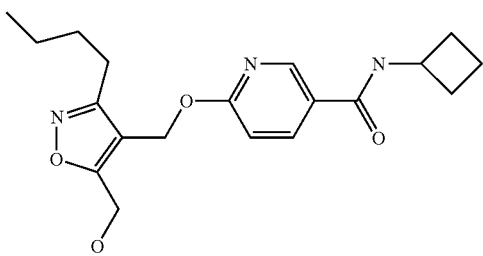

a) 3-Butyl-5-([E]-styryl)-isoxazole-4-carboxylic acid

To a solution of 3-butyl-5-methyl-isoxazole-4-carboxylic acid ethyl ester (15.0 g, 71.0 mmol) and benzaldehyde (7.2 mL, 71.0 mmol) in ethanol (100 mL) was added sodium ethoxide solution (21% in ethanol, 29.1 mL, 78.0 mmol) and the reaction mixture was stirred at reflux for 2 h, cooled to room temperature and stirred for 17 h. Hydrochloric acid (1 N, 85 mL) was added and the resulting mixture was extracted twice with dichloromethane. The combined phases were washed with brine, dried over sodium sulfate and filtered. The filtrate was concentrated to a bright yellow pasty solid and recrystallized from hot heptane/ethyl acetate to afford the title compound (8.0 g, 42%) as a yellow solid. MS: m/e=270.4 [M-H]−.

b) [3-Butyl-5-([E]-styryl)-isoxazol-4-yl]-methanol

To a solution of 3-butyl-5-([E]-styryl)-isoxazole-4-carboxylic acid (7.0 g, 25.8 mmol) and triethylamine (3.8 mL, 27.0 mmol) in THF (30 mL) was added at 0° C. ethyl chloroformate (2.6 mL, 27.0 mmol). After 1 h the triethylamine hydrochloride salt was filtered off and washed with a small amount of THF. The filtrate was concentrated, the residue taken up in ethanol (70 mL) and added to a solution of sodium borohydride (2.4 g, 63.4 mmol) in water (35 mL) at 0° C. After stirring at room temperature for 2.5 days, the reaction was quenched with aqueous sodium hydroxyde (1 M, 40 mL) and extracted twice with tert-butylmethylether. The combined phases were washed with brine, dried over sodium sulfate and filtered. The filtrate was concentrated to a yellow oil and purified by flash chromatography (silica, dichloromethane:methanol 100:0 to 97:3) to afford the title compound (6.9 g, 98%) as an orange oil. MS: m/e=258.1 [M+H]+.

c) 6-[3-Butyl-5-([E]-styryl)-isoxazol-4-ylmethoxy]-nicotinic acid methyl ester

To a suspension of sodium hydride (170 mg, 4.24 mmol) in THF (7 mL) at 0° C. was added a solution of [3-butyl-5-([E]-styryl)-isoxazol-4-yl]-methanol (993 mg, 3.86 mmol) in THF (17 mL) and the mixture was stirred for 30 min at room temperature. The reaction mixture was cooled to 5° C. and a solution of methyl 6-bromonicotinate (1.0 g, 4.6 mmol) in THF (17 mL) was added dropwise. The mixture was stirred at room temperature for 2 days, poured over ice and stirred for 5 min. The mixture was extracted twice with ethyl acetate, washed with brine, dried over sodium sulfate and concentrated to a yellow oily solid. The crude material was purified by flash chromatography (silica gel, heptane:ethyl acetate 1:0 to 3:2) to afford the title compound (1.17 g, 77%) as an orange semisolid. MS: m/e=393.2 [M+H]+.

d) 6-[3-Butyl-5-(1,2-dihydroxy-2-phenylethyl)-isoxazol-4-ylmethoxy]-nicotinic acid methyl ester To a solution of 6-[3-butyl-5-([E]-styryl)-isoxazol-4-ylmethoxy]-nicotinic acid methyl ester (1.4 g, 3.7 mmol) in tert-butanol (100 mL) was added methanesulfonamide (356 mg, 3.7 mmol) and AD Mix-α (5.2 g) with water (100 mL). The reaction mixture was stirred at room temperature for 17 h and extracted with ethyl acetate. The combined organic phases were washed with brine, dried over sodium sulfate and concentrated to a yellow oil. The crude material was purified by flash chromatography (silica gel, heptane:ethyl acetate 3:2 to 1:1) to afford the title compound (890 mg, 56%) as a colourless oil. MS: m/e=427.2 [M+H]+.

e) 6-[3-Butyl-5-hydroxymethyl-isoxazol-4-ylmethoxy]-nicotinic acid methyl ester

To a solution of 6-[3-butyl-5-(1,2-dihydroxy-2-phenylethyl)-isoxazol-4-ylmethoxy]-nicotinic acid methyl ester (890 mg, 2.09 mmol) in benzene (10 mL) was added lead tetraacetate (1.39 g, 3.13 mmol) with benzene (5 mL) and the reaction was stirred at room temperature for 45 min. The suspension was filtered over celite and the filtrate was concentrated to a yellow oil. The oil was taken up in methanol (20 mL) and sodium borohydride (198 mg, 5.24 mmol) was added in portions over 3 min. Upon addition, the reaction became a clear light yellow solution containing a black precipitate. After stirring at room temperature for 15 min, the mixture was filtered over celite and the filter cake was washed with methanol. The filtrate was concentrated and the residue was portioned between 0.5M aqueous hydrochloric acid and ethyl acetate. The aqueous phase was extracted two times with ethyl acetate and the combined organic phases were washed with brine, dried over sodium sulfate and concentrated to a yellow oil. The crude material was purified by chromatography (silica, heptane:ethyl acetate 1:0 to 1:1) to afford the title compound (495 mg, 68%) as a colorless oil. MS: m/e=321.2 [M+H]+.

f) 6-[3-Butyl-5-hydroxymethyl-isoxazol-4-yl-methoxy]-nicotinic acid

To a solution of 6-[3-butyl-5-hydroxymethyl-isoxazol-4-ylmethoxy]-nicotinic acid methyl ester (490 mg, 1.53 mmol) in dioxane (20 mL) was added aqueous sodium hydroxide (2 M, 10 mL) and the reaction mixture was stirred at 90° C. for 17 h. The mixture was concentrated and the residue was acidified with aqueous hydrochloric acid (2 M, 15 mL) and extracted twice with ethyl acetate. The combined organic phases were washed with brine, dried over sodium sulfate and concentrated to a yellow oil to afford the title compound (480 mg, 100%). MS: m/e=305.4 [M−H]−.

g) 6-(3-Butyl-5-hydroxymethyl-isoxazol-4-yl-methoxy)-N-cyclobutyl-nicotinamide To a solution of 6-[3-butyl-5-hydroxymethyl-isoxazol-4-ylmethoxy]-nicotinic acid (49 mg, 0.16 mmol) in DMF (2 mL) was added cyclobutylamine (25 mg, 0.35 mmol), O-(benzotriazol-1-yl)-N,N,N',N'-tetramethyluronium tetrafluoroborate (82 mg, 0.26 mmol) and N-ethyldiisopropylamine (136 μL, 0.80 mmol) with DMF (1 mL). The reaction mixture was stirred for 17 h at room temperature. The reaction was partitioned between water and ethyl acetate. The aqueous phase was extracted two times with ethyl acetate and the combined organic phases were washed with brine, dried over sodium sulfate and concentrated to a yellow oil. The crude material was purified by chromatography (silica, dichloromethane:methanol 100:0 to 97:3) to afford the title compound (36 mg, 63%) as a colorless gum. MS: m/e=360.3 [M+H]+.

EXAMPLE 53

Azetidin-1-yl-[6-(3-Butyl-5-hydroxymethyl-isoxazol-4-ylmethoxy)-pyridin-3-yl]-methanone

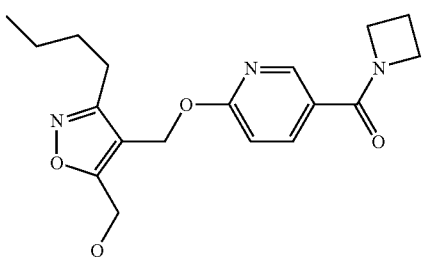

As described in example 52g, 6-[3-butyl-5-hydroxymethyl-isoxazol-4-ylmethoxy]-nicotinic acid (49 mg, 0.16 mmol) was converted, using trimethylene instead of cyclobutylamine, to the title compound (28 mg, 50%) which was obtained as a colorless oil. MS: m/e=346.1 [M+H]+.

EXAMPLE 54

[6-(5-Hydroxymethyl-3-pyridin-2-yl-isoxazol-4-ylmethoxy)-pyridin-3-yl]-morpholin-4-yl-methanone

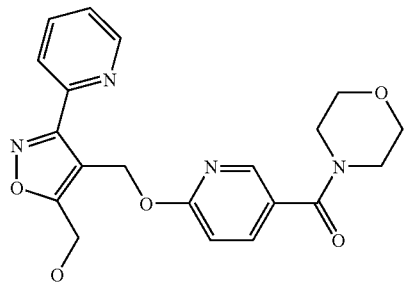

As described in example 43h, 6-(5-hydroxymethyl-3-pyridin-2-yl-isoxazol-4-ylmethoxy)-nicotinic acid (881 mg, 2.7 mmol) was converted, using morpholine instead of thiomorpholine 1,1-dioxide, to the title compound (738 mg, 69%) which was obtained as a white foam. MS: m/e=397.3 [M+H]+.

EXAMPLE 55

[6-(3-Butyl-5-hydroxymethyl-isoxazol-4-yl-methoxy)-pyridin-3-yl]-(1,1-dioxo-thiomorpholin-4-yl)-methanone

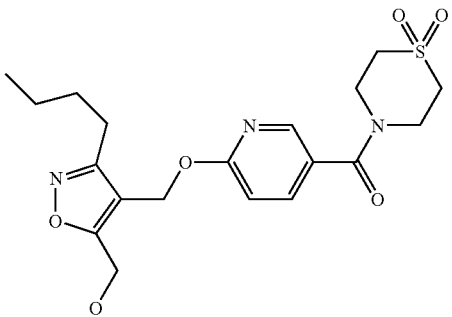

As described in example 52g, 6-[3-butyl-5-hydroxymethyl-isoxazol-4-ylmethoxy]-nicotinic acid (45 mg, 0.15 mmol) was converted, using thiomorpholine-1,1-dioxide

EXAMPLE 56

(1,1-Dioxo-1,6-thiomorpholin-4-yl)-{6-[3-(5-fluoro-pyridin-2-yl)-5-hydroxymethyl-isoxazol-4-yl-methoxy]-pyridin-3-yl}-methanone

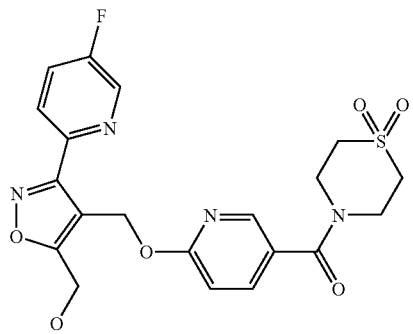

5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]⁺.

b) 3-(5-Fluoro-pyridin-2-yl)-5-methyl-isoxazole-4-carboxylic acid ethyl ester To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl (E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (SiO₂, heptane:ethyl acetate=100:0 to 20:80) afforded the title compound (5.83 g, 67%) as yellow oil. MS: m/e=251.1 [M+H]⁺.

c) (E)-3-(5-Fluoropyridin-2-yl)-5-styrylisoxazole-4-carboxylic acid

To a solution of 3-(5-Fluoro-pyridin-2-yl)-5-methyl-isoxazole-4-carboxylic acid ethyl ester (1.05 g, 4.2 mmol) and benzaldehyde (0.42 mL, 4.2 mmol) in ethanol (6 mL) was added sodium ethylate (1.5 g, 4.6 mmol) and the reaction mixture was stirred at reflux for 30 min. Aqueous hydrochloric acid (1 M, 5 mL) was added and stirring was continued for 15 min. The precipitate was filtered and dried to afford the title compound (1.2 g, 85%) as an off-white solid. MS: m/e=309.3 [M−H]⁻.

d) (E)-(3-(5-Fluoropyridin-2-yl)-5-styrylisoxazol-4-yl)methanol

To a solution of (E)-3-(5-fluoropyridin-2-yl)-5-styrylisoxazole-4-carboxylic acid (1.2 g, 3.7 mmol) and triethylamine (0.52 mL, 3.7 mmol) in THF (30 mL) was added dropwise at room temperature a solution of ethyl chloroformate (0.36 mL, 3.7 mmol) in THF (4 mL). After 1 h the triethylamine hydrochloride salt was filtered off and washed with a small amount of THF. The filtrate was added to a solution of sodium borohydride (354 mg, 9.4 mmol) in water (3.5 mL). After stirring for 1 h at 5° C. aqueous sodium hydroxide (1 M, 11 mL) was added. Extraction with ethyl acetate, drying over sodium sulfate, filtering and evaporation of the solvent followed by trituration with diisopropylether afforded the title compound (895 mg, 81%) as a white solid after purification by chromatography (SiO₂, DCM). MS: m/e=297.2 [M+H]⁺.

e) (E)-Methyl 6-((3-(5-fluoropyridin-2-yl)-5-styryl-isoxazol-4-yl)methoxy)nicotinate To a suspension of sodium hydride (129 mg, 3.22 mmol) in THF (4.5 mL) was added a solution of (E)-(3-(5-fluoropyridin-2-yl)-5-styrylisoxazol-4-yl)methanol (866 mg, 2.92 mmol) in THF (9 mL) at room temperature. The reaction mixture was stirred for 1 h at room temperature. A solution of methyl 6-chloronicotinate (602 mg, 3.51 mmol) in THF (9 mL) was added. The reaction was stirred at room temperature overnight and water (150 mL) and saturated aqueous ammonium chloride solution (100 mL) were added. Extraction with ethyl acetate and chromatography (silica, ethyl acetate:heptane=1:9 to 2:3) afforded the title compound (906 mg, 66%) as a white solid. MS: m/e=432.2 [M+H]⁺.

f) Methyl 6-((3-(5-flouropyridin-2-yl)-5-formylisoxazol-4-yl)methoxy)nicotinate A mixture of methyl 6-((3-(5-fluoropyridin-2-yl)-5-formylisoxazol-4-yl)methoxy)nicotinate (100 mg, 0.23 mmol), osmium(VIII) oxide solution (0.55 mL of a 4% solution in water, 0.7 mmol), sodium metaperiodate (198 mg, 0.93 mmol), benzyltriethylammonium chloride (21.1 mg, 0.93 mmol) in dioxane (1.8 mL) and water (0.6 mL) was heated in a microwave for 25 min at 120° C. Extractive workup (ethyl acetate/water) was followed by drying of the organic phase over sodium sulfate and filtering. The solvent was evaporated and the residue was triturated with diisopropylether to afford the title compound (58 mg, 63%) as a white solid. MS: m/e=358.1 [M+H]⁺.

g) Methyl 6-((3-(5-fluoropyridin-2-yl)-5-(hydroxymethyl)isoxazol-4-1 methoxy)nicotinate Sodium borohydride (4.8 mg, 0.13 mmol) was added in portions to methyl 6-((3-(5-fluoropyridin-2-yl)-5-formylisoxazol-4-yl)methoxy)nicotinate (91 mg, 0.26 mmol) in methanol (5 mL). After stirring overnight at room temperature a solution of citric acid (10% in water) was added. Extraction with ethyl acetate and chromatography (silica, dicholoromethane:methanol=1:0 to 9:1) afforded the title compound (89 mg, 88%) as a white solid. MS: m/e=360.1 [M+H]⁺.

h) 6-((3-(5-fluoropyridin-2-yl)-5-(hydroxymethyl) isoxazol-4-yl)methoxy)nicotinic acid To methyl 6-((3-(5-fluoropyridin-2-yl)-5-(hydroxymethyl)isoxazol-4-yl)methoxy)nicotinate (450 mg, 1.25 mmol) in THF (14 mL), methanol (4 mL) and water (05 mL) was added lithium hydroxide (105 mg, 2.5 mmol). The reaction mixture was stirred for 1 h at room temperature. A precipitate formed upon addition of aqueous hydrochloride solution (1 N, to ~pH 4). Filtration and drying afforded the title compound (411 mg, 95%) as a white solid. MS: m/e=344.1 [M–H]⁻.

i) (1,1-Dioxo-1,6-thiomorpholin-4-yl)-{6-[3-(5-fluoro-pyridin-2-yl)-5-hydroxymethyl-isoxazol-4-ylmethoxy]-pyridin-3-yl}-methanone To a solution of 6-((3-(5-fluoropyridin-2-yl)-5-(hydroxymethyl)isoxazol-4-yl)methoxy)nicotinic acid (384 mg, 1.11 mmol) in DMF (10 mL) was added thiomorpholine 1,1-dioxide (165 mg, 1.22 mmol), N,N,N',N'-tetramethyl-O-(benzotriazole-1-yl)-uronium tetrafluoroborate (393 mg, 1.22 mmol) and N,N-diisopropyl ethylamine (0.95 mL, 5.56 mmol). The reaction mixture was stirred for 30 min at room temperature. After evaporation of the solvent the residue purified by chromatography (silica, ethylacetate:heptane=1:1 to 1:0) to afford the title compound (422 mg, 82%) as a white solid. MS: m/e=463.2 [M+H]⁺.

The invention claimed is:
1. A compound of formula I

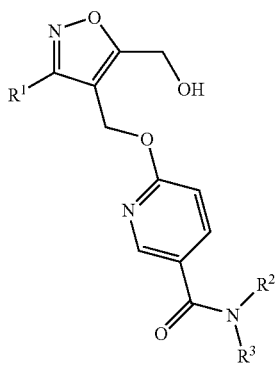

wherein
$R^1$ is lower-alkyl, aryl or heteroaryl,
wherein lower-alkyl is optionally substituted with 1-4 substituents independently selected from the group consisting of halogen, cyano, hydroxy and lower-alkoxy,
and wherein aryl and heteroaryl are optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—NH$_2$, lower-alkyl-CO—N(H,lower-alkyl), lower-alkyl-CO—N(lower-alkyl)$_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, CONH$_2$, CON(H,lower-alkyl), CON(lower-alkyl)$_2$, cycloalkyl, heterocyclyl, aryl, heteroaryl, NH$_2$, N(H, lower-alkyl), N(lower-alkyl)$_2$, hydroxy, lower-alkoxy, phenyloxy, SO$_2$-lower-alkyl, SO$_2$—NH$_2$, SO$_2$—N(H,lower-alkyl) and SO$_2$—N(lower-alkyl)$_2$;

$R^2$ is hydrogen or lower-alkyl;
$R^3$ is lower-alkyl, lower-alkyl substituted by halogen, lower-alkyl substituted by hydroxy, cycloalkyl, cycloalkyl substituted by hydroxy, heterocyclyl, heterocyclyl substituted by lower-alkyl, heteroaryl, heteroaryl substituted by lower-alkyl, (CH$_2$)$_n$—O-lower-alkyl or NR$^4$R$^5$;
or wherein $R^2$ and $R^3$, together with the nitrogen atom to which they are attached, form a heterocyclyl;
n is 1 or 2;
$R^4$ and $R^5$ are each independently selected from hydrogen and lower-alkyl;
or a pharmaceutically acceptable salt or ester thereof.

2. The compound of claim 1, wherein $R^1$ is lower-alkyl, aryl, aryl substituted with 1 or 2 halogen, heteroaryl or heteroaryl substituted with halogen.

3. The compound of claim 2, wherein $R^1$ is phenyl substituted with 1 or 2 halogen or pyridinyl.

4. The compound of claim 2, wherein $R^1$ is n-butyl, phenyl, 4-chloro-phenyl, 4-fluoro-phenyl, 3,4-difluoro-phenyl, pyridine-2-yl or 5-fluoro-pyridin-2-yl.

5. The compound of claim 3, wherein $R^1$ is 4-chloro-phenyl, 4-fluoro-phenyl or pyridine-2-yl.

6. The compound of claim 1, wherein $R^2$ is hydrogen or lower-alkyl.

7. The compound of claim 6, wherein $R^2$ is hydrogen.

8. The compound of claim 1, wherein $R^3$ is lower-alkyl, lower-alkyl substituted by halogen, lower-alkyl substituted by hydroxy, cycloalkyl, cycloalkyl substituted by hydroxy, heterocyclyl, heterocyclyl substituted by lower-alkyl, heteroaryl, heteroaryl substituted by lower-alkyl, (CH$_2$)$_n$—O-lower-alkyl or NR$^4$R$^5$.

9. The compound of claim 8, wherein $R^3$ is methyl, isopropyl, tert-butyl, cyclopropylmethyl, 2,2,2-trifluoro-ethyl, 2,2,3,3,3-pentafluoro-propyl, 2,2,2-trifluoro-1-methyl-ethyl, 2-hydroxy-ethyl, 2-hydroxy-1,1-dimethyl-ethyl, 1-hydroxymethyl-propyl, 2-methoxy-ethyl, cyclopropyl, cyclobutyl, 2-hydroxy-cyclopentyl, pyrrolidin-1-yl, tetrahydro-furan-3-yl, tetrahydro-pyran-4-yl, morpholin-4-yl, 3-methyl-oxetan-3-yl, 1-methyl-1H-pyrazol-4-yl or dimethyl-amine.

10. The compound of claim 9, wherein $R^3$ is isopropyl, 1-hydroxymethyl-propyl, cyclopropyl, 2-hydroxy-cyclopentyl or 1-methyl-1H-pyrazol-4-yl.

11. The compound of claim 1, wherein $R^2$ and $R^3$, together with the nitrogen atom to which they are attached, form a heterocyclyl.

12. The compound of claim 11, wherein $R^2$ and $R^3$, together with the nitrogen atom to which they are attached, form azetidin-1-yl, 1,1-dioxo-thiomorpholin-4-yl or morpholin-4-yl.

13. The compound of claim 1, wherein $R^4$ and $R^5$ are lower-alkyl.

14. The compound of claim 1 selected from the group consisting of:
6-(5-Hydroxymethyl-3-phenyl-isoxazol-4-ylmethoxy)-N-isopropyl-nicotinamide, N-(2-Hydroxy-ethyl)-6-(5-hydroxymethyl-3-phenyl-isoxazol-4-ylmethoxy)-nicotinamide, (1,1-Dioxo-1,6-thiomorpholin-4-yl)-{6-[3-(4-fluoro-phenyl)-5-hydroxymethyl-isoxazol-4-ylmethoxy]-pyridin-3-yl}-methanone,
6-[3-(4-Fluoro-phenyl)-5-hydroxymethyl-isoxazol-4-ylmethoxy]-N-isopropyl-nicotinamide,
6-[3-(4-Fluoro-phenyl)-5-hydroxymethyl-isoxazol-4-ylmethoxy]-N-(tetrahydro-pyran-4-yl)-nicotinamide,
N-Cyclopropylmethyl-6-[3-(4-fluoro-phenyl)-5-hydroxymethyl-isoxazol-4-ylmethoxy]-nicotinamide,
6-[3-(4-Fluoro-phenyl)-5-hydroxymethyl-isoxazol-4-ylmethoxy]-N-(2,2,2-trifluoro-ethyl)-nicotinamide,
N-Cyclopropyl-6-[3-(4-fluoro-phenyl)-5-hydroxymethyl-isoxazol-4-ylmethoxy]-nicotinamide,

69

6-[3-(4-Fluoro-phenyl)-5-hydroxymethyl-isoxazol-4-yl-methoxy]-N-(2-methoxy-ethyl)-nicotinamide, and 6-[3-(4-Fluoro-phenyl)-5-hydroxymethyl-isoxazol-4-yl-methoxy]-N-((1R,2R)-2-hydroxy-cyclopentyl)-nicotinamide or a pharmaceutically acceptable salt or ester thereof.

15. The compound of claim 1 selected from the group consisting of:

6-[3-(4-Fluoro-phenyl)-5-hydroxymethyl-isoxazol-4-yl-methoxy]-N-((1S,2S)-2-hydroxy-cyclopentyl)-nicotinamide, 6-[3-(4-Fluoro-phenyl)-5-hydroxymethyl-isoxazol-4-yl-methoxy]-N-(2,2,2-trifluoro-1-methyl-ethyl)-nicotinamide, 6-[3-(4-Fluoro-phenyl)-5-hydroxymethyl-isoxazol-4-yl-methoxy]-N-(2-hydroxy-1,1-dimethyl-ethyl)-nicotinamide, 6-[3-(4-Fluoro-phenyl)-5-hydroxymethyl-isoxazol-4-yl-methoxy]-N-(2,2,3,3,3-pentafluoro-propyl)-nicotinamide, 6-[3-(4-Fluoro-phenyl)-5-hydroxymethyl-isoxazol-4-yl-methoxy]-N-((R)-1-hydroxymethyl-propyl)-nicotinamide, 6-[3-(4-Fluoro-phenyl)-5-hydroxymethyl-isoxazol-4-yl-methoxy]-N-((S)-1-hydroxymethyl-propyl)-nicotinamide, 6-[3-(4-Fluoro-phenyl)-5-hydroxymethyl-isoxazol-4-yl-methoxy]-N-(1-methyl-1H-pyrazol-4-yl)-nicotinamide, 6-[3-(4-Fluoro-phenyl)-5-hydroxymethyl-isoxazol-4-yl-methoxy]-N-(3-methyl-oxetan-3-yl)-nicotinamide, {6-[3-(4-Chloro-phenyl)-5-hydroxymethyl-isoxazol-4-yl-methoxy]-pyridin-3-yl}-(1,1-dioxo-1,6-thiomorpholin-4-yl)-methanone, and 6-[3-(4-Chloro-phenyl)-5-hydroxymethyl-isoxazol-4-yl-methoxy]-N-isopropyl-nicotinamide or a pharmaceutically acceptable salt or ester thereof.

16. The compound of claim 1 selected from the group consisting of:

6-[3-(4-Chloro-phenyl)-5-hydroxymethyl-isoxazol-4-yl-methoxy]-N-cyclopropyl-nicotinamide, 6-[3-(4-Chloro-phenyl)-5-hydroxymethyl-isoxazol-4-yl-methoxy]-N-(2,2,2-trifluoro-ethyl)-nicotinamide, 6-[3-(4-Chloro-phenyl)-5-hydroxymethyl-isoxazol-4-yl-methoxy]-N,N-dimethyl-nicotinamide, 6-[3-(4-Chloro-phenyl)-5-hydroxymethyl-isoxazol-4-yl-methoxy]-N-(2-hydroxy-1,1-dimethyl-ethyl)-nicotinamide, 6-[3-(4-Chloro-phenyl)-5-hydroxymethyl-isoxazol-4-yl-methoxy]-N-(1-methyl-1H-pyrazol-4-yl)-nicotinamide, 6-[3-(4-Chloro-phenyl)-5-hydroxymethyl-isoxazol-4-yl-methoxy]-N-((S)-2,2,2-trifluoro-1-methyl-ethyl)-nicotinamide, 6-[3-(4-Chloro-phenyl)-5-hydroxymethyl-isoxazol-4-yl-methoxy]-N-((1R,2R)-2-hydroxy-cyclopentyl)-nicotinamide, 6-[3-(4-Chloro-phenyl)-5-hydroxymethyl-isoxazol-4-yl-methoxy]-N-((1S,2S)-2-hydroxy-cyclopentyl)-nicotinamide, 6-[3-(3,4-Difluoro-phenyl)-5-hydroxymethyl-isoxazol-4-ylmethoxy]-N-isopropyl-nicotinamide, and 6-[3-(3,4-Difluoro-phenyl)-5-hydroxymethyl-isoxazol-4-ylmethoxy]-N-(tetrahydro-pyran-4-yl)-nicotinamide or a pharmaceutically acceptable salt or ester thereof.

17. The compound of claim 1 selected from the group consisting of:

N-Cyclopropylmethyl-6-[3-(3,4-difluoro-phenyl)-5-hydroxymethyl-isoxazol-4-ylmethoxy]-nicotinamide, 6-[3-(3,4-Difluoro-phenyl)-5-hydroxymethyl-isoxazol-4-ylmethoxy]-N-(2,2,2-trifluoro-ethyl)-nicotinamide,

70

6-[3-(3,4-Difluoro-phenyl)-5-hydroxymethyl-isoxazol-4-ylmethoxy]-N-(2,2,2-trifluoro-1-methyl-ethyl)-nicotinamide, N-Cyclopropyl-6-[3-(3,4-difluoro-phenyl)-5-hydroxymethyl-isoxazol-4-ylmethoxy]-nicotinamide, 6-[3-(3,4-Difluoro-phenyl)-5-hydroxymethyl-isoxazol-4-ylmethoxy]-N-(2-hydroxy-1,1-dimethyl-ethyl)-nicotinamide, 6-[3-(3,4-Difluoro-phenyl)-5-hydroxymethyl-isoxazol-4-ylmethoxy]-N-(2,2,3,3,3-pentafluoro-propyl)-nicotinamide, 6-[3-(3,4-Difluoro-phenyl)-5-hydroxymethyl-isoxazol-4-ylmethoxy]-N-(2-methoxy-ethyl)-nicotinamide, 6-[3-(3,4-Difluoro-phenyl)-5-hydroxymethyl-isoxazol-4-ylmethoxy]-N-((R)-1-hydroxymethyl-propyl)-nicotinamide, 6-[3-(3,4-Difluoro-phenyl)-5-hydroxymethyl-isoxazol-4-ylmethoxy]-N-((S)-1-hydroxymethyl-propyl)-nicotinamide, and 6-[3-(3,4-Difluoro-phenyl)-5-hydroxymethyl-isoxazol-4-ylmethoxy]-N-(1-methyl-1H-pyrazol-4-yl)-nicotinamide or a pharmaceutically acceptable salt or ester thereof.

18. The compound of claim 1 selected from the group consisting of:

N-tert-Butyl-6-[3-(3,4-difluoro-phenyl)-5-hydroxymethyl-isoxazol-4-ylmethoxy]-nicotinamide, 6-[3-(3,4-Difluoro-phenyl)-5-hydroxymethyl-isoxazol-4-ylmethoxy]-N-morpholin-4-yl-nicotinamide, 6-[3-(3,4-Difluoro-phenyl)-5-hydroxymethyl-isoxazol-4-ylmethoxy]-N-pyrrolidin-1-yl-nicotinamide, (1,1-Dioxo-1,6-thiomorpholin-4-yl)-[6-(5-hydroxymethyl-3-pyridin-2-yl-isoxazol-4-ylmethoxy)-pyridin-3-yl]-methanone, 6-(5-Hydroxymethyl-3-pyridin-2-yl-isoxazol-4-ylmethoxy)-N-isopropyl-nicotinamide, 6-(5-Hydroxymethyl-3-pyridin-2-yl-isoxazol-4-ylmethoxy)-N-(tetrahydro-furan-3-yl)-nicotinamide, 6-(5-Hydroxymethyl-3-pyridin-2-yl-isoxazol-4-ylmethoxy)-nicotinic acid N',N'-dimethyl-hydrazide, 6-(5-Hydroxymethyl-3-pyridin-2-yl-isoxazol-4-ylmethoxy)-N-(tetrahydro-pyran-4-yl)-nicotinamide, 6-(5-Hydroxymethyl-3-pyridin-2-yl-isoxazol-4-ylmethoxy)-N-morpholin-4-yl-nicotinamide, and 6-(3-Butyl-5-hydroxymethyl-isoxazol-4-ylmethoxy)-N-isopropyl-nicotinamide or a pharmaceutically acceptable salt or ester thereof.

19. The compound of claim 1 selected from the group consisting of:

6-(3-Butyl-5-hydroxymethyl-isoxazol-4-ylmethoxy)-N-(3-methyl-oxetan-3-yl)-nicotinamide, 6-(3-Butyl-5-hydroxymethyl-isoxazol-4-ylmethoxy)-N-(2,2,2-trifluoro-ethyl)-nicotinamide, 6-(3-Butyl-5-hydroxymethyl-isoxazol-4-ylmethoxy)-N-cyclobutyl-nicotinamide, Azetidin-1-yl-[6-(3-butyl-5-hydroxymethyl-isoxazol-4-ylmethoxy)-pyridin-3-yl]-methanone,

[6-(5-Hydroxymethyl-3-pyridin-2-yl-isoxazol-4-ylmethoxy)-pyridin-3-yl]-morpholin-4-yl-methanone,

[6-(3-Butyl-5-hydroxymethyl-isoxazol-4-ylmethoxy)-pyridin-3-yl]-(1,1-dioxo-thiomorpholin-4-yl)-methanone, and (1,1-Dioxo-1,6-thiomorpholin-4-yl)-{6-[3-(5-fluoro-pyridin-2-yl)-5-hydroxymethyl-isoxazol-4-ylmethoxy]-pyridin-3-yl}-methanone, or a pharmaceutically acceptable salt or ester thereof.

20. The compound of claim 1 selected from the group consisting of:

6-[3-(4-Chloro-phenyl)-5-hydroxymethyl-isoxazol-4-yl-methoxy]-N-isopropyl-nicotinamide, 6-[3-(4-Fluoro-phenyl)-5-hydroxymethyl-isoxazol-4-yl-methoxy]-N-((S)-1-hydroxymethyl-propyl)-nicotinamide, 6-[3-(4-Chloro-phenyl)-5-hydroxymethyl-isoxazol-4-yl-methoxy]-N41R,2R)-2-hydroxy-cyclopentyl)-nicotinamide, 6-[3-(4-Chloro-phenyl)-5-hydroxymethyl-isoxazol-4-yl-methoxy]-N-((1S,2S)-2-hydroxy-cyclopentyl)-nicotinamide, 6-[3-(4-Chloro-phenyl)-5-hydroxymethyl-isoxazol-4-yl-methoxy]-N-(1-methyl-1H-pyrazol-4-yl)-nicotinamide, 6-(5-Hydroxymethyl-3-pyridin-2-yl-isoxazol-4-yl-methoxy)-N-isopropyl-nicotinamide, 6-[3-(4-Fluoro-phenyl)-5-hydroxymethyl-isoxazol-4-yl-methoxy]-N-(1-methyl-1H-pyrazol-4-yl)-nicotinamide, and 6-[3-(4-Chloro-phenyl)-5-hydroxymethyl-isoxazol-4-yl-methoxy]-N-cyclopropyl-nicotinamide, or a pharmaceutically acceptable salt and ester thereof.

21. A pharmaceutical composition comprising a therapeutically effective amount of a compound of formula I

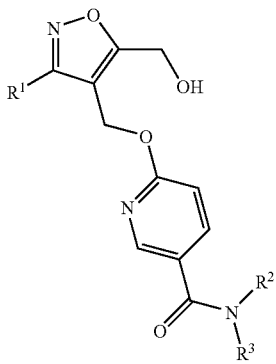

wherein $R^1$ is lower-alkyl, aryl or heteroaryl, wherein lower-alkyl is optionally substituted with 1-4 substituents independently selected from the group consisting of halogen, cyano, hydroxy and lower-alkoxy, and wherein aryl and heteroaryl are optionally substituted with 1-4 substituents independently selected from the group consisting of halogen, cyano, lower-alkyl, lower-alkyl substituted by halogen, lower-alkyl substituted by hydroxy, lower-alkyl-C(O)OH, lower-alkyl-C(O)O-lower-alkyl, lower-alkyl-CO—$NH_2$, lower-alkyl-CO—N(H,lower-alkyl), lower-alkyl-CO—N(lower-alkyl)$_2$, lower-alkyl-N(H,lower-alkyl), lower-alkyl-N(lower-alkyl)$_2$, lower-alkoxy-lower-alkyl, CO-lower-alkyl, COOH, COO-lower-alkyl, $CONH_2$, CON(H,lower-alkyl), CON(lower-alkyl)$_2$, cycloalkyl, heterocyclyl, aryl, heteroaryl, $NH_2$, N(H, lower-alkyl), N(lower-alkyl)$_2$, hydroxy, lower-alkoxy, phenyloxy, $SO_2$-lower-alkyl, $SO_2$—$NH_2$, $SO_2$—N(H,lower-alkyl) and $SO_2$—N(lower-alkyl)$_2$;

$R^2$ is hydrogen or lower-alkyl;

$R^3$ is lower-alkyl, lower-alkyl substituted by halogen, lower-alkyl substituted by hydroxy, cycloalkyl, cycloalkyl substituted by hydroxy, heterocyclyl, heterocyclyl substituted by lower-alkyl, heteroaryl, heteroaryl substituted by lower-alkyl, $(CH_2)_n$—O-lower-alkyl or $NR^4R^5$;

or wherein $R^2$ and $R^3$, together with the nitrogen atom to which they are attached, form a heterocyclyl;

n is 1 or 2;

$R^4$ and $R^5$ are each independently selected from hydrogen and lower-alkyl;

or a pharmaceutically acceptable salt or ester thereof and a pharmaceutically acceptable carrier.

* * * * *